United States Patent [19]

Philipps et al.

[11] Patent Number: 6,018,054
[45] Date of Patent: Jan. 25, 2000

[54] 7-ISOINDOLINYL-QUINOLONE DERIVATIVES AND 7-ISOINDOLINYL-NAPHTHYRIDONE DERIVATIVES

[75] Inventors: Thomas Philipps, Cologne; Stephan Bartel, Bergisch Gladbach; Andreas Krebs, Odenthal; Uwe Petersen, Leverkusen; Thomas Schenke, Bergisch Gladbach; Klaus-Dieter Bremm, Wuppertal; Rainer Endermann, Wuppertal; Karl Georg Metzger, Wuppertal; Burkhard Mielke, Leverkusen, all of Germany

[73] Assignee: Bayer Aktiengesellschaft, Leverkusen, Germany

[21] Appl. No.: 08/979,751

[22] Filed: Nov. 26, 1997

Related U.S. Application Data

[62] Division of application No. 08/649,380, May 17, 1996, Pat. No. 5,739,339, which is a division of application No. 08/119,369, Sep. 10, 1993, Pat. No. 5,556,979.

[30] Foreign Application Priority Data

Sep. 15, 1992 [DE] Germany .............................. 42 30 804

[51] Int. Cl.$^7$ ...................... C07D 491/08; C07D 209/44; C07D 209/56
[52] U.S. Cl. ......................... 548/430; 544/101; 546/123; 546/156; 548/434; 548/470; 548/515
[58] Field of Search ..................... 548/470, 430, 548/434, 515; 546/123, 156; 544/101

[56] References Cited

U.S. PATENT DOCUMENTS

| | | | |
|---|---|---|---|
| 5,457,104 | 10/1995 | Bartel et al. | 514/234.5 |
| 5,468,742 | 11/1995 | Petersen et al. | 514/187 |
| 5,659,038 | 8/1997 | Himmler et al. | 546/156 |

FOREIGN PATENT DOCUMENTS

| | | |
|---|---|---|
| 343524 | 11/1989 | European Pat. Off. . |
| 343560 | 11/1989 | European Pat. Off. . |
| 429304 | 5/1991 | European Pat. Off. . |
| 516861 | 12/1992 | European Pat. Off. . |

OTHER PUBLICATIONS

Torosyan et al. Arm. Khim. Zh., 30, pp. 578, 581, 1977.
Chemical Abstracts, vol. 88, 1978, p. 480; 37558f: "Studies on amines and ammonium compounds, CXXXII. Intramolecular thermal . . . ", R.S. Mkrtchyan, et al.
Chemical Abstracts Service Registry Handbook, 1977 supplement, Registry Nos. 63306–25–2 through 65229–05–2, 2 pgs. CAS RN 65093–23–4, Armyanskii Khimicheskii Zhurnal, Bd. 30, Nr. 7, Yerevan, Seiten 573–577.
"Synthesis of Hyroisoindoles via Intramolecular Diels–Alder Reactions of Functionalised Amino Trienes", J.M. Mellor and A.M. Wagland; *J. Chem. Soc. Perkin Trans.* 1989, 997–1005.
"The Intramolecular Diels–Alder Reaction", Engelbert Ciganek, pp. 1–375,1984.
"Studies on the Total Synthesis of Chlorothricolide: Stereochemical Aspects of the the Intramolecular Diels–Alder Reactions of Methyl Undeca–2,8,10–Trienoates", Wm. Roush and S.E. Hall; *J. Chem. Soc.,* 1981, 103, 5200–5211.
"Protection for the Amino Groups" pp. 219–286 (1981).
Fernandez S et al. Rev. Latinoam. Quim. 18(1), 50–1, 1987.

*Primary Examiner*—Evelyn Mei Huang
*Attorney, Agent, or Firm*—Sprung Kramer Schaefer & Briscoe

[57] ABSTRACT

The invention relates to intermediate compounds for preparing novel quinolone derivatives- and naphthyridone derivatives which are substituted in the 7-position by a partially hydrogenated isoindolinyl ring, to processes for their preparation and to antibacterial agents and feed additives containing them.

3 Claims, No Drawings

7-ISOINDOLINYL-QUINOLONE DERIVATIVES AND 7-ISOINDOLINYL-NAPHTHYRIDONE DERIVATIVES

This application is a divisional of application Ser. No. 08/649,380, filed May 17, 1996 U.S. Pat. No. 5,739,339 which is a divisional of Ser. No. 08/119,369 filed on Sep. 10, 1993, U.S. Pat. No. 5,556,979.

The invention relates to novel quinolone derivatives and naphthyridone derivatives which are substituted in the 7-position by a partially hydrogenated isoindolinyl ring, to processes for their preparation and to antibacterial agents and feed additives containing them.

Quinolone derivatives and naphthyridone derivatives have already become known from EP-A-343 560 which are substituted in the 7-position by an isoindolinyl ring, such as, e.g., 7-(2-isoindolinyl)-1-cyclopropyl-6,8-difluoro-1,4-dihydro-4-oxo-3-quinolinecarboxylic acid. However, these compounds are only distinguished by a slight antibacterial activity.

In addition, quinolonecarboxylic acids and napthyridonecarboxylic acids are known from EP-A-343 524 which are substituted in the 7-position by a perhydrogenated isoindolinyl ring, such as, e.g., 7-[(1-RS, 2RS, 6SR)-2-amino-8-azabicyclo[4.3.0]non-8-yl]-1-cyclopropyl-6,8-difluoro-1,4-dihydro-4-oxo-3-quinolinecarboxylic acid.

Furthermore, (−)-7-[(1R,2R,6S)-2-amino-8-azabicyclo-[4.3.0]non-3-en-8-yl]-1-cyclopropyl-6,8-difluoro-1,4-dihydro-4-oxo-3-quinolinecarboxylic acid is known (T. Yoshinari et al., poster presentation at the congress: "Topoisomerases in Chemotherapy", Nagoya (Japan), November 1991).

It has been found that the compounds of the formula (I)

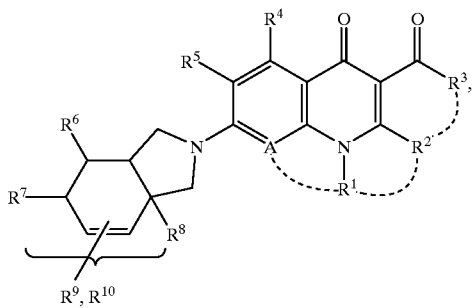

(I)

in which $R^1$ represents alkyl having 1 to 4 carbon atoms, which is optionally substituted by 1–3 fluorine atoms, alkenyl having 2 to 4 carbon atoms, cycloalkyl having 3 to 6 carbon atoms, which is optionally substituted by 1 to 2 fluorine atoms, 2-hydroxyethyl, methoxy, amino, methylamino, ethylamino, dimethylamino, phenyl, which is optionally substituted by 1 or 2 fluorine atoms, 3-oxetanyl, bicyclo[1.1.1]pentyl, $R^2$ represents hydrogen or else, together with $R^1$, can form a bridge, so that a 4- or 5-membered ring results, $R^3$ represents hydroxyl or O—$R^{11}$, wherein $R^{11}$ represents alkyl having 1–4 C atoms or $R^3$, together with $R^2$, can form a bridge, so that a 5- or 6-membered ring results, $R^4$ represents hydrogen, amino, alkylamino having 1 to 4 carbon atoms, dialkylamino having 1 to 3 carbon atoms in each alkyl group, hydroxyl, alkoxy having 1 to 4 carbon atoms, mercapto, alkylthio having 1 to 4 carbon atoms, halogen, methyl, ethyl or vinyl, $R^5$ represents hydrogen, halogen or methyl, $R^6$ represents hydrogen, alkyloxycarbonyl having 1 to 4 carbon atoms, hydroxymethyl,

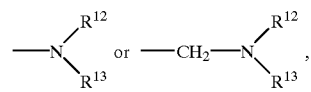

where $R^{12}$ denotes hydrogen, alkyl having 1 to 3 carbon atoms, which is optionally substituted by hydroxyl, alkyloxycarbonyl having 1 to 4 carbon atoms in the alkyl moiety, or acyl having 1 to 3 carbon atoms, and $R^{13}$ denotes hydrogen or methyl, $R^7$, $R^8$, $R^9$ and $R^{10}$ each represent hydrogen or methyl or $R^9$ and $R^{10}$ each represent hydrogen or methyl and $R^7$, together with $R^8$, can form a bridge of the structure —O—, —$CH_2$— or —$CH_2$—$CH_2$—, and A represents N or C—$R^{14}$, wherein $R^{14}$ represents hydrogen, halogen, methyl, which is optionally substituted by 1 to 3 fluorine atoms, ethinyl, vinyl, hydroxyl or methoxy, or else, together with $R^1$, can form a bridge, so that a 5- or 6-membered ring results, or else, together with $R^1$ and $R^2$, can form a bridge, so that two 5- or 6-membered rings result, and their tautomers as well as their pharmaceutically utilisable hydrates and acid-addition salts, and the alkali metal, alkaline earth metal, silver and guanidinium salts of the underlying carboxylic acids, possess a higher antibacterial effect than the state of the art, in particular in the Gram-positive domain.

The compounds of the formula (I) are preferred in which $R^1$ represents cyclopropyl, 2-fluorocyclopropyl, ethyl, 2-fluoroethyl, tert-butyl, which is optionally substituted by 1, 2 or 3 fluorine atoms, or phenyl, which is optionally substituted by 1 or 2 fluorine atoms, 3-oxetanyl, bicyclo[1.1.1]pentyl, $R^2$ represents hydrogen or else, together with $R^1$, can form a bridge of the structure *

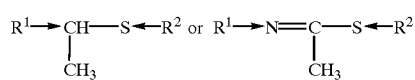

(*: If two or more radicals together form a bridge, arrows indicate the centres of the general formula to which the bridging atoms are linked. For example,

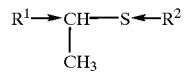

denotes that CH is linked to the centre of the general formula (I) which is substituted by $R^1$, and that S is linked to the centre of the general formula (I) which is substituted by $R^2$.)

$R^3$ represents hydroxyl or O—$R^{11}$, wherein $R^{11}$ represents alkyl having 1–4 C atoms, or $R^3$, together with $R^2$, can form a bridge of the structure

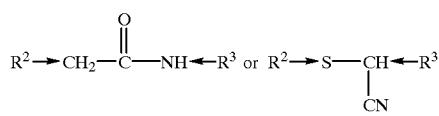

$R^4$ represents hydrogen, fluorine, chlorine, amino, hydroxyl, methyl or vinyl,
$R^5$ represents hydrogen, fluorine, chlorine, bromine or methyl,
$R^6$ represents amino, methylamino, ethoxycarbonylamino, aminomethyl, ethoxycarbonylaminomethyl, hydroxymethyl, ethoxycarbonyl or hydrogen,
$R^7$, $R^8$, $R^9$ and $R^{10}$ each represent hydrogen or methyl or $R^9$ and $R^{10}$ each represent hydrogen or methyl and $R^7$, together with $R^8$, can form a bridge of the structure —O—, —$CH_2$ or —$CH_2$—$CH_2$—, and
A represents N or C—$R^{14}$, wherein
  $R^{14}$ represents hydrogen, fluorine, chlorine, bromine, methyl, which is optionally substituted by 1 to 3 fluorine atoms, ethinyl, vinyl or methoxy, or else, together with $R^1$, can form a bridge of the structure

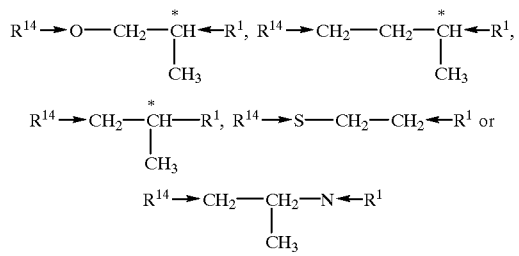

or else, together with $R^1$ and $R^2$, can form a bridge of the structure

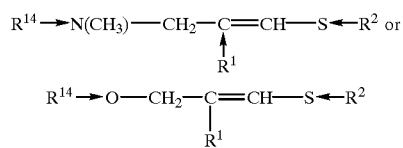

and their tautomers as well as their pharmaceutically utilisable hydrates and acid-addition salts, and the alkali metal, alkaline earth metal, silver and guanidinium salts of the underlying carboxylic acids.

The compounds of the formula (I) are particularly preferred in which
$R^1$ represents cyclopropyl, cis-2-fluorocyclopropyl, ethyl, tert-butyl or 2,4-difluorophenyl,
$R^2$ represents hydrogen,
$R^3$ represents hydroxyl or ethoxy,
$R^4$ represents hydrogen, fluorine or amino,
$R^5$ represents hydrogen or fluorine,
$R^6$ represents amino, methylamino, ethoxycarbonylamino, aminomethyl, ethoxycarbonylaminomethyl, hydroxymethyl, ethoxycarbonyl or hydrogen,
$R^7$, $R^8$, $R^9$ and $R^{10}$ each represent hydrogen or methyl, and
A represents N or C—$R^{14}$, wherein
  $R^{14}$ represents hydrogen, fluorine or chlorine, or else, together with $R^1$, can form a bridge of the structure

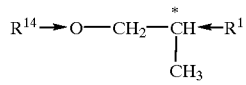

and their tautomers as well as their pharmaceutically utilisable hydrates and acid-addition salts, and the alkali metal, alkaline earth metal, silver and guanidinium salts of the underlying carboxylic acids.

In addition, it has been found that the compound of the formula (I) is obtained if a compound of the formula (II)

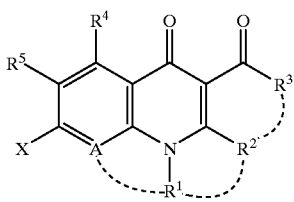

in which $R^1$, $R^2$, $R^3$, $R^4$, $R^5$ and A have the abovementioned meaning and X represents halogen, in particular fluorine or chlorine, is reacted with compounds of the formula (III)

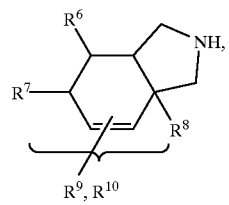

in which $R^6$, $R^7$, $R^8$, $R^9$ and $R^{10}$ have the abovementioned meaning, optionally in the presence of acid binders, and protective groups which may optionally be present are eliminated by alkaline or acid hydrolysis, and the resulting compounds are optionally converted into their alkali metal, alkaline earth metal, silver or guanidinium salts.

If, for example, 1-cyclopropyl-6,7,8-trifluoro-1,4-dihydro-4-oxo-quinolinecarboxylic acid and (1SR, 2RS, 6SR)-2-ethoxycarbonylamino-8-azabicyclo[4.3.0]non-4-ene are used as the starting compounds, the course of the reaction can then be represented by the following formula diagram:

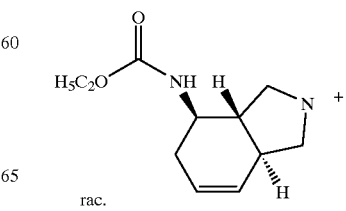

rac.

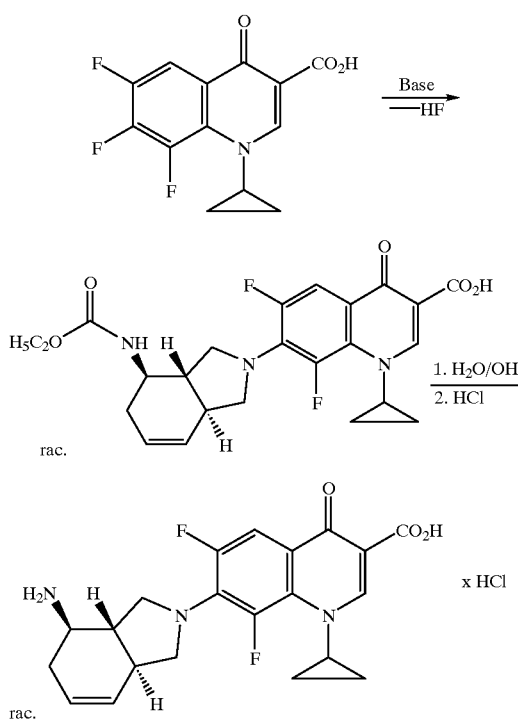

If, for example, 1-cyclopropyl-5,6,8-trifluoro-1,4-dihydro-7-[(1SR, 2RS, 6SR)-2-methylamino-8-azabicyclo[4.3.0]non-4-en-8-yl]-4-oxo-3-quinolinecarboxylic acid and ammonia are used as the starting compounds, the course of the reaction can then be represented by the following diagram:

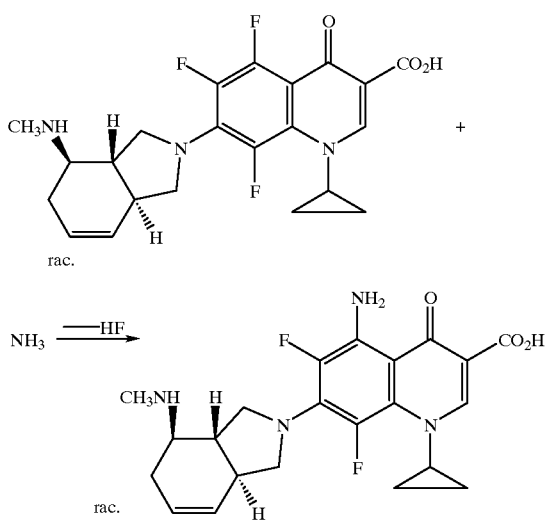

If, for example, ethyl 7-chloro-1-cyclopropyl-6-fluoro-1,4-dihydro-4-oxo-1,8-naphthyridine-3-carboxylate and (1SR, 2RS, 6SR)-2-methylamino-8-azabicyclo[4.3.0]non-4-ene are used as the starting compounds, the course of the reaction can then be represented by the following formula diagram:

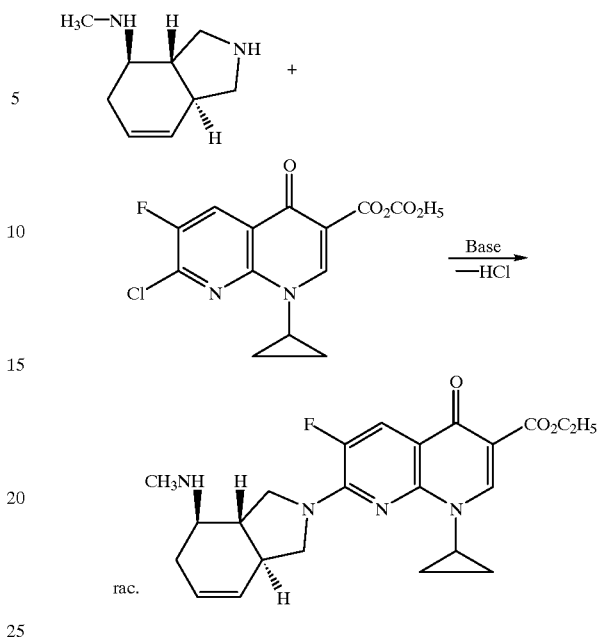

The reaction of (II) with (III), in which the compounds (III) can also be employed in the form of their salts, such as, e.g., the hydrochlorides, is preferably undertaken in a diluent, such as dimethyl sulphoxide, N,N-dimethylformamide, N-methylpyrrolidone, hexamethylphosphoric triamide, sulpholane, acetonitrile or water, or an alcohol, such as methanol, ethanol, n-propanol, isopropanol, glycol monomethyl ether or pyridine. Mixtures of these diluents can likewise be used.

All customary inorganic and organic acid-binding agents can be used as acid binders. These preferably include the alkali metal hydroxides, alkali metal carbonates and organic amines and amidines. Those which may be mentioned individually as being particularly suitable are: triethylamine, 1,4-diazabicyclo[2.2.2]octane (DABCO), 1,8-diazabicyclo[5.4.0]undec-7-ene (DBU) or excess amine (III).

The reaction temperatures can be varied over a relatively wide range. In general, temperatures of between about 20 and 200° C., preferably of between 40 and 100° C., are employed.

While the reaction can be carried out under atmospheric pressure, it can also be carried out under elevated pressure. In general, pressures of between about 1 and 100 bar, preferably of between 1 and 10 bar, are employed.

In carrying out the process according to the invention, 1 to 15 mol, preferably 1 to 6 mol, of the compound (III) are employed per 1 mol of the compound (II).

Free amino groups can be protected during the reaction by a suitable amino-protective group, e.g. tert-butyloxycarbonyl or ethoxycarbonyl, or as an azomethine group, and liberated again once the reaction is complete by treatment with a suitable acid, such as hydrochloric acid or trifluoroacetic acid, or with a suitable base, such as sodium hydroxide solution or potassium hydroxide solution (T.W. Greene, Protective Groups in Organic Synthesis, page 218–288, John Wiley & Sons, 1981).

The preparation of the acid-addition salts of the compounds according to the invention takes place in a customary manner, for example by dissolving the betaine in excess aqueous acid and precipitating the salt with an organic solvent which is miscible with water, such as methanol, ethanol, acetone or acetonitrile. Equivalent quantities of betaine and acid can also be heated in water or an alcohol, such as glycol mondmethyl ether, and the mixture subsequently evaporated to dryness, or the precipitated salt filtered off with suction. Pharmaceutically utilisable salts are to be understood to mean, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal or alkaline earth metal salts of the carboxylic acids according to the invention are obtained, for example, by dissolving the betaine in a sub-equivalent quantity of alkali metal or alkaline earth metal solution, filtering off from the undissolved betaine, and evaporating the filtrate to dryness. Sodium, potassium or calcium salts are pharmaceutically suitable. The corresponding silver salts are obtained by reacting an alkali metal or alkaline earth metal salt with a suitable silver salt, such as silver nitrate.

Most of the compounds of the formula (II) used as starting compounds are known, or can be prepared according to known methods. Examples which may be mentioned are:

7-Chloro-1-cyclopropyl-6-fluoro-1,4-dihydro-4-oxo-3-quinolinecarboxylic acid,
1-Cyclopropyl-6,7-difluoro-1,4-dihydro-4-oxo-3-quinolinecarboxylic acid,
6-Chloro-1-cyclopropyl-7,8-difluoro-1,4-dihydro-4-oxo-3-quinolinecarboxylic acid,
8-Chloro-1-cyclopropyl-6, 7-difluoro-1,4-dihydro-4-oxo-3-quinolnecarboxylic acid,
1-Cyclopropyl-6,7,8-trifluoro-1,4-dihydro-4-oxo-3-quinolinecarboxylic acid,
5-Bromo-1-cyclopropyl-6,7,8-trifluoro-1,4-dihydro-4-oxo-3-quinolinecarboxylic acid,
5-Bromo-1-(2,4-difluorophenyl)-6,7,8-trifluoro-1,4-dihydro-4-oxo-3-quinolinecarboxylic acid,
1-Cyclopropyl-6,7-difluoro-1,4-dihydro-8-methyl-4-oxo-3-quinolinecarboxylic acid,
6,7-Difluoro-1-ethyl-1,4-dihydro-4-oxo-3-quinolinecarboxylic acid,
6,7,8-Trifluoro-1-ethyl-1,4-dihydro-4-oxo-3-quinolinecarboxylic acid,
7-Chloro-6-fluoro-1,4-dihydro-1-(2-hydroxyethyl)-4-oxo-3-quinolinecarboxylic acid,
6,7-Difluoro-1-(2-fluoroethyl)-1,4-dihydro-4-oxo-3-quinolinecarboxylic acid,
7-Chloro-6-fluoro-1,4-dihydro-1-methoxy-4-oxo-3-quinolinecarboxylic acid,
7-Chloro-6-fluoro-1,4-dihydro-1-methylamino-4-oxo-3-quinolinecarboxylic acid,
6,7-Difluoro-1,4-dihydro-4-oxo-1-phenyl-3-quinolinecarboxylic acid,
7-Chloro-1-cyclopropyl-6-fluoro-1,4-dihydro-4-oxo-1,8-naphthyridine-3-carboxylic acid,
Ethyl 7-chloro-1-cyclopropyl-6-fluoro-1,4-dihydro-4-oxo-1,8-naphthyridine-3-carboxylate,
Ethyl 1-cyclopropyl-6,7,8-trifluoro-1,4-dihydro-4-oxo-3-quinolinecarboxylate,
9,10-Difluoro-2,3-dihydro-3-methyl-7-oxo-7H-pyrido-[1,2,3-de][1,4-benzoxacine-6-carboxylic acid,
8,9-Difluoro-6,7-dihydro-5-methyl-1-oxo-1H,5H-benzo[i,j] quinolicine-2-carboxylic acid,
7-Chloro-6-fluoro-1-phenyl-1,4-dihydro-4-oxo-1,8-naphthyridine-3-carboxylic acid,
Ethyl 7-chloro-6-fluoro-1-(4-fluorophenyl)-1,4-dihydro-4-oxo-1,8-naphthyridine-3-carboxylate,
6,7,8-Trifluoro-1,4-dihydro-1-methylamino-4-oxo-3-quinolinecarboxylic acid,
1-Amino-6,7,8-trifluoro-1,4-dihydro-4-oxo-3-quinolinecarboxylic acid,
6,7,8-Trifluoro-1,4-dihydro-1-dimethylamino-4-oxo-3-quinolinecarboxylic acid,
6,7-Difluoro-1-(4-fluorophenyl)-1,4-dihydro-8-methyl-4-oxo-3-quinolinecarboxylic acid,
7-Chloro-6-fluoro-1-(4-fluorophenyl)-1,4-dihydro-4-oxo-3-quinolinecarboxylic acid,
7-Chloro-6-fluoro-1-(2,4-difluorophenyl)-1,4-dihydro-4-oxo-3-quinolinecarboxylic acid,
6,7,8-Trifluoro-1-(4-fluorophenyl)-1,4-dihydro-4-oxo-3-quinolinecarboxylic acid,
6,7,8-Trifluoro-1-(2,4-difluorophenyl)-1,4-dihydro-4-oxo-3-quinolinecarboxylic acid,
6,7,8-Trifluoro-1,4-dihydro-4-oxo-1-phenyl-3-quinolinecarboxylic acid,
7-Chloro-1-ethyl-6-fluoro-1,4-dihydro-4-oxo-1,8-naphthyridine-3-carboxylic acid,
6,7-Difluoro-1,4-dihydro-4-oxo-1-vinyl-3-quinolinecarboxylic acid,
1-Cyclopropyl-5,6,7,8-tetrafluoro-1,4-dihydro-4-oxo-3-quinolinecarboxylic acid,
5-Amino-1-cyclopropyl-6,7,8-trifluoro-1,4-dihydro-4-oxo-3-quinolinecarboxylic acid,
1-Cyclopropyl-6,7,8-trifluoro-1,4-dihydro-5-hydroxy-4-oxo-3-quinolinecarboxylic acid,
1-Cyclopropyl-6,7-difluoro-1,4-dihydro-8-methoxy-4-oxo-3-quinolinecarboxylic acid,
7-Chloro-1-(2,4-difluorophenyl)-6-fluoro-1,4-dihydro-4-oxo-1,8-naphthyridine-3-carboxylic acid,
Ethyl 7-chloro-1-(2,4-difluorophenyl)-6-fluoro-1,4-dihydro-4-oxo-1,8-naphthyridine-3-carboxylate,
9,1-Epoxymethano-7,8-difluoro-5-oxo-5H-thiazolo[3,2-a] quinoline-4-carboxylic acid,
1-Cyclopropyl-6,7-difluoro-1,4-dihydro-4-oxo-8-trifluoromethyl-3-quinolinecarboxylic acid,
9,10-Difluoro-2,3-dihydro-7-oxo-7H-pyrido[1,2,3-de][1,4] benzothiazine-6-carboxylic acid,
6,7,8-Trifluoro-1-methyl-4-oxo-1H,4H-[1,3]thiazeto[3,2-a]-3-quinolinecarboxylic acid,
1-Cyclopropyl-6,7,8-trifluoro-1,4-dihydro-5-methyl-4-oxo-3-quinolinecarboxylic acid,
9-Cyclopropyl-6,7-difluoro-2,3,4,9-tetrahydro-5-methylisothiazolo[5,4-b]quinolin-3,4-dione,
6,7-Difluoro-1-(1,2-cis-2-fluorocyclopropyl)-1,4-dihydro-4-oxo-3-quinolinecarboxylic acid,
6,7,8-Trifluoro-1-(1,2-cis-2-fluorocyclopropyl)-1,4-dihydro-4-oxo-3-quinolinecarboxylic acid,
8-Chloro-6,7-difluoro-1-(1,2-cis-2-fluorocyclopropyl)-1,4-dihydro-4-oxo-3-quinolinecarboxylic acid,
7-Chloro-6-fluoro-1-(1,2-cis-2-fluorocyclopropyl)-1,4-dihydro-4-oxo-1,8-naphthyridine-3-carboxylic acid,
1-Cyclopropyl-8-difluoromethoxy-6,7-difluoro-1,4-dihydro-4-oxo-3-quinolinecarboxylic acid (EP-A-352 123),
8,9-Difluoro-1,2-dihydro-2-methyl-6-oxo-6H-pyrrolo[3,2,1-ij]quinoline-5-carboxylic acid,
8-Chloro-6,7-difluoro-1,4-dihydro-1-(oxetan-3-yl)-4-oxo-3-quinolinecarboxylic acid,
9,1-(Methylimino)methano-7,8-difluoro-5-oxo-5H-thiazolo [3,2-a]quinoline-4-carboxylic acid,
1-Cyclopropyl-6,7-difluoro-1,4-dihydro-4-oxo-8-vinyl-3-quinolinecarboxylic acid,
7,8-Difluoro-2-methyl-5-oxo-5H-[1,3,4]thiadiazolo[3,2,-a] quinoline-4-carboxylic acid,
5-Cyclopropyl-6,7,8-trifluoro-1-hydroxy-2,3,5,10-tetrahydro-3,10-dioxobenzo[b]-1,6-naphthyridine, 9-Cyclopropyl-6,7-difluoro-3-hydroxy-4,9-dihydro-4-oxothieno[2,3-b]quinoline-2-carbonitrile,
4,5-Difluoro-2,3-dihydro-1-methyl-7-oxo-1H,7H-pyrido-[3,2,1-ij]cinnoline-8-carboxylic acid,
1-Bicyclo[1.1.1]pentyl-6,7-difluoro-1,4-dihydro-4-oxo-3-quinolinecarboxylic acid,
1-tert-Butyl-6,7-difluoro-1,4-dihydro-4-oxo-3-quinolinecarboxylic acid,
7-Chloro-6-fluoro-1-(1-fluoromethyl-1-methyl-ethyl)-1,4-dihydro-4-oxo-1,8-naphthyridine-3-carboxylic acid,
5,8-Dichloro-1-cyclopropyl-6,7-difluoro-1,4-dihydro-4-oxo-3-quinolinecarboxylic acid.

The compounds of the formula (III) which are used as starting compounds are novel. A process for preparing the compounds of the general formula (III) according to the invention

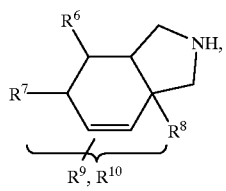
(III)

in which $R^6$, $R^7$, $R^8$, $R^9$ and $R^{10}$ have the abovementioned meaning, has been found which is characterised in that suitable dienes are reacted with suitable dienophiles in a Diels-Alder reaction, which can be carried out intermolecularly or intramolecularly, and further chemical reactions are optionally carried out subsequently in order optionally to construct the pyrrolidine ring and in order to introduce desired substituents for the biological effect, and, as the last step, the protective group on the pyrrolidine nitrogen is eliminated.

In the case of intramolecular implementation of the Diels-Alder reaction, compounds of the formula (1) or (2)

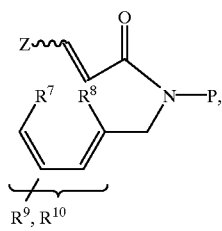
(1)

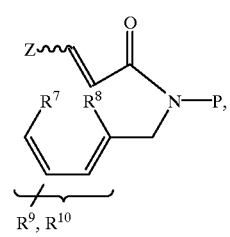
(2)

in which
$R^7$, $R^8$, $R^9$ and $R^{10}$ have the abovementioned meaning and
P represents a protective group (for example allyl, acyl, carbamoyl or trityl),
Z represents hydrogen, a carboxyl group, a carboxylic ester group or a carboxamide group, CN or $NO_2$, are reacted to give the compounds of the formula (3) [starting from (1)] or (4) [starting from (2)]

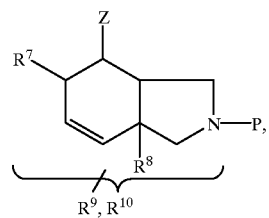
(3)

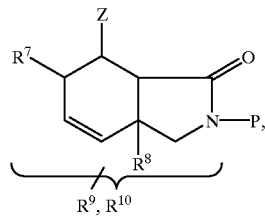
(4)

in which $R^7$, $R^8$, $R^9$, $R^{10}$, P and Z have the abovementioned meaning. Intramolecular Diels-Alder reactions of a similar nature are known in some cases: J. M. Mellor, A. M. Wagland; J. Chem. Soc. Perkin I, 997–1005 (1989); W. R. Roush, S. E. Hall; J. Am. Chem. Soc. 103, 5200 (1980). E. Ciganek; Organic Reactions 32, 1–374 (1984). However, these papers make no reference to protective groups which are suitable for the reaction and which at the same time can subsequently be eliminated without difficulty.

In the case of intermolecular implementation of the Diels-Alder reaction, dienes of the formula (5) are reacted with dienophiles of the formula (6) to give compounds of the formula (7) and, optionally after modification of the groups $Z^1$ and $Z^2$, for example conversion of a cyclic carboxylic anhydride into a diester with elimination of the protective groups $P^1$ or $P^1$ and $P^2$, reacted with cyclisation to give the lactams of the formula (8).

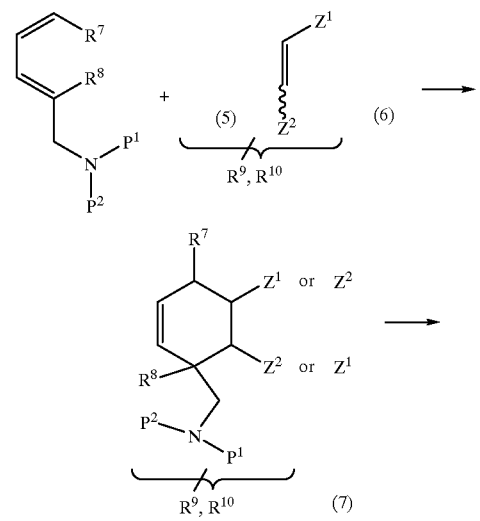

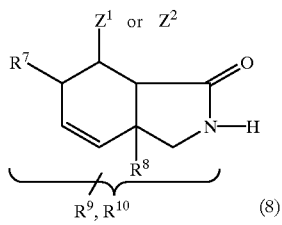

In the formula (5), (6), (7) and (8), $R^7$, $R^8$, $R^9$ and $R^{10}$ have the abovementioned meaning, $P^1$ represents an acyl or carbamoyl protective group, if $P^2$ represents hydrogen or $P^1$ forms, together with $P^2$, an imide, $Z^1$ and $Z^2$ represent hydrogen, carboxyl, carboxylic ester groups or carboxamide groups, CN or $NO_2$, where at least one of the two groups $Z^1$ or $Z^2$ must be a carboxylatic ester group or a carboxamide group or CN, or $Z^1$ and $Z^2$ together form a bridge, so that a cyclic carboxylic anhydride is formed.

Preferred protective groups P, $P^1$ and $P^2$ are those protective groups in which, under the conditions which are used for their elimination, the cyclisation to the lactam, and optionally esterification of a second carboxyl function, which is still free, with the alcohol used as solvent, takes place in such a way that all the reaction steps can be carried out in a one-pot reaction, and an uncontrolled conversion of optionally diastereomerically and enantiomerically pure starting compounds into isomeric mixtures which are difficult or impossible to resolve does not take place.

Examples which may be mentioned are:
1. the tert-butyloxycarbonyl protective group (cleavage with aqueous or alcoholic acids)
2. the phthalimido protective group (aminolysis with primary amines in aqueous or anhydrous alcohols as solvents)

Reactivity and selectivity, in particular diastereoselectivity, of both the intramolecular and the intermolecular Diels-Alder reaction are influenced by the nature of the diene and of the dienophile (e.g. nature and number of activating groups, nature and number of additional substituents, cis or trans configuration at the double bond) and by the mode of carrying out the reaction (intramolecular or intermolecular) and by the nature of the protective group (P, $P^1$, $P^2$).

The Diels-Alder and cyclisation reactions to be carried out within the scope of the process according to the invention can be illustrated, for example, by the formula diagrams below:

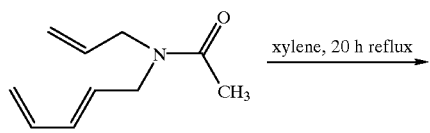

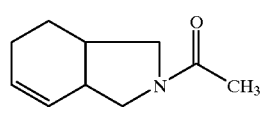

cis:trans = 1:1

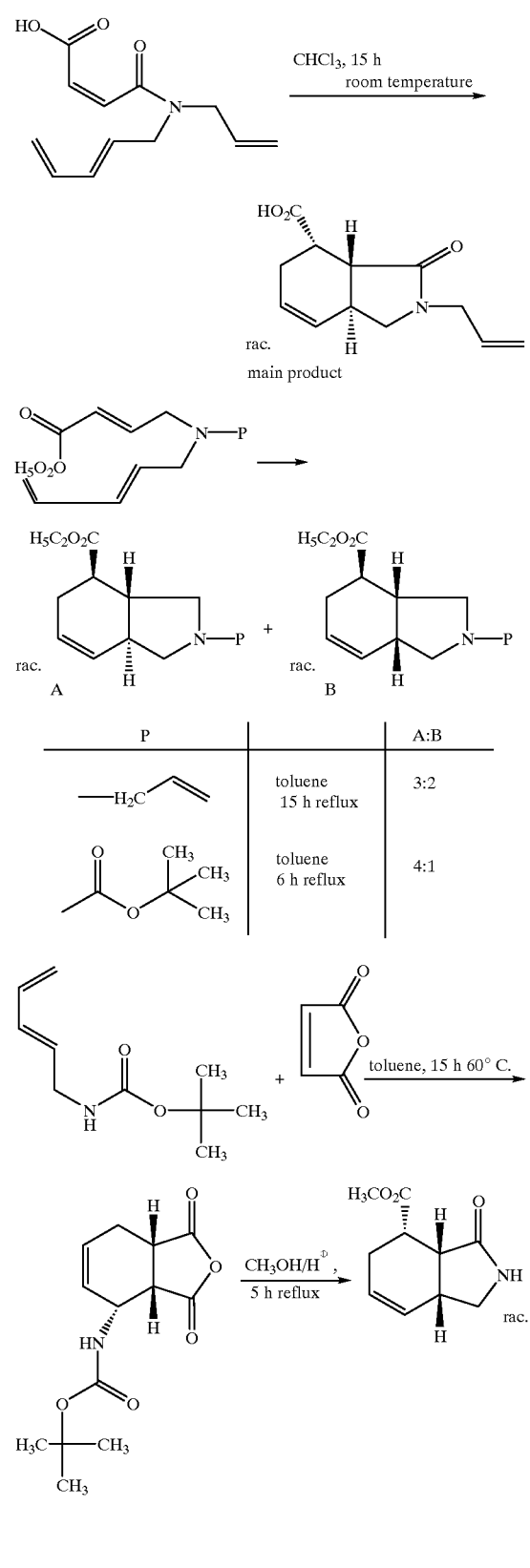

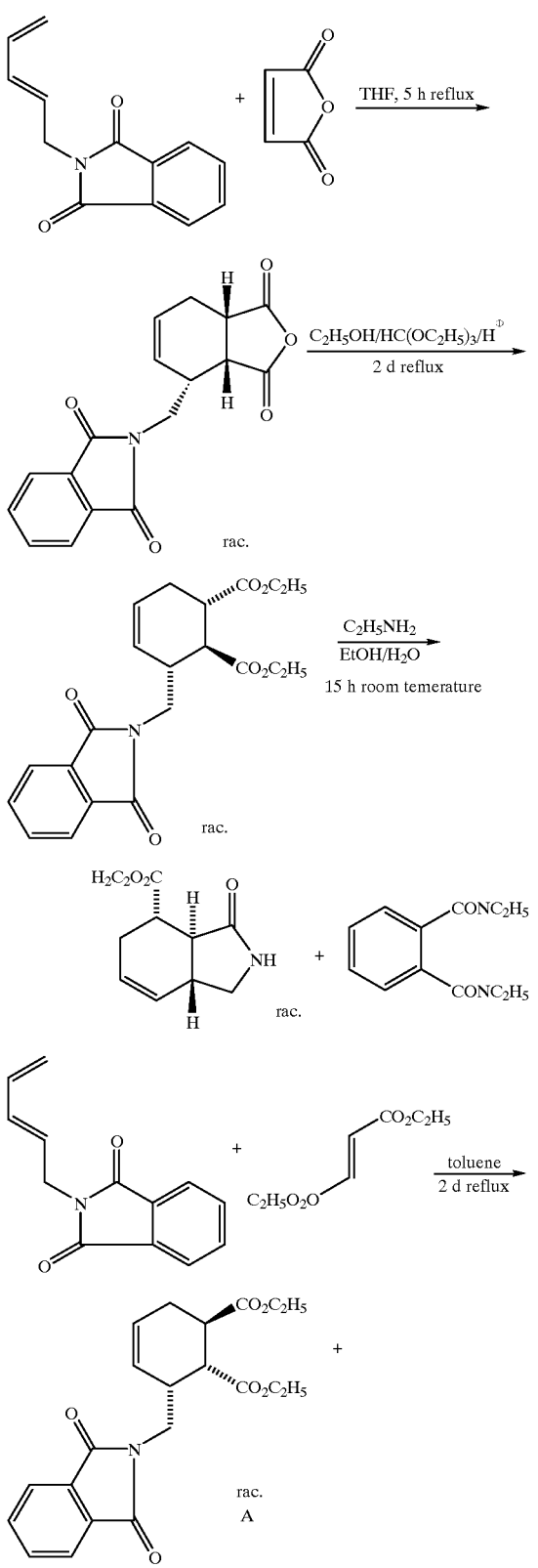
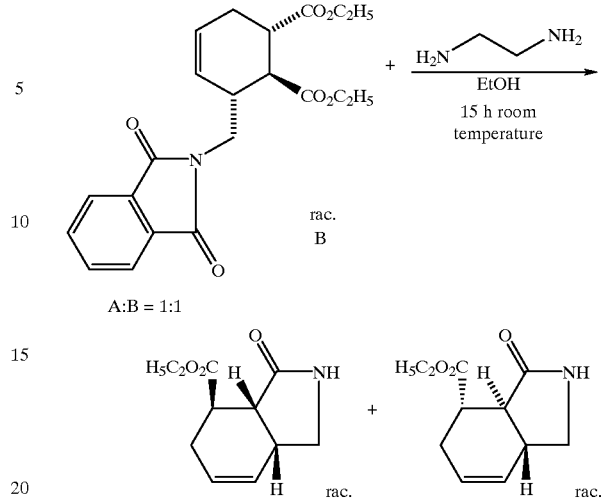

All inert organic solvents are suitable as diluents for the Diels-Alder reaction. These preferably include ethers, such as diisopropyl ether, di-n-butyl ether, dimethoxyethane, tetrahydrofuran and anisole, hydrocarbons, such as, e.g., hexane, methylcyclohexane, toluene, xylene and mesitylene, and halogenated hydrocarbons, such as, e.g., chloroform, 1,2-dichloroethane and chlorobenzene. However, the Diels-Alder reaction can also be carried out without solvents.

The reaction temperatures can be varied over a relatively wide range. In general, temperatures of between about $-20°$ C. and $+200°$ C., preferably of between $-20°$ C. and $+150°$ C., are employed. The Diels-Alder reaction is normally carried out under atmospheric pressure. However, to accelerate the reaction, pressures up to 1.5 GPa can also be employed.

The further reaction of the compounds of the formula (7) to give the compounds of the formula (8) takes place as described in the examples or according to known methods of organic chemistry.

In order to arrive-at the compounds of the formula (III) starting from the compounds of the formula (3), (4) or (8), further reactions are necessary.

Those which may be mentioned, by way of example, are the hydrolysis of an ester to the carboxylic acid, the reduction of carbonyl groups, for example of esters, to aldehydes or alcohols, or of lactam groups to the pyrrolidines, the conversion of a hydroxyl function into an amino function, the conversion of a carboxyl function, or of one of its derivatives, into an amine function with degradation by one carbon atom, the reductive amination of an aldehyde with an amine function present in the molecule, the reductive amination of an aldehyde function present in the molecule with an amine, the introduction of protective groups, and the elimination of the protective group on the pyrrolidine nitrogen in such a way that further protective groups which may be present in the molecule are preserved.

These reactions take place as described in the examples or according to methods which are customary in organic chemistry.

The further reaction of the compounds of the formula (3), (4) or (8) to give the compounds of the formula (III) can be illustrated, for example, by the formula diagrams below:

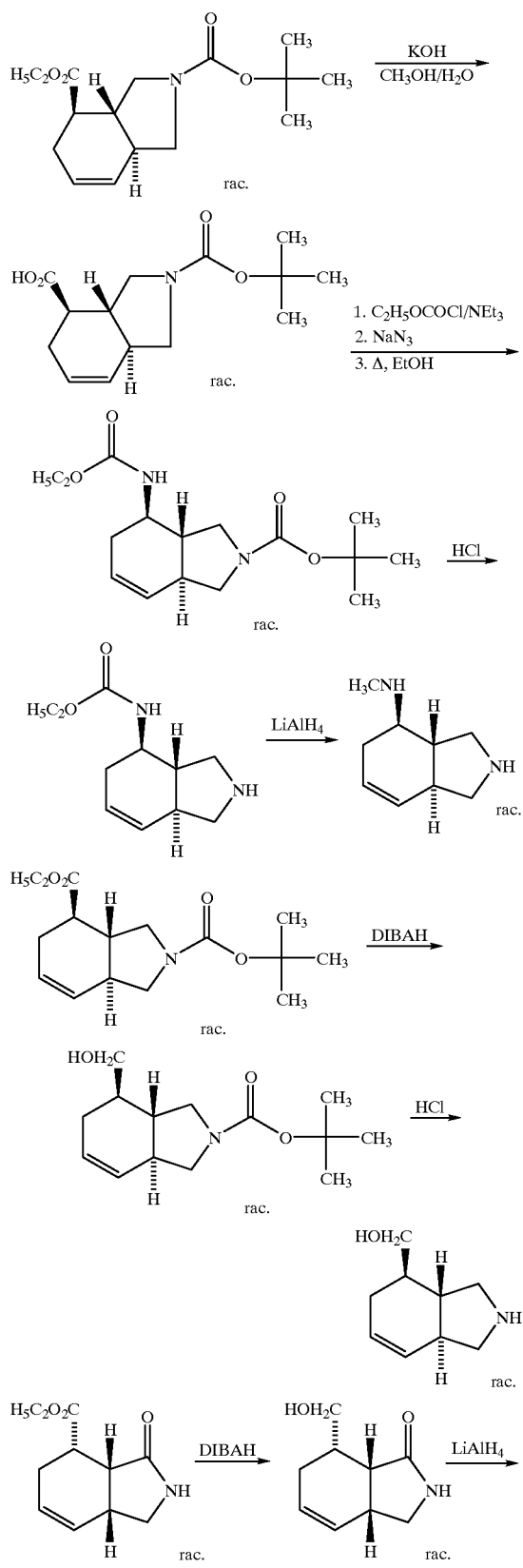

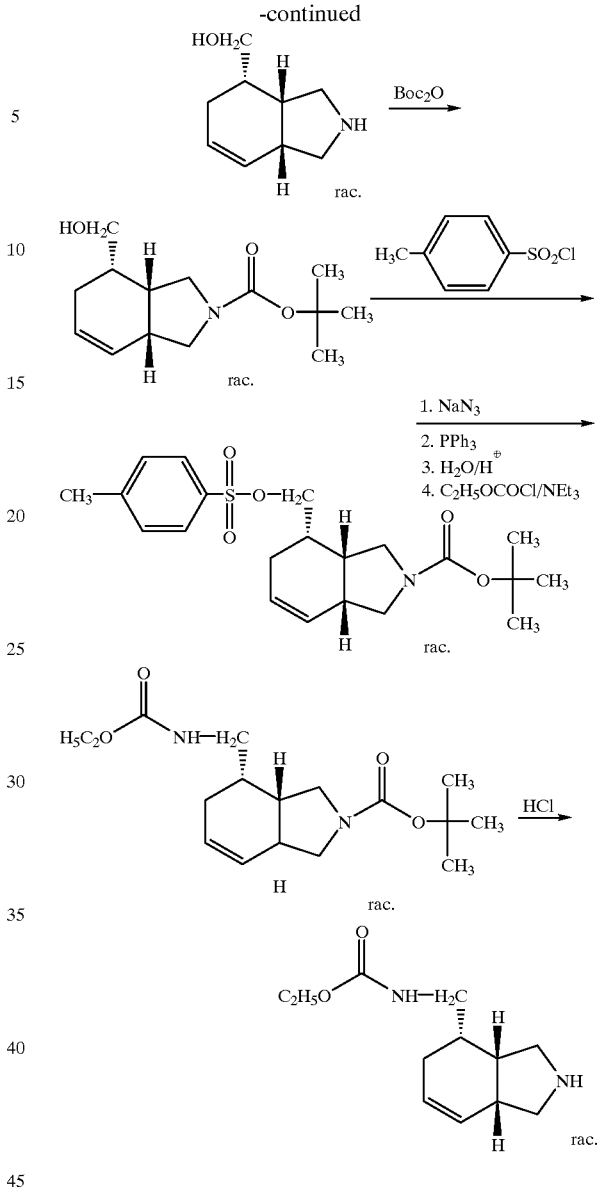

Most of the starting compounds of the formula (1), (2), (5) and (6) are known or can be prepared according to known methods of organic chemistry.

Examples which may be mentioned of compounds of the formula (III), which may be employed either as racemates or as enantiomerically or diastereomerically pure compounds, are:

8-Azabicyclo[4.3.0]non-2-ene
Ethyl 8-azabicyclo[4.3.0]non-4-ene-2-carboxylate
2-Hydroxymethyl-8-azabicyclo[4.3.0]non-4-ene
2-Amino-8-azabicyclo[4.3.0]non-4-ene
2-Ethyloxycarbonylamino-8-azabicyclo[4.3.0]non-4-ene
2-tert-Butyloxycarbonylamino-8-azabicyclo[4.3.0]non-4-ene
2-Benzyloxycarbonylamino-8-azabicyclo[4.3.0]non-4-ene
2-Allyloxycarbonylaminomethyl-8-azabicyclo[4.3.0]non-4-ene
2-Aminomethyl-8-azabicyclo[4.3.0]non-4-ene
2-Ethyloxycarbonylaminomethyl-8-azabicyclo[4.3.0]non-4-ene
2-tert-Butyloxycarbonylaminomethyl-8-azabicyclo[4.3.0]non-4-ene 2-Methylamino-8-azabicyclo[4.3.0]non-4-ene
2-Ethylamino-8-azabicyclo[4.3.0]non-4-ene
2-Cyclopropylamino-8-azabicyclo[4.3.0]non-4-ene
2-Dimethylamino-8-azabicyclo[4.3.0]non-4-ene
2-[(2-Hydroxyethyl)-amino]-8-azabicyclo[4.3.0]non-4-ene
2-Amino-1-methyl-8-azabicyclo[4.3.0]non-4-ene
2-Amino-2-methyl-8-azabicyclo[4.3.0]non-4-ene
2-Amino-3-methyl-8-azabicyclo[4.3.0]non-4 -ene
2-Ethyloxycarbonylamino-3-methyl-8-azabicyclo[4.3.0]
  non-4-ene
2-tert-Butyloxycarbonylamino-3-methyl-8-azabicyclo
  [4.3.0]non-4 -ene
2-Benzyloxycarbonylamino-3-methyl-8-azabicyclo[4.3.0]
  non-4-ene
2-Allyloxycarbonylaminomethyl-3-methyl-8-azabicyclo
  [4.3.0]non-4-ene
2-Amino-4-methyl-8-azabicyclo[4.3.0]non-4-ene
2-Amino-5-methyl-8-azabicyclo[4.3.0]non-4-ene
2-Amino-6-methyl-8-azabicyclo[4.3.0]non-4-ene
2-Amino-7-methyl-8-azabicyclo[4.3.0]non-4-ene
2-Amino-9-methyl-8-azabicyclo[4.3.0]non-4-ene
6-Amino-10-oxa-3-azatricyclo[5.2.1.0$^{1.5}$]dec-8-ene
6-Ethyloxycarbonylamino-10-oxa-3-azatricyclo[5.2.1.0$^{1.5}$]
  dec-8-ene
6-tert-Butyloxycarbonylamino-10-oxa-3-azatricyclo
  [5.2.1.0$^{1.5}$]dec-8-ene
6-Aminomethyl-10-oxa-3-azatricyclo[5.2.1.0$^{1.5}$]dec-8-ene
6-Ethyloxycarbonylaminomethyl-10-oxa-3-azatricyclo
  [5.2.1.0$^{1.5}$]dec-8-ene
6-tert-Butyloxycarbonylaminomethyl-10-oxa-3-azatricyclo
  [5.2.1.0$^{1.5}$]dec-8-ene
6-Amino-3-azatricyclo[5.2.1.0$^{1.5}$]dec-8-ene
6-Amino-3-azatricyclo[5.2.2.0$^{1.5}$]undec-8-ene.

Besides the active compounds mentioned in the examples, the active compounds listed in the table below, which compounds may be present either as racemates or as enantiomerically or diastereomerically pure compounds, can also be prepared:

| Z | R$^5$ | R$^4$ | A | R$^1$ | R$^2$ | R$^3$ |
|---|---|---|---|---|---|---|
| (NH$_2$ substituent) | F | H | CF | cyclopropyl | H | OH |
| (CH$_3$—NH substituent) | " | " | " | " | " | " |
| (H$_5$C$_2$—NH substituent) | " | " | " | " | " | " |
| (cyclopropyl-NH substituent) | " | " | " | " | " | " |
| ((CH$_3$)$_2$N substituent) | F | H | CF | cyclopropyl | H | OH |

-continued
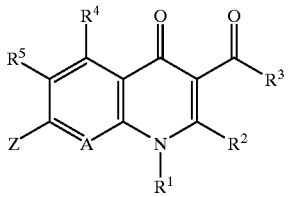
| Z | R⁵ | R⁴ | A | R¹ | R² | R³ |
|---|---|---|---|---|---|---|
| 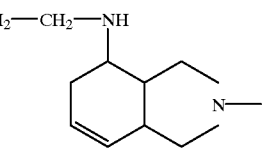 | " | " | " | " | " | " |
| 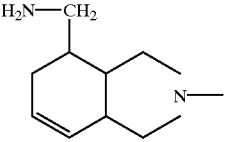 | " | " | " | " | " | " |
| 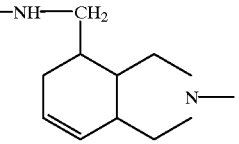 | " | " | " | " | " | " |
| 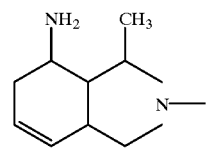 | " | " | " | " | " | " |
| 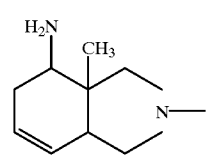 | " | " | " | " | " | " |
| 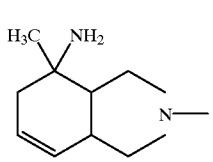 | " | " | " | " | " | " |
| 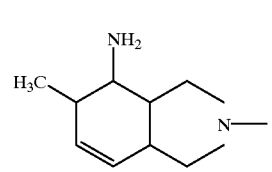 | F | H | CF |  | H | OH |
| 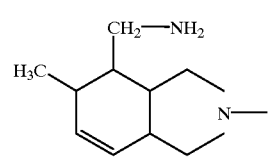 | " | " | " | " | " | " |

-continued
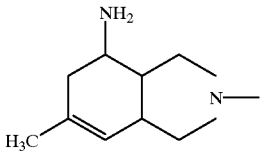
| Z | R⁵ | R⁴ | A | R¹ | R² | R³ |
|---|----|----|---|----|----|----|
| 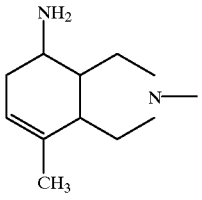 | " | " | " | " | " | " |
| 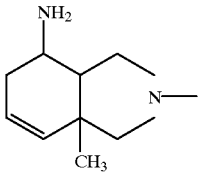 | " | " | " | " | " | " |
| 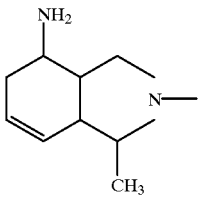 | " | " | " | " | " | " |
| 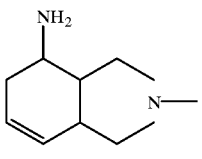 | " | " | " | " | " | " |
|  | H | H | CF | 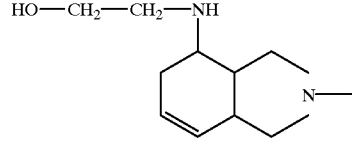 | H | OH |
| 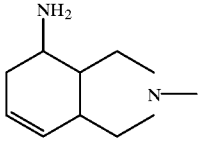 | " | " | " | " | " | " |
|  | Cl | " | " | " | " | " |

-continued
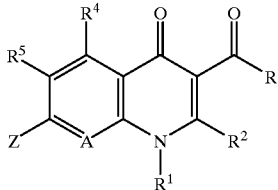
| Z | R⁵ | R⁴ | A | R¹ | R² | R³ |
|---|---|---|---|---|---|---|
| 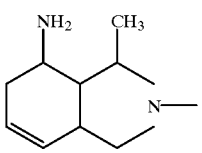 | " | " | " | " | " | " |
| 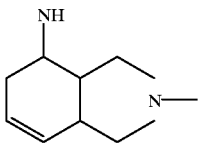 | F | NH² | " | " | " | " |
| 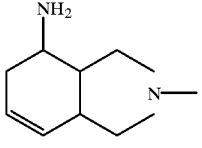 | H | NH₂ | " | " | " | " |
| 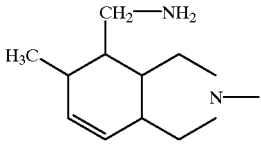 | H | NH₂ | " | " | " | " |
| 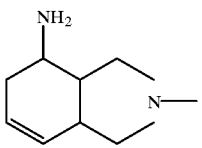 | F | CH₃ | CF |  | H | OH |
| 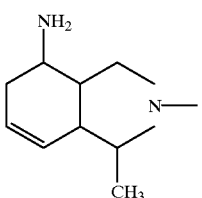 | " | " | " | " | " | " |
| 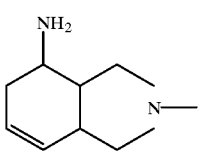 | " | Cl | CCl | " | " | " |
| 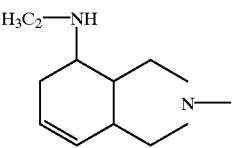 | F | H | CH | " | " | " |

-continued
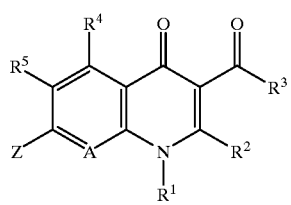
| Z | R5 | R4 | A | R1 | R2 | R3 |
|---|----|----|---|----|----|----|
| 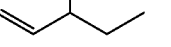 NH₂ (cyclohexenyl-CH₂-N(CH₃)-CH₂-) | H | H | CCl | " | " | " |
| " | F | " | N | " | " | " |
| " | " | " | OCH³ | " | " | " |
| " | " | " | CF | 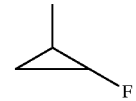 cyclopropyl-F | " | " |
|  NH₂ | F | H | CCl | 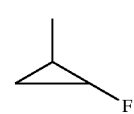 cyclopropyl-F | H | OH |
| " | " | " | CH | " | " | " |
| " | " | " | N | " | " | " |
| 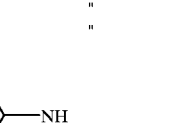 iPrNH | H | NH₂ | CCl | " | " | " |
| 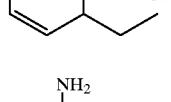 NH₂, H₂C- | F | H | N | " | " | " |
| 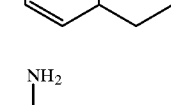 NH₂ | F | H | N |  C(CH₃)₃ | " | " |
| 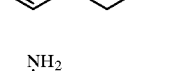 NH₂ | F | H | N |  2,4-difluorophenyl | " | " |

-continued
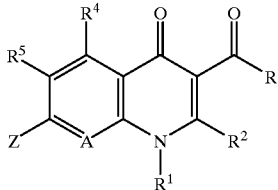
| Z | R⁵ | R⁴ | A | R¹ | R² | R³ |
|---|----|----|---|----|----|----|
| 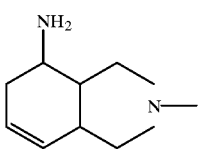 | F | H | CCl | $C_2H_5$ | " | " |
|  | F | H | N | $C_2H_5$ | H | OH |
| 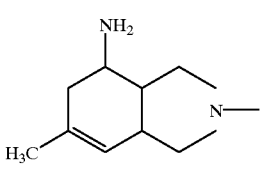 | F | H | CH | $OCH^3$ | " | " |
| " | " | " | " | $NHCH_3$ | " | " |
|  | F | H | 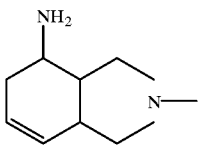 | $CH(CH_3)$ | " | " |
|  | " | " | " | " | " | " |
| 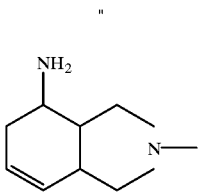 | " | " | " | " | " | " |
|  | " | " | " | 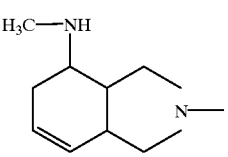 | " | " |
| 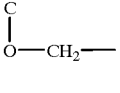 | F | H |  | | | OH |

-continued

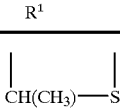

| Z | R⁵ | R⁴ | A | R¹ | R² | R³ |
|---|----|----|----|----|----|----|
| " | " | " | CF | CH(CH₃)—S (cyclic) | | OH |
| 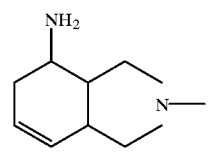 NH₂ | " | H | CF |  (cyclopropyl) " | H | OH |
| 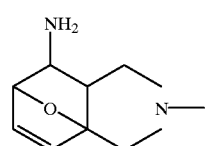 NH₂ (with O) | " | H | CF |  (cyclopropyl) " | H | OH |

The compounds according to the invention have a strong antibiotic effect and exhibit a broad antibacterial spectrum against Gram-positive and Gram-negative organisms, in particular against enterobacteria; especially including those which are resistant towards various antibiotics, such as, e.g., penicillins, cephalosporins, aminoglycosides, sulphonamides, tetracyclines and other quinolones. The compounds according to the invention are distinguished by good tolerability.

These valuable properties permit their use as chemotherapeutic active compounds in medicine and as compounds for preserving inorganic and organic materials, in particular organic materials of every kind, e.g. polymers, lubricants, paints, fibres, leather, paper and wood, foodstuffs and water.

The compounds according to the invention are effective against a very broad spectrum of microorganisms. Using them, Gram-negative and Gram-positive bacteria and bacteria-like microorganisms can be controlled, and the diseases caused by these pathogens prevented, ameliorated and/or cured.

The compounds according to the invention are distinguished by an enhanced effect on resting and resistant organisms. In the case of resting bacteria, that is bacteria which do not exhibit any demonstrable growth, the compounds have an effect at concentrations which are well below those of previously known substances. This relates not only to the quantity to be employed but also to the speed of killing. It was possible to observe such results in the case of Gram-positive and Gram-negative bacteria, in particular in the case of *Staphylococcus aureus, Pseudomonas aeruginosa, Enterococcus faecalis* and *Escherichia coli*.

The compounds according to the invention also demonstrate surprising increases in effect against bacteria which are categorised as being less sensitive towards comparable substances, in particular resistant *Staphylococcus aureus, Escherichia coli, Pseudomonas aeruginosa* and *Enterococcus faecalis*.

The compounds according to the invention are particularly effective against bacteria and bacteria-like microorganisms. They are therefore particularly suitable for the prophylaxis and chemotherapy of local and systemic infections in human and veterinary medicine which are caused by these pathogens.

In addition, the compounds are suitable for combating protozoiases and helminthiases.

Over and above that, the compounds according to the invention are suitable for treating oncoses.

The compounds according to the invention may be used in various pharmaceutical preparations. Preferred pharmaceutical preparations which may be mentioned are tablets, coated tablets, capsules, pills, granules, suppositories, solutions, suspensions and emulsions, pastes, ointments, gels, creams, lotions, powders and sprays.

The minimum inhibitory concentrations (MIC) were determined by means of serial dilution methods on Iso-Sensitest agar (Oxoid). For each substance to be tested, a series of agar plates was prepared which contained concentrations of the active compound which decreased by a double dilution on each occasion. The agar plates were inoculated with a Multipoint inoculator (Denley). For the inoculation, overnight cultures of the pathogens were used which had previously been diluted so that each inoculation spot contained about $10^4$ colony-forming particles. The inoculated agar plates were incubated at 37° C., and the organism growth was recorded after about 20 hours. The MIC value (μg/ml) indicates the lowest concentration of active compound at which no growth could be detected with the naked eye.

The MIC values of some of the compounds according to the 20 invention are listed in the table below in comparison with 7-(4-amino-1,3-dihydro-isoindol-2-yl)-1-cyclopropyl-6,8-difluoro-1,4-dihydro-4-oxo-3-quinolinecarboxylic acid (EP-A-343 560, Example 2).

TABLE

MIC values (μg/ml)

| | \* | 4 | 6 | 12 | 14 | 19 | 22 |
|---|---|---|---|---|---|---|---|
| *E. coli* Neumann | 0.5 | 0.0078 | ≦0.015 | 0.0039 | 0.03 | ≦0.015 | 0.03 |
| *Klebsiella* sp. 8085 | 4 | 0.015 | 0.03 | 0.015 | 0.125 | 0.03 | 0.06 |
| *Enterobacter cloacae* 2427 | — | 0.015 | 0.06 | 0.015 | 0.125 | 0.03 | 0.125 |
| *Morganella morg.* 932 | 1 | 0.015 | — | 0.015 | 0.125 | 0.03 | 0.125 |
| *Providencia* sp. 12012 | 1 | 0.015 | 0.03 | 0.015 | 0.125 | ≦0.015 | 0.125 |
| *Micrococcus luteus* 9341 | — | 0.015 | 0.06 | 0.015 | 0.125 | 0.06 | 0.125 |
| *Staphylococcus aureus* ICB 25701 | — | 0.03 | 0.125 | 0.015 | 0.25 | 0.03 | 0.125 |
| *Staphylococcus aureus* 1756 | 0.03 | 0.0039 | ≦0.015 | ≦0.0019 | 0.0078 | ≦0.015 | ≦0.015 |
| *Enterococcus faecalis* 27 101 | 0.5 | 0.15 | 0.03 | 0.0078 | 0.03 | ≦0.015 | 0.03 |
| *Pseudomonas aeruginosa* Walter | >128 | 0.25 | 0.5 | 0.25 | 1 | 1 | 2 |

\*: Reference compound: 7-(4-amino-1,3-dihydro-isoindol-2-yl)-1-cyclopropyl-6,8-difluoro-1,4-dihydro-4-oxo-3-quinolinecarboxylic acid (EP-A-343 560, Example 2)

Preparation of the intermediates:

EXAMPLE A

8-Azabicyclo[4.3.0]non-2-ene

A.1. (E)-1-Bromo-2,4-pentadiene

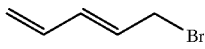

Initially introduce 84 g (1.0 mol) of 1,4-pentadien-3-ol at 0° C. While stirring, add 150 ml (≈1.3 mol) of 48% strength aqueous hydrobromic acid dropwise in such a way that the internal temperature does not exceed 5° C. After addition is complete, stir at room temperature for a further 1 h. The organic phase is separated off and is subjected to further reaction without purification.

Yield: 107–129 g (73–88% of theory)

A.2. (E)-1-(2-Propenylamino)-2,4-pentadiene

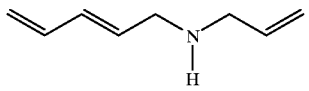

Initially introduce 228 g (4.0 mol) of 1-amino-2-propene. While stirring, add 58.8 g (0.4 mol) of (E)-1-bromo-2,4-pentadiene (title compound from Example A.1.) dropwise. Keep the internal temperature within the range of 20–30° C. by cooling. Stir at room temperature for 5 h. Concentrate the mixture under 150 mbar. Add 20 g (0.5 mol) of sodium hydroxide dissolved in 200 ml of water, extract twice with 100 ml of methylene chloride on each occasion, dry with sodium sulphate, add 0.1 g of 4-hydroxyanisole, concentrate and distil under 40 mbar. 10–20 ppm of 4-hydroxyanisole are added to the distillate for stabilisation.

Yield: 33–35 g (67–72% of theory)

Boiling point: 77–82° C. under 40 mbar $^1$H-NMR (CDCl$_3$): δ=6.07–6.48 (m, 2H); 5.64–6.07 (m, 2H); 5.00–5.27 (m, 4H); 3.19–3.36 ppm (m, 4H).

A.3. N-[(E)-2,4-Pentadienyl]-N-(2-propenyl)-acetamide

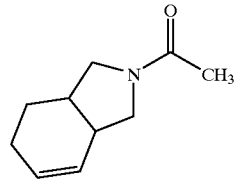

Initially introduce 24.6 g (0.2 mol) of (E)-1-(2-propenylamino)-2,4-pentadiene (title compound from Example A.2.), add 22.4 g of acetic anhydride dropwise, and stir at room temperature overnight. Concentrate and subject to further reaction as the crude product.

A.4. 8-Acetyl-8-azabicyclo[4.3.0]non-2-ene

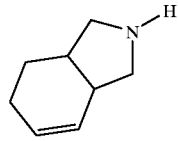

Dissolve 33.1 g (0.2 mol) of N-[(E)-2,4-pentadienyl]-N-(2-propenyl)-acetamide (title compound from Example A.3.) in 200 ml of xylene, pass a powerful stream of nitrogen through for 15 min, add 0.1 g of 4-hydroxyanisole, and then heat to reflux overnight. Concentrate, distil under high vacuum.

Yield: 23.1 g (70% of theory based on the title compound from Example A.2.)

Boiling point: 88–93° C. under 0.05 mbar

A.5. 8-Azabicyclo[4.3.0]non-2-ene

Heat 16.5 g (0.1 mol) of 8-acetyl-8-azabicyclo[4.3.0]non-2-ene (title compound from Example A.4.) to reflux for 3 h in a mixture consisting of 100 ml of 45% strength sodium hydroxide solution, 50 ml of water and 100 ml of 1,2-ethanediol. After cooling, extract four times with 50 ml of diethyl ether on each occasion. Dry the combined organic phases with sodium sulphate, and distil under high vacuum.

Yield: 6.6 g (54% of theory)

Boiling point: 36–44° C. under 0.35 mbar $^1$H-NMR (CDCl$_3$): δ=5.79 (m, 1H); 5.74 (m, 1H); 3.02–3.17 (m, 2H); 2.47–2.72 (m, 2H); 2.06–2.30 (m, 2H); 1.91–2.06 (m, 2H); 1.68 (m, 1H); 1.45 ppm (m, 1H).

EXAMPLE B

Ethyl (1RS,2RS,6SR)-8-azabicyclo[4.3.0]non-4-ene-2-carboxylate (diastereomer A) and ethyl (1RS,2RS,6RS)-8-azabicyclo[4.3.0]non-4-ene-2-carboxylate (diastereomer B)

B.1. N-[(E)-2,4-Pentadienyl]-phthalinmde

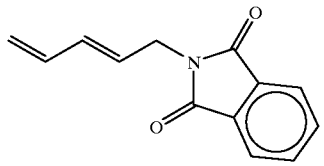

Initially introduce 185 g (1.0 mol) of potassium phthalimide in 800 ml of DMF. While stirring, add 147 g (1.0 mol) of (E)-1-bromo-2,4-pentadiene (title compound from Example A.1.) dropwise, and during this process keep the internal temperature below 30° C. by cooling. Stir at room temperature overnight. Subsequently, pour the mixture, while stirring, into 1.6 l of ice water, filter off the precipitate with suction, wash with water, and dry at room temperature until constant weight has been reached.

Yield: 177–200 g (83–94% of theory)

Melting point: 118–121° C. (sample recrystallised from ethanol)

$^1$H-NMR (CDCl$_3$): δ=7.85 and 7.72 (m, 4H, aryl-H); 6.2–6.4 (m, 2H, H on C-3 and C-4); 5.75 (dt, 1H, H on C-2, J=14 and 6 Hz); 5.20 (d, 1H, H$_a$ on C-5, J=15 Hz); 5.10 (d, 1H, H$_b$ on C-5, J=8 Hz); 4.33 ppm (d, 2H, H on C-1, J=6 Hz).

B.2. (E)-1-Amino-2,4-pentadiene

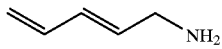

400 g of bis-(2-aminoethyl)-amine and 213 g (1.0 mol) of N-[(E)-2,4-pentadienyl]-phthalimide (title compound from Example B.1.) are initially introduced into a 2 l distillation apparatus having a 10 cm Vigreux column, and heated to boiling under 60 mbar. Under 60 mbar, the product distils in the range from 45–60° C. 10–20 ppm of 4-hydroxyanisole are added to the distillate for stabilisation.

Yield: 71–80 g (86–96% of theory)

B.3. Ethyl (E)-4-[(E)-2,4-pentadienylamino]-2-butenoate

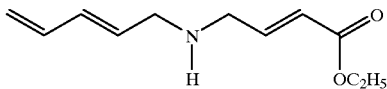

Initially introduce 41.6 g (0.5 mol) of (E)-1-amino-2,4-pentadiene (title compound from Example B.2.) and 50.6 g (0.5 mol) of triethylamine in 250 ml of THF at 0° C., and add 96.5 g (0.5 mol) of ethyl (E)-4-bromo-2-butenoate dissolved in 250 ml of THF dropwise. Keep the internal temperature below 5° C. by cooling with ice. Stir at 0° C. for 5 h, and then subsequently at room temperature overnight. Add 500 ml of MTBE, and then 500 ml of 1M sodium hydroxide solution, shake, phase separation, extract aqueous phase once with 100 ml of MTBE, dry the combined organic phases with sodium sulphate, add 100 ml of toluene and 0.1 g of 4-hydroxyanisole, and concentrate (during which avoid temperatures above 40° C.). Purify the residue by column chromatography on 1 kg of silica gel (63–200 μm) using cyclohexane/acetone 2:1. Before concentrating, add 0.1 g of 4-hydroxyanisole once again, and while concentrating avoid temperatures above 40° C.

Yield: 52.7–58.6 g (54–60% of theory) of a yellowish oil R$_f$=0.24

$^1$H-NMR (CDCl$_3$): δ=6.99 (dt, 1H, J=15 and 5.5 Hz); 6.1–6.45 (m, 2H); 5.98 (d, 1H, J=15 Hz); 5.75 (dt, 1H, J=15 and 6.5 Hz), 5.18 (d, 1H, J=15 Hz); 5.06 (d, 1H, J=10 Hz); 4.19 (q, 2H); 3.42 (dd, 2H); 3.31 (d, 2H); 1.29 ppm (t, 3H).

B.4. Ethyl (1RS,2RS,6SR)-8-tert-butyloxycarbonyl-8-azabicyclo[4.3.0]non-4-ene-2-carboxylate (diastereomer A) and ethyl (1RS,2RS,6RS)-8-tert-butyloxycarbonyl-8-azabicyclo[4.3.0]non-4-ene-2-carboxylate (diastereomer B)

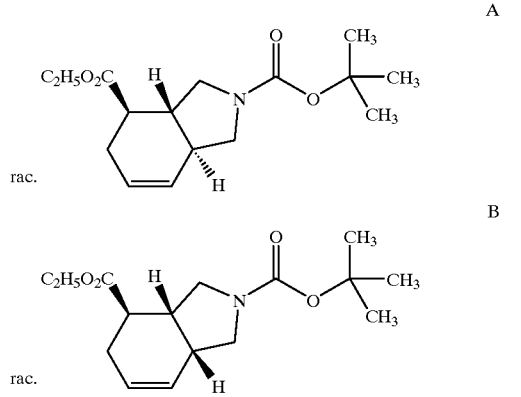

Initially introduce 97.5 g (0.5 mol) of ethyl (E)-4-[(E)-2,4-pentadienylamino]-2-butenoate (title compound from Example B.3.) dissolved in 250 ml of toluene. Add 114.5 g (0.525 mol) of di-tert-butyl dicarbonate dissolved in 250 ml of toluene dropwise, and stir at room temperature overnight. Subsequently, pass through a powerful stream of nitrogen for 15 min, add 0.1 g of 4-hydroxyanisole, and then heat to reflux for 6 h. Concentrate, and purify the residue by column chromatography on 1 kg of silica gel (63–200 μm) using cyclohexane/acetone 8:1.

Yield: 109–134 g (74–91% of theory) of a yellowish oil; mixture consisting of two diastereomers A and B in a ratio A:B 4:1 R$_f$=0.25

$^1$H-NMR (Cl$_2$DC-CDCl$_2$; 80° C.): δ=5.77 (m, 1H(A) and 1H(B)); 5.68 (m, 1H(A) and 1H(B)); 4.14 (m, 2H(A) and 2H(B)); 3.65 (m, 2H(A) and 1H(B)); 3.48 (dd, 1H(B)); 3.27 (dd, 1H(B)); 3.00 (m, 1H(A) and 1H(B)); 2.85 (dd, 1H(A)); 2.76 (m, 1H(B)); 2.60 (m, 1H(A)); 2.25–2.55 (m, 3H(A) and 4H(B)); 1.93 (m, 1H(A)); 1.51 (s, 9H(B)); 1.44 (s, 9H(A)); 1.25 ppm (t, 3H(A) and 3H(B)).

B.5. Ethyl (1RS,2RS,6SR)-8-azabicyclo[4.3.0]non-4-ene-2-carboxylate (diastereomer A) and ethyl (1RS,2RS,6RS)-8-azabicyclo[4.3.0]non-4-ene-2-carboxylate (diastereomer B)

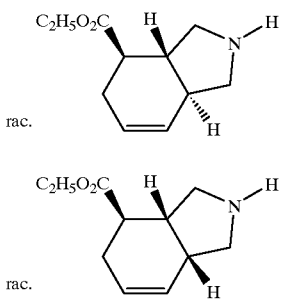

Initially introduce 6.0 g (20 mmol) of the title compound from Example B.4. in 20 ml of dioxane. While cooling, add 20 ml of conc. hydrochloric acid dropwise in such a way that the internal temperature does not exceed 30° C. Once addition is complete, stir for a further 10 min. Add 40 ml of methylene chloride and, while cooling with ice, add 40 ml of 20% strength ice-cooled sodium hydroxide solution dropwise. Separate off the organic phase, extract the aqueous phase once with methylene chloride, dry the combined organic phases with sodium sulphate, and concentrate. Purify 3.0 g of the crude product by column chromatography on 100 g of silica gel (63–200 μm) using cyclohexane/ethanol/17% strength aqueous ammonia (1:2:0.1).

Yield: 0.8 g of diastereomer A and 0.8 g of diastereomer B $R_f$=0.79 title compound from Example B.4. 0.21 diastereomer B 0.11 diastereomer A $^1$H-NMR (CDCl$_3$):

Diastereomer A: δ=5.83 (d, 1H); 5.69 (m, 1H); 4.15 (q, 2H); 3.21–3.38 (m, 2H); 2.52–2.89 (m, 3H); 2.21–2.52 (m, 3H); 1.95 (m, 1H); 1.28 ppm (t, 3H).

Diastereomer B: δ=5.64–5.87 (m, 2H); 4.16 (q, 2H); 3.14–3.33 (m, 2H); 2.82 (dd, 1H); 2.15–2.74 (m, 6H); 1.28 ppm (t, 3H).

EXAMPLE C (1SR,2RS,6SR)-2-Ethyloxycarbonylamino-8-azabicyclo[4.3.0]non-4-ene C.1. (1RS,2RS,6SR)-8-tert-Butyloxycarbonyl-8-azabicyclo-[4.3.0]non-4-ene-2-carboxylic acid

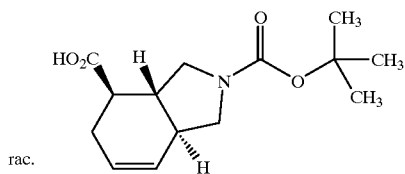

Initially introduce 30.8 g (0.55 mol) of potassium hydroxide dissolved in 500 ml of water. Add 147.7 g (0.5 mol) of the title compound from Example B.4. dissolved in 500 ml of methanol, and stir at 60° C. for 8 h under a nitrogen atmosphere. After cooling, dilute the reaction solution with 500 ml of water and, while stirring, pour in 125 ml of acetic acid slowly. After addition is complete, allow to stand for 30 min in an ice bath, and then filter off the precipitate with suction, wash with water, and dry at 50° C. to constant weight.

Yield: 84–98 g (63–73% of theory)

Melting point: 174–176° C. (sample recrystallised from isopropanol/water 1:1.)

$^1$H-NMR (Cl$_2$DC-CDCl$_2$; 80° C.): δ=5.83 (m, 1H, H on C-5); 5.74 (m, 1H, H on C-4); 3.65–3.80 (m, 2H, Hz on C-7 and H$_a$ on C-9); 3.09 (dd, 1H, H$_b$ on C-9); 2.92 (dd, 1H, H$_b$ on C-7); 2.70 (m, 1H, H on C-2); 2.35–2.60 (m, 3H, H$_a$ and H$_b$ on C-3 and H on C-6); 2.01 (m, 1H, H on C-1); 1.5 ppm (s, 9H).

C.2. (1SR,2RS,6SR)-8-tert-Butyloxycarbonyl-2-ethyloxycarbonylamino-8-azabicyclo[4.3.0]non-4-ene

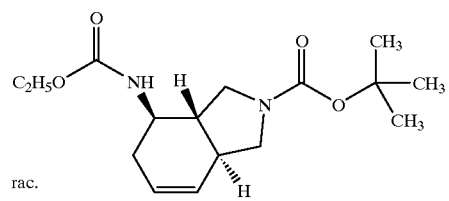

Initially introduce 53.3 g (0.2 mol) of the title compound from Example C.1. and 22.2 g (0.22 mol) of triethylamine dissolved in 200 ml of anhydrous THF. While cooling with an ice/sodium chloride mixture, add 22.8 g (0.21 mol) of ethyl chloroformate dissolved in 40 ml of THF dropwise in such a way that the internal temperature does not exceed –10° C. After addition is complete, stir for a further 1 h at a low temperature. Subsequently, while stirring vigorously, add an ice-cooled solution of 15.6 g (0.24 mol) of sodium azide in 50 ml of water dropwise in such a way that the internal temperature does not exceed –10° C. After addition is complete, stir for a further 30 min at a low temperature. Subsequently add, in succession, 300 ml of water and 400 ml of toluene.

Separate off the organic phase, dry with sodium sulphate, and concentrate, under 15 mbar, down to half of the original volume (bath temperature below 25° C.). Addition of 100 ml of ethanol, heat up slowly while stirring (at the rate allowed by the evolution of nitrogen) and, after the nitrogen evolution is complete, boil to reflux for 4 h. Concentrate, and recrystallise the crude product from methanol/water 85:15, and dry at 50° C. to constant weight.

Yield: 24.2–28.5 g (39–46% of theory) of the title compound

Melting point: 120–122° C.

$^1$H-NMR (CDCl$_3$): δ=5.78 and 5.73 (2d, 1H, H on C-5); 5.64 (m, 1H, H on C-4); 4.59 br. s, 1H, NH); 4.12 (m, 2H, ethoxy CH$_2$); 3.90 (m, 1H, H on C-2); 3.74 and 3.67 (2m, 1H, H$_a$ on C-7); 3.67 and 3.56 (2m, 1H, H$_a$ on C-9); 3.12 (m, 1H, H$_b$ on C-9); 2.92 (m, 1H, H$_b$ on C-7); 2.67 (m, 1, H$_a$ on C-3); 2.49 (m, 1H, H on C-6); 1.95 (m, 1H, H$_b$ on C-3); 1.83 (m, 1H, H on C-1); 1.46 (s, 9H); 1.24 ppm (m, 3H, ethoxy CH$_3$).

Adjust the aqueous phase to a pH of 2–3 by the addition of 10% strength hydrochloric acid, allow to stand for 30 min in an ice bath, and filter off the precipitate with suction, wash with water, and dry at 50° C. to constant weight.

Yield: 16.0–19.2 g (30–36% of the title compound from Example C.1.) (recovered starting compound)

C.3. (1SR,2RS,6SR)-2-Ethyloxycarbonylamino-8-azabicyclo[4.3.0]non-4-ene

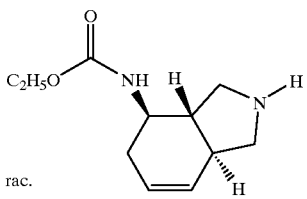

Initially introduce 31.0 g (0.1 mol) of the title compound from Example C.2. in 100 ml of a mixture consisting of methanol/water (1:1) (suspension). Allow 100 ml of conc. hydrochloric acid to run in rapidly (slightly exothermic up to about 40° C. (a homogeneous solution is obtained)), and then stir until the end of the gas evolution (about 10 min). Add 200 ml of ice water, and then add, while stirring and while cooling with ice, 70 ml of 45% strength sodium hydroxide solution dropwise. Extract four times with 50 ml of methylene chloride on each occasion, dry the combined organic phases with sodium sulphate, concentrate, and strip off solvent residues under high vacuum. The substance solidifies while being concentrated.

Yield: 13.7–16.6 g (65–79% of theory) of a brown-pink-coloured, amorphous solid $R_f$=0.81 title compound from Example C.2. 0.11 title compound
Methylene chloride/methanol/17% strength aqueous ammonia (15:4:0.5)

$^1$H-NMR (CDCl$_3$): δ=5.78 (d, 1H, H on C-5); 5.63 (m, 1H, H on C-4); 4.94 (br. d, 1H, NH); 4.10 (m, 2H, ethoxy CH$_2$); 3.88 (m, 1H, H on C-2); 3.28 (m, 1H, H$_a$ on C-7); 3.19 (m, 1H, H$_a$ on C-9); 2.84 (m, 1H, H$_b$ on C-9); 2.57–2.62 (m, 2H, H$_a$ on C-3 and H$_b$ on C-7); 2.43 (m, 1H, H on C-6); 1.95 (m, 1H, H$_b$ on C-3); 1.79 (m, 1H, H on C-1); 1.23 ppm (m, 3H, ethoxy CH$_3$).

EXAMPLE D (1SR,2RS,6SR)-2-Methylamino-8-azabicyclo[4.3.0]non-4-ene

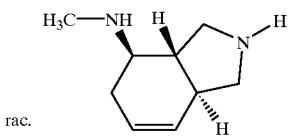

Initially introduce 1.9 g (50 mmol) of lithium aluminium hydride in 25 ml of anhydrous diethyl ether in an atmosphere of nitrogen. Add 5.25 g (25 mmol) of the title compound from Example C.3. dissolved in 50 ml of anhydrous tetrahydrofuran dropwise, and heat to reflux for 3 h. Add a further 0.95 g (25 mmol) of lithium aluminium hydride, and heat once again to reflux for 3 h. While cooling with ice, add water slowly dropwise until a white precipitate has formed. Filter off the precipitate with suction, and extract twice by boiling with 100 ml of ethanol on each occasion. Combine the ethanol extracts with the mother liquor of the reaction, add 50 ml of toluene, concentrate, and strip off the solvent residues under high vacuum.

Yield: 1.95 g (77% of theory) of amorphous solid $R_f$=0.11
Methylene chloride/methanol/17% strength aqueous ammonia (2:4:1)

$^1$H-NMR (CDCl$_3$): δ=5.77 (d, 1H, H on C-5); 5.67 (m, 1H, E on C-4); 3.33 (dd, 1H, H$_a$ on C-7); 3.26 (dd, 1H, H$_a$ on C-9); 2.73–2.82 and 2.54–2.63 (2m, 4H, H on C-2, H$_a$ on C-3, H$_b$ on C-7 and H$_b$ on C-9); 2.41 (s, 3H, CH$_3$N); 2.34 (m, 1H, H on C-6); 1.90 (m, 1H, H$_b$ on C-3); 1.70 ppm (m, 1H, H on C-1).

EXAMPLE E (1RS,2RS,6SR)-2-Hydroxymethyl-8-azabicyclo[4.3.0]non-4-ene

E.1. (1RS,2RS,6SR)-8-tert-Butyloxycarbonyl-2-hydroxymethyl-8-azabicyclo[4.3.0]non-4-ene (diastereomer A) and
(1RS,2RS,6RS-8-tert-butyloxycarbonyl-2-hydroxymethyl-8-azabicyclo[4.3.0]non-4-ene (diastereomer B)

A
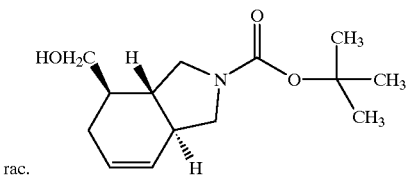

B
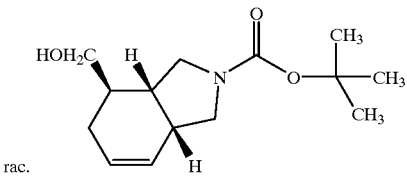

Initially introduce 29.5 g (0.1 mol) of the title compound from Example B.4. in 200 ml of anhydrous 1,2-dimethoxyethane in an atmosphere of nitrogen. Add 150 ml of a 1.5 M DIBAH solution in toluene (0.225 mol) dropwise at an internal temperature <−65° C. After the addition is complete, remove the cooling bath and allow to come to room temperature. Stir at room temperature for a further 2 h.

While stirring vigorously, add 60 ml of methanol dropwise (exothermic reaction); maintain the internal temperature between 35 and 45° C. by cooling with a cold water bath. Subsequently, add 20 ml of 5% strength sodium hydroxide solution dropwise. After addition is complete, stir for a further 10 min. Filter off the precipitate with suction and, while stirring, extract twice by boiling with 150 ml of ethanol on each occasion, combine the ethanol extracts and the reaction solution, concentrate, strip off solvent residues under high vacuum, and purify the residue by column chromatography on 250 g of silica gel (63–200 μm) using cyclohexane/acetone (4:1).

Yield: 12.9–17.7 g (51–70% of theory) of a yellowish oil; mixture of the diastereomers A and B in the ratio 4:1

$R_f$=0.36 title compound from Example B.4. 0.12 title compound A and B

The crude product becomes solid after standing for a lengthy period. A diastereomerically pure sample of the main diastereomer A can be obtained by recrystallising from ether/petroleum ether.

$^1$H-NMR (CDCl$_3$): (diastereomer A) δ=5.67–5.82 (m, 2H, H on C-4 and C-5); 3.50–3.77 (m, 4H, H$_a$ on C-7, H$_a$ on C-9 and hydroxymethyl CH$_2$); 3.02 (dt, 1H, H$_b$ on C-9); 2.85 (m, 1H, H$_b$ on C-7); 2.2–2.4 (m, 3H); 1.87–2.00 (m, 3H); 1.62 (m, 1H, H on C-1); 1.46 ppm (s, 91).

E.2. (1RS,2RS,6SR)-2-Hydroxymethyl-8-azabicyclo[4.3.0]non-4-ene

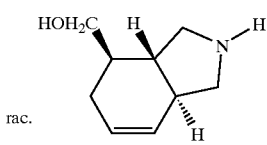

Initially introduce 2.5 g (10 mmol) of the title compound A from Example E.1. in 10 ml of methanol. Allow 10 ml of conc. hydrochloric acid to run in rapidly, and then stir for 30 min. Dilute with water to double the volume and then, while stirring and cooling with ice, add 45% strength sodium hydroxide solution dropwise up to a pH of ≧12. Concentrate, while stirring extract the residue twice by boiling with ethanol, concentrate the ethanol extracts, and strip off solvent residues under high vacuum.

Yield: 2.1 g (product contains NaCl residues) $R_f$=0.20 Methylene chloride/methanol/17% strength aqueous ammonia (2:4:1)

$^1$H-NMR (d$_6$-DMSO): δ=5.76 (d, 1H); 5.62 (d, 1H); 3.47–3.56 (m, 2H, H$_a$ on C-7 and H$_a$ on C-9); 3.32–3.47 (m, 1H, H$_a$ of hydroxymethyl CH$_2$); 3.23–3.32 (m, 1H, H$_b$ of hydroxymethyl CH$_2$); 2.77 (t, 1H, H$_b$ on C-9); 2.64 (t, 1H, H$_b$ on C-7); 2.10–2.24 (m, 2H, H$_a$ on C-3 and H on C-6); 1.77–1.88 (m, 1H, H$_b$ on C-3); 1.69 (m, 1H, H on C-2); 1.40 ppm (m, 1H, H on C-1).

EXAMPLE F (1RS,2RS,6SR)-2-Ethyloxycarbonylaminomethyl-8-azabicyclo[4.3.0]non-4-ene F.1. (1RS,2RS,6SR)-8-tert-Butyloxycarbonyl-2-(4-toluenesulphonyloxymethyl)-8-azabicyclo[4.3.0]non-4-ene (diastereomer A) and
(1RS,2RS,6RS)-8-tert-Butyloxycarbonyl-2-(4-toluenesulphonyloxymethyl)-8-azabicyclo[4.3.0]non-4-ene (diastereomer B)

A

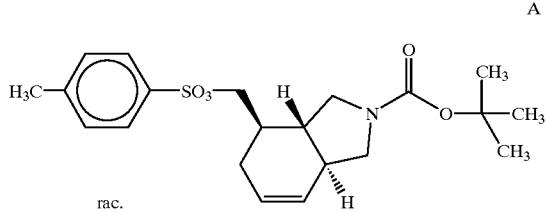

B

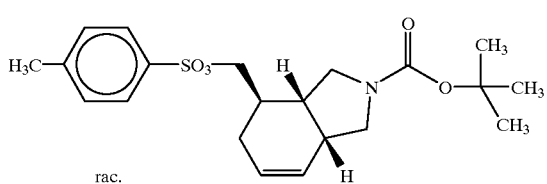

Initially introduce 12.7 g (0.05 mol) of the title compound from Example E.1. (crude mixture of the diastereomers A and B) in 25 ml of anhydrous pyridine, and cool to −15° C. Add 11.0 g (0.0575 mol) of 4-toluenesulphonyl chloride in portions in such a way that the internal temperature does not exceed −5° C. After addition is complete, stir at a temperature of −5 to −15° C. for a further 2 h, and then at room temperature for a further 3 h. Add 5 g of ice, stir for 5 min, add to 50 ml of water, and filter off the precipitate with suction, wash it with water, and dry it at 50° C. to constant weight.

Yield: 14.4–16.3 g (71–80% of theory) pale pink-coloured solid Mixture of the diastereomers A and B A diastereomerically pure sample of the main diastereomer A can be obtained by recrystallisation from methanol.

Melting point: 111–113° C.

$^1$H-NMR (CDCl$_3$): (diastereomer A) δ=7.79 (m, 2H, aryl H); 7.36 (d, 2H, aryl H); 5.74 and 5.78 (2d, 1H, H on C-5); 5.64 (m, 1H, H on C-4); 3.87–3.97 (m, 2H, tosyl OCH$_2$—); 3.59 and 3.67 (2dd, 1H, H$_a$ on C-7); 3.48 (dd, 1H, H$_a$ on C-9); 2.78–2.96 (m, 2H, H$_b$ on C-7 and H$_b$ on C-9); 2.47 (s, 3H, aryl CH$_3$); 2.22–2.36 (m, 2H, H$_a$ on C-3 and H on C-6); 2.06 (m, 1H, H on C-2); 1.80–1.98 (m, 1H, H$_b$ on C-3); 1.59 (m, 1H, H on C-1); 1.45 and 1.47 ppm (2s, 9H).

F.2. (1RS,2RS,6SR)-8-tert-Butyloxycarbonyl-2-ethyloxycarbonylaminomethyl-8-azabicyclo[4.3.0]non-4-ene (diastereomer A) and
(1RS,2RS,6RS)-8-tert-butyloxycarbonyl-2-ethyloxycarbonylaminomethyl-8-azabicyclo[4.3.0]non-4-ene (diastereomer B)

A

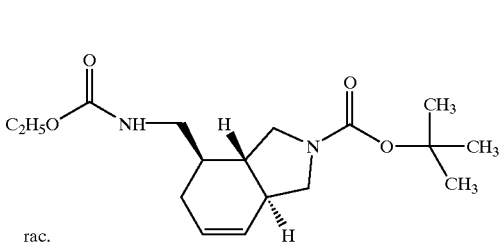

B

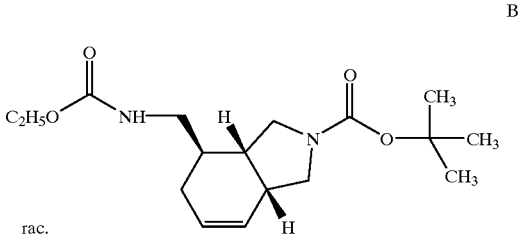

Heat 20.5 g (0.05 mol) of the title compound from Example F.1. (crude mixture of the diastereomers A and B) and 6.5 g (0.1 mol) of sodium azide in 100 ml of DMF at 70° C. for 4 h. Add the reaction solution to 200 ml of water, extract once with 200 ml of petroleum ether, wash the petroleum ether phase once with 50 ml of water, dry with sodium sulphate, and concentrate at room temperature.

Take up the residue in 80 ml of THF, and add 13.1 g (0.05 mol) of triphenylphosphine dissolved in 80 ml of THF dropwise. After the addition is complete, stir at room temperature for 20 h, then slowly add 150 ml of water dropwise and, after addition is complete, stir for a further 15 min. While cooling, add hydrochloric acid (conc. HCl/water 1:3) dropwise until a pH of 3–4 is reached, strip off THF at room temperature in vacuo, cool the reaction solution to 0° C., and filter off the precipitated triphenylphosphine oxide with suction (or, if oily, take up with MTBE).

Adjust the aqueous phase to a pH of ≧12 by the addition of 10% strength sodium hydroxide solution, extract twice with 100 ml of methylene chloride on each occasion, dry the combined extracts with sodium sulphate, subsequently add 6.0 g (0.06 mol) of triethylamine, add, while stirring, 6.0 g (0.055 mol) of ethyl chloroformate dissolved in 20 ml of methylene chloride dropwise, stir at room temperature overnight, wash the reaction solution once with 100 ml of water, dry with sodium sulphate and concentrate.

Purify 23 g of crude product by column chromatography on 100 g of silica gel (63–200 μm) using cyclohexane/acetone (4:1).

Yield: 12.4 g (76% of theory) of a viscous oil Mixture of the diastereomers A and B $R_f$ values (cyclohexane/acetone (2:1)): 0.32 diastereomer A 0.29 diastereomer B The diastereomers A and B are separated by column chromatography on 250 g of silica gel (35–70 µm) using cyclohexane/acetone (8:1).

Yield: 4.3 g (26% of theory) of diastereomer A (viscous oil) 2.4 g (15% of theory) of a mixed fraction 0.6 g (4% of theory) of diastereomer B $^1$H-NMR (Cl$_2$DC-CDCl$_2$; 80° C.):

Diastereomer A: δ=5.75 (d, 1H, H on C-5); 5.66 (m, 1H, H on C-4); 4.67 (br, 1H, NH); 4.08 (q, 2H, ethoxy CH$_2$); 3.62 (br, 2H, H$_a$ on C-7 and H$_a$ on C-9); 3.19 (br, 1H, H$_a$ on CH$_2$—NH); 3.05 (br, H$_b$ on CH$_2$—NH); 2.96 (dd, 1H, H$_b$ on C-9); 2.81 (dd, 1H, H$_b$ on C-7); 2.24–2.34 (m, 2H, H$_a$ on C-3 and H on C-6); 1.78–1.94 (m, 2H, H on C-2 and H$_b$ on C-3); 1.54 (m, 1H, H on C-1); 1.43 (s, 9H); 1.22 ppm (t, 3H, ethoxy CH$_3$).

Diastereomer B: δ=5.69 (m, 1H, H on C-4); 5.57 (m, 1H, H on C-5); 4.65 (br, 1H, NH); 4.08 (q, 2H, ethoxy-CH$_2$); 3.52 (dd, 1H, H$_a$ on C-7); 3.41 (dd, 1H, H$_a$ on C-9); 3.29 (dd, 1H, H$_b$ on C-9); 3.24 (dd, 1H, H$_a$ on CH$_2$—NH); 3.03–3.12 (m, 2H, H$_b$ on C-7 and H$_b$ on CH$_2$—NH); 2.68 (m, 1H, H on C-6); 2.12–2.22 (m, 2H, H on C-1 and H$_a$ on C-3); 1.74–1.87 (m, 2H, H on C-2 and H$_b$ on C-3); 1.43 (s, 9H); 1.22 ppm (t, 3H, ethoxy CH$_3$).

F.3. (1RS,2RS,6SR)-2-Ethyloxycarbonylaminomethyl-8-azabicyclo[4.3.0]non-4-ene

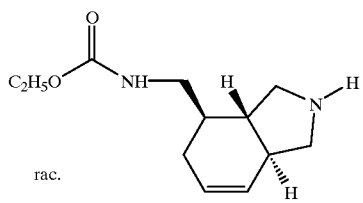

Initially introduce 1.6 g (5.7 mmol) of the title compound A from Example F.2. in 10 ml of methanol. Allow 8 ml of conc. hydrochloric acid to run in rapidly, and then stir for 30 min. Dilute with water to double the volume, and then, while stirring and cooling with ice, add 45% strength sodium hydroxide solution dropwise up to a pH of ≧12. Extract four times with methylene chloride, dry the combined organic phases with sodium sulphate, concentrate, and strip off the solvent residues under high vacuum.

Yield: 0.8 g (63% of theory) of a viscous oil $R_f$=0.16 Methylene chloride/methanol/17% strength aqueous ammonia (15:4:0.5)

$^1$H-NMR (CDCl$_3$): δ=5.81 (d, 1H, H on C-5); 5.67 (m, 1H, H on C-4); 5.00 (br, 1H, NH); 4.10 (q, 2H, ethoxy CH$_2$); 3.18–3.28 and 3.08 (m, 3H and m, 1H: H$_a$ on C-7, H$_a$ on C-9, H$_a$ and H$_b$ on CH$_2$—NH—CO); 2.67 (dd, 1H, H$_b$ on C-9); 2.53 (dd, 1H, H$_b$ on C-7); 2.34 (m, 1H, H$_a$ on C-3); 2.25 (m, 1H, H on C-6); 1.79–1.96 (m, 2H, H on C-2 and H$_b$ on C-3); 1.50 (m, 1H, H on C-1); 1.24 ppm (t, 3H, ethoxy CH$_3$).

EXAMPLE G (1RS,2SR,6RS)-2-Hydroxymethyl-8-azabicyclo[4.3.0]non-4-ene

G.1. (E)-1-tert-Butyloxycarbonylamino-2,4-pentadiene

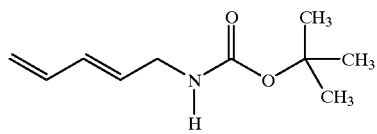

Initially introduce 8.3 g (0.1 mol) of (E)-1-amino-2,4-pentadiene (title compound from Example B.2.) in 50 ml of MTBE, and add 20 mg of 4-hydroxyanisole. Subsequently, at an internal temperature of 20–30° C., add 22.9 g (0.105 mol) of di-tert-butyl dicarbonate dissolved in 50 ml of MTBE dropwise. After addition is complete, stir at room temperature for 20 h. Concentrate, and strip off di-tert-butyl dicarbonate residues at 40° C. under high vacuum.

Yield: 18.9 g (crude product) of a colourless oil $R_f$=0.25 Cyclohexane/acetone (4:1)

$^1$H-NMR (CDCl$_3$): δ=6.05–6.43 (m, 2H, H on C-3 and C-4); 5.68 (dd, 1H, H on C-2, J=14 and 6 Hz); 5.17 (dd, 1H, H$_a$ on C-5, J=16 Hz); 5.07 (dd, 1H, H$_b$ on C-5, J=10 Hz); 4.75 (br, 1H, NH); 3.77 (t, 2H, H on C-1); 1.45 ppm (s, 9H).

G.2. (1RS,2RS,6RS)-2-tert-Butyloxycarbonylaminomethyl-7,9-dioxo-8-oxabicyclo[4.3.0]non-3-ene

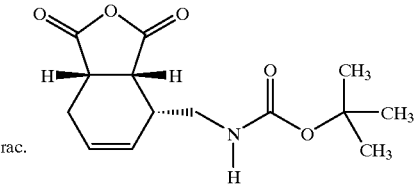

Initially introduce 83.2 g (1.0 mol) of (E)-1-amino-2,4-pentadiene (title compound from Example B.2.) in 250 ml of MTBE, and add 0.1 g of 4-hydroxyanisole. Subsequently, at an internal temperature of 20–30° C., add 229.2 g (1.05 mol) of di-tert-butyl dicarbonate dissolved in 250 ml of MTBE dropwise. After addition is complete, stir at room temperature for 20 h. Concentrate the reaction 10 mixture and take up in 1 l of toluene. Add 103.0 g (1.05 mol) of maleic anhydride, and stir at an internal temperature of 60° C. for 24 h. Filter off the precipitate with suction, wash it with toluene and dry it at 50° C. to constant weight.

Yield: 208.2 g (74% of theory) white, crystalline solid

Melting point: 157–159° C.

$^1$H-NMR (d$_6$-DMSO): δ=5.81 (m, 1H, H on C-4); 5.59 (d, 1H, H on C-3); 3.77 (dd, 1H H$_a$ on CH$_2$—NH); 3.44 (m, 2H, H on C-1 and H$_b$ on CH$_2$—NH); 2.94 (m, 1H, H on C-2); 2.66 (m, 1H, H on C-6); 2.16 (m, 1H, H$_a$ on C-5); 2.06 (m, 1H, H$_b$ on C-5); 1.43 ppm (s, 9H).

G.3. Methyl (1RS,2SR,6RS)-9-oxo-8-azabicyclo[4.3.0]non-4-ene-2-carboxylate

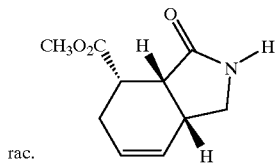

Initially introduce 83.2 g (1.0 mol) of (E)-1-amino-2,4-pentadiene (title compound from Example B.2.) in 250 ml of TEF, and add 0.1 g of 4-hydroxyanisole. Subsequently, at an internal temperature of 20–30° C., add 229.2 g (1.05 mol) of di-tert-butyl dicarbonate dissolved in 250 ml of THF dropwise. After addition is complete, stir at room temperature for 20 h. Add 103.0 g (1.05 mol) of maleic anhydride, and heat to reflux for 5 h. Concentrate and take up the residue in 500 ml of methanol, add 30 ml of p-toluenesulphonic acid, and then heat once again to reflux for 5 h. After cooling with ice, and stirring, rapidly add a solution of 20 g of sodium carbonate dissolved in 500 ml of water dropwise, allow the mixture to stand for a further 30 min in an ice bath, and filter off the precipitate with suction, wash it with a little water, and dry it at 50° C. to constant weight.

Yield: 125–148 g (64–76% of theory) white, crystalline solid

Melting point: 190–193° C.

$^1$H-NMR ($d_6$-DMSO): δ=7.50 (s, 1H, NH); 5.77 (m, 1H, H on C-4); 5.56 (m, 1H, H on C-5); 3.60 (s, 3H, $CH_3O$); 3.42 (dd, 1H, $H_a$ on C-7); 3.16 (dd, 1H, H on C-1); 3.00 (m, 1H, E on C-6); 2.88 (dd, 1H, $H_b$ on C-7); 2.67 (m, 1H, H on C-2); 2.02–2.18 ppm (m, 2H, $H_a$ and $H_b$ on C-3).

G.4. (1RS,2SR,6RS)-2-Hydroxmethyl-8-azabicyclo[4.3.0]]non-4-ene

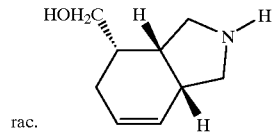

Initially introduce 19.6 g (0.1 mol) of the title compound from Example G.3. in 100 ml of THF under an atmosphere of an inert gas (suspension). Add 100 ml (0.15 mol) of 1.5 M DIBAH solution in toluene dropwise at an internal temperature of 10–20° C. Add the clear, homogeneous solution thus obtained dropwise to a suspension of 1.9 g of lithium alanate in 50 ml of THF. After addition is complete, stir at room temperature for 15 min, and then at reflux temperature for 30 min. After cooling, add 3.8 g (0.1 mol) of lithium alanate in portions, and then heat to reflux for 24 h. After cooling, add dropwise in succession 50 ml of water and 10 ml of 1 M sodium hydroxide solution, and filter off the precipitate with suction and extract it three times by boiling with 150 ml of ethanol on each occasion. Combine the filtrate and extracts and concentrate.

Yield: 16.4 g (product contains lithium hydroxide and aluminium hydroxide) $R_f$=0.3
Methylene chloride/methanol/17% strength aqueous ammonia (2:4:1)

EXAMPLE H (1RS,2SR,6RS)-2-Ethyloxycarbonylaminomethyl-8-azabicyclo[4.3.0]non-4-ene H.1. (1RS,2SR,6RS)-8-tert-Butyloxycarbonyl-2-hydroxmethyl-8-azabicyclo[4.3.0]non-4-ene

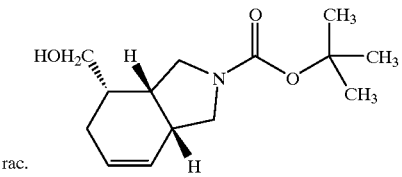

Dissolve 16.4 g of the crude product from Example G.4. (corresponds to 0.1 mol of the title compound from Example G.4.) in 100 ml of THF. At an internal temperature of 0–5° C., add 22.9 g (0.105 mol) of di-tert-butyl dicarbonate dissolved in 100 ml of THF dropwise, stir at 0° C. for 24 h, and then subsequently at room temperature for a further 24 h. Concentrate, and purify the crude product by column chromatography on 250 g of silica gel (65–200 μm) using cyclohexane/acetone (2:1).

Yield: 13.7 g (54% of theory over 2 steps); viscous oil
$R_f$=0.21 title compound 0.08 title compound from Example G.4.

H.2. (1RS,2SR,6RS)-8-tert-Butyloxycarbonyl-2-(4-toluenesulphonyloxymethyl)-8-azabicyclo[4.3.0]non-4-ene

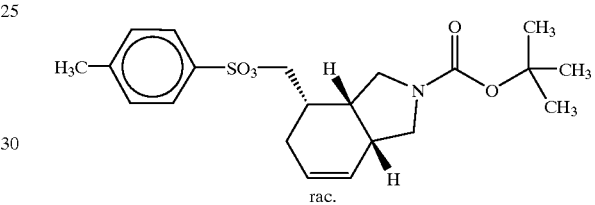

The title compound is obtained from the title compound from Example H.1. in analogy with Example F.1.

Yield: 81–83% of theory
Melting point: 160–162° C.

$^1$H-NMR (CDCl$_3$): δ=7.79 (m, 2H, aryl-H); 7.37 (d, 2H, aryl-H); 5.67 (m, 1H, H on C-4); 5.47 (m, 1H, H on C-5); 3.78–3.97 (m, 2H, tosyl-OCH$_2$—); 3.13–3.42 (m, 3H, CH$_2$—N); 2.95 (t, 1H, CH$_2$—N); 2.74 (m, 1H); 2.54 (m, 1H); 2.47 (s, 3H, aryl-CH$_3$); 2.32 (m, 1H, H on C-2); 2.06 (m, 1H, H$_a$ on C-3); 1.66–1.83 (m, 1H, H$_b$ on C-3), 1.44 ppm (s, 9H).

H.3. (1RS,2SR,6RS)-8-tert-Butyloxycarbonyl-2-ethyloxycarbonylaminomethyl-8-azabicyclo[4.3.0]non-4-ene

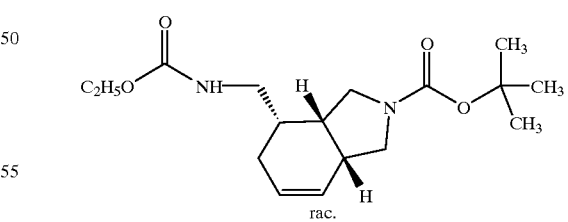

The title compound is obtained from the title compound from Example H.2. in analogy with Example F.2.

Purify the crude product by column chromatography on silica gel (63–200 μm) using cyclohexane/acetone (2:1).

Yield; 76% of theory; clear, viscous oil
$R_f$=0.35 (cyclohexane/acetone 2:1)

$^1$H-NMR (Cl$_2$DC-CDCl$_2$; 80° C.): δ=5.69 (m, 1H, H on C-4) 5.47 (d, 1H, H on C-5); 4.59 (br, 1H, NH); 4.10 (q, 2H, ethoxy CH$_2$); 3.38 (dd, 1H); 3.32 (m, 1H); 3.24 (m, 1H);

3.01–3.08 (m, 3H); 2.79 (m, 1H); 2.47 (m, 1H); 2.07 (m, 2H); 1.78 (m, 1H); 1.42 (s, 9H); 1.22 ppm (t, 3H, ethoxy CH₃).

H.4. (1RS,2SR,6RS)-2-Ethyloxycarbonylaminomethyl-8-azabicyclo[4.3.0]non-4-ene

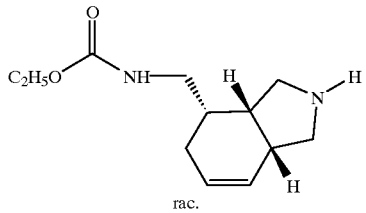

The title compound is obtained from the title compound from Example H.3. in analogy with Example C.3.

Yield: 42% of theory $R_f$=0.93 title compound from Example H.3. 0.23 title compound
Methylene chloride/methanol/17% strength aqueous ammonia (15:4:0.5)

EXAMPLE I (1SR,2RS,3RS,6SR)-2-Ethyloxycarbonylamino-3-methyl-8-azabicyclo[4.3.0]non-4-ene I.1. N-[(2E,4E)-2,4-Hexadienyl]-phthalimide

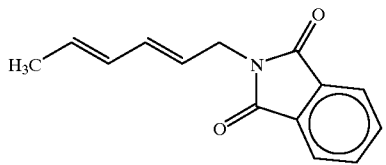

The title compound is obtained from (2E,4E)-1-bromo-2,4-hexadiene in analogy with Example B.1.

Yield: 77–79% of theory

Melting point: 114–117° C. (sample recrystallised from ethanol)

¹H-NMR (CDCl₃): δ=7.85 (m, 2H); 7.72 (m, 2H); 6.25 (dd, 1.1); 6.00 (ddd, 1H); 5.5–5.8 (m, 2H); 4.29 (d, 2H); 1.74 ppm (d, 3H).

I.2. (2E,4E)-1-Amino-2,4-hexadiene

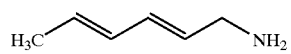

The title compound is obtained from the title compound from Example I.1. in analogy with Example B.2.; boiling range: 40–70° C. under 16–18 mbar.

Yield: 67–83% of theory

I.3. Ethyl (E)-4-[(2E,4E)-2,4-Hexadienylamino]-2-butenoate

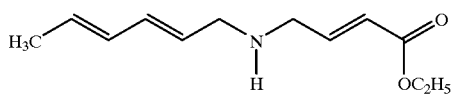

The title compound is obtained from the title compound from Example I.2. in analogy with Example B.3.

Yield; 46% of theory

¹H-NMR (CDCl₃): δ=6.98 (dt, 1H); 5.9–6.25 (m, 3H); 5.5–5.8 (m, 2H); 4.19 (q, 2H); 3.40 (dd, 2H); 3.27 (d, 2H); 1.76 (d, 3H); 1.29 ppm (t, 3H).

I.4. Ethyl (1RS,2RS,3RS,6SR)-8-tert-butyloxycarbonyl-3-methyl-8-azabicyclo[4.3.0]non-4-ene-2-carboxylate (diastereomer A) and ethyl (1RS,2RS,3SR,6RS)-8-tert-butyloxycarbonyl-3-methyl-8-azabicyclo[4.3.0]non-4-ene-2-carboxylate (diastereomer B)

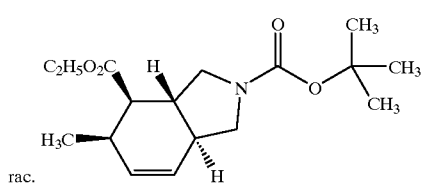

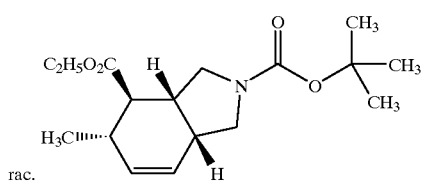

The title compounds are obtained from the title compound from Example I.3. in analogy with Example B.4.

Yield: 70% of theory; mixture of 2 diastereomers A and B in the ratio A:B=4:1.

$R_f$=0.49 (cyclohexane/acetone 2:1)

I.5. (1RS,2RS,3RS)-6SR)-8-tert-Butyloxycarbonyl-3-methyl-8-azabicyclo[4.3.0]non-4-ene-2-carboxylic acid

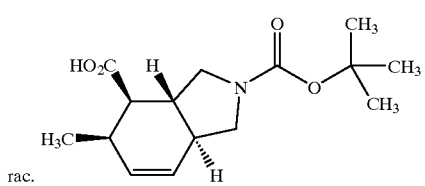

Initially introduce 1.17 g (21 mmol) of potassium hydroxide dissolved in 20 ml of water. Add 5.9 g (19 mmol) of the title compound from Example I.4. dissolved in 20 ml of methanol, and heat to reflux for 48 h under an atmosphere of nitrogen. Concentrate, take up in water, extract once with methylene chloride, adjust the aqueous phase to pH 3–4 with acetic acid, and filter off the precipitate with suction, wash it with water, dry it at room temperature, and recrystallise it from cyclohexane/acetone 6:1.

Yield: 2.25 g (42% of theory)

Melting point: 189° C.

¹H-NMR (d₆-DMSO): δ=5.77 (d, 1H); 5.61 (m, 1H); 3.67 (m, 1H); 3.54 (m, 1H); 2.61–2.95 (m, 4H); 2.30 (m, 1H); 1.82 (m, 1H); 1.40 (s, 9H); 0.90 ppm (d, 3H).

I.6. (1SR,2RS,3RS,6SR)-8-tert-Butyloxycarbonyl-2-ethyloxycarbonylamino-3-methyl-8-azabicyclo[4.3.0]non-4-ene

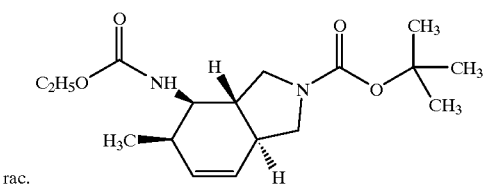

rac.

The title compound is obtained from 2.25 g (8 mmol) of the title compound from Example I.5. in analogy with Example C.2. Alterations as compared with Example C.2. are: 8 h of reflux in ethanol instead of 4 h; purification by column chromatography on 100 g of silica gel (63–200 μm) using toluene/ethyl acetate (2:1).

Yield: 1.6 g (59% of theory) of a clear oil $^1$H-NMR (CDCl$_3$): δ=5.68 and 5.72 (2d, 1H); 5.61 (m, 1H); 4.81 (m, 1H); 4.0–4.2 (m, 3H); 3.53 (m), 3.62 (m) and 3.72 (dd) [2H]; 3.08 (t, 1H); 2.92 (t, 1H); 2.75 (m, 1H); 2.47 (m, 1H); 1.83 (m, 1H); 1.47 (m, 9H); 1.25 (m, 3H); 0.97 ppm (d, 3H).

I.7. (1SR,2RS,3RS,6SR)-2-Ethyloxycarbonylamino-3-methyl-8-azabicyclo[4.3.0]non-4-ene

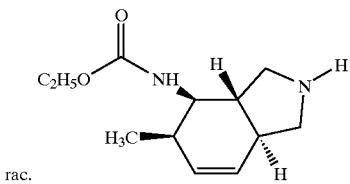

rac.

The title compound is obtained from 1.6 g (4.7 mmol) of the title compound from Example I.6. in analogy with Example C.3.

Yield: 0.7 g (70% of theory) of a yellowish oil; R$_f$=0.09 Methylene chloride/methanol/17% strength aqueous ammonia (15:4:0.5)

EXAMPLE K (1RS,2RS,6RS)-2-Ethoxycarbonylaminomethyl-8-azabicyclo-[4.30]non-4-ene K.1. Diethyl 3-phthalimidoethyl-cyclohex-4-ene-1,2-dicarboxylate

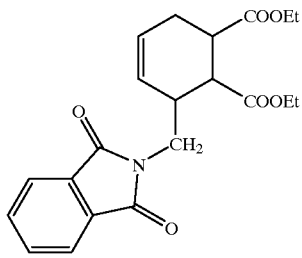

10.67 g (50% mol) of N-[(E)-2,4-pentadienyl]-phthalimide (title compound from Example B.1.) and 8.61 g of diethyl fumarate are heated under reflux for 2 days in 50 ml of toluene. The mixture is concentrated and the residue is subjected to chromatography on silica gel (eluent: cyclohexane/acetone 8:1).

Yield: 14.8 g (77% of theory).
Melting point: 80–84° C.

K.2. Ethyl (1RS,2RS,6RS)-9-oxo-8-azabicyclor[4.3.0.]non-4-ene-2-carboxylate (A) and Ethyl (1RS,2RS,6SR)-9-oxo-8-azabicyclor[4.3.0]non-4-ene-2-carboxylate (B)

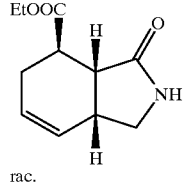

rac.

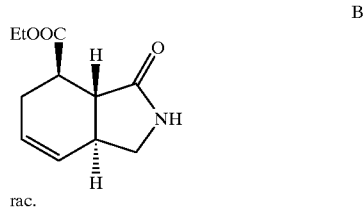

rac.

150.3 g (0.39 mol) of the title compound from Example K.1. are initially introduced in 720 ml of ethanol and 173.3 g (2.9 mol) of ethylenediamine are added dropwise while cooling in ice. The mixture is stirred at room temperature for 20 h, concentrated in vacuo, and then diluted with water (about 700 ml); the pH is then adjusted to 2–3 with conc. hydrochloric acid and the mixture is extracted three times with 500 ml of dichloromethane on each occasion. The organic phase is dried (sodium sulphate) and concentrated in vacuo. The diastereomers are separated by chromatography (eluent: cyclohexane/acetone 1:1).

Yield: 36.7 g of product A (45% of theory) R$_f$=0.47 (cyclohexane/acetone 1:1), 37.0 g of product B (45% of theory) R$_f$=0.22 (cyclohexane/acetone 1:1).

K.3. (1RS,2RS,6RS)-2-Hydroxymethyl-8-azabicyclo-[4.3.0]non-4-ene

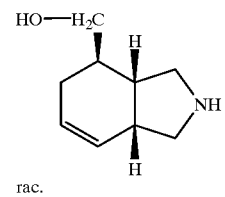

rac.

5.2 g (25 mmol) of ethyl (1RS,2RS,6RS)-9-oxo-8-azabicyclo[4.3.0]non-4-ene-2-carboxylate (product A from Example K.2.) are dissolved in 50 ml of tetrahydrofuran under a nitrogen atmosphere and 130 ml of a 1.5 molar di(isobutyl)aluminium hydride solution (195 mmol) are subsequently added dropwise. The solution is heated under reflux for 16 h. After the reaction is complete, 60 ml of methanol, 30 ml of tert-butyl methyl ether and 10 ml of water are added dropwise successively and filtration with suction is then carried out in the presence of tonsil. The suction filter residue is stirred twice with a mixture of ethanol/conc. ammonia/water (10:1:1) and filtered off with suction once again. The combined filtrates are concentrated and the crude product is purified by chromatography (eluent: dichloromethanel-methanol/conc. ammonia 2:4:1).

Yield: 2.7 g (71% of theory).

¹H-NMR (DMSO-d₆): 5.69 (m, 1H, 4-H); 5.60 (m, 1H, 5-H); 3.39 (dd, 1H, 10a-H); 3.26 (dd, 1H, 10b-H); 2.97 (m, 2H, 7a-H, 9a-H); 2.63 (m, 1H, 9b-H); 2.38 (bs, 1H, 6-H); 2.32 (dd, 1H, 7b-H); 2.06 (m, 1H, 3a-H); 1.95 (m, 1H, 1-H); 1.77 (m, 1H, 3b-H); 1.44 ppm (m, 1H, 2-H).

K.4. (1RS,2RS,6RS)-8-tert-Butoxycarbonyl-2-hydroxymethyl-8-azabicyclo[4.3.0]non-4-ene

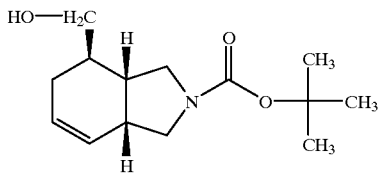
rac.

The product from Example K.3. (8.87 g; 58 mmol) is reacted as described in Example H.1.

Yield: 11.0 g (75% of theory). $R_f$=0.25 (Cyclohexane/acetone 2:1).

K.5. (1RS,2RS,6RS)-8-tert-Butoxycarbonyl-2-(4-toluene-sulphonyloxymethyl)-8-azabicyclo[4.3.0]non-4-ene

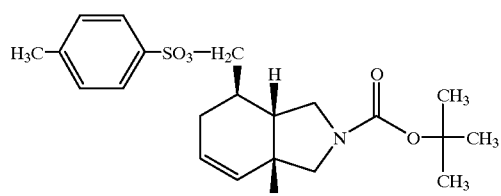
rac.

The title compound is obtained from the product of Example K.4. in analogy with Example F.1.

Yield: 97% of theory. $R_f$=0.40 (cyclohexane/acetone 2:1).

K.6. (1RS,2RS,6RS)-8-tert-Butoxycarbonyl-2-azidomethyl-8-azabicyclo[4.3.0]non-4-ene

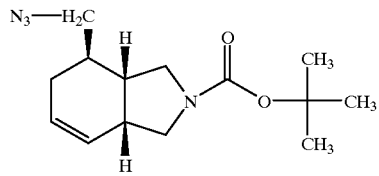
rac.

A solution of 33 g (0.08 mol) of (1RS,2RS,6RS)-8-tert-butyloxycarbonyl-2-(4-toluenesulphonyloxymethyl)-8-azabicyclo[4.3.0]non-4-ene (title compound from Example K.5.) and 15.8 g (0.24 mol) of sodium azide in 200 ml of N,N-dimethylformamide is stirred at 70° C. for 40 h. After cooling, the solution is diluted with water (500 ml) and extracted three times with 250 ml of petroleum ether on each occasion. The combined organic phase is washed with 5% strength sodium hydrogen carbonate solution, dried (sodium sulphate) and concentrated.

Yield: 21.6 g (97%)

¹H-NMR (CDCl₃): 5.71 (m, 1H, C=CH); 5.58 (m, 1H,C=CH); 3.61–3.22 (m, 5H); 3.10 (m, 1H); 2.70 (bs, 1H); 2.24 (m, 2H); 1.91 (m, 2H); 1.47 ppm (s, 9H, tert-butyl).

K.7. (1RS,2RS,6RS)-8-tert-Butoxycarbonyl-2-aminomethyl-8-azabicyclo[4.3.0]non-4-ene

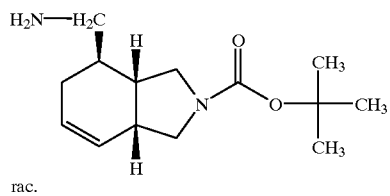
rac.

A solution of the azido compound from Example K.6. (21.6 g; 78 mmol) in 150 ml of pyridine/water (5:1) is saturated with hydrogen sulphide while being cooled in ice and subseguently left at room temperature for 20 h. After the reaction is complete, the mixture is concentrated in vacuo and then distilled several times with toluene, and the residue then subjected to chromatography (eluent: cyclohexane/acetone 1:1).

Yield: 11.0 g (66% of theory). $R_f$=0.12 (cyclohexane/acetone 1:1).

K.8 (1RS,2RS,6RS)-8-tert-Butoxycarbonyl-2-(ethoxycarbon-ylaminomethyl)-8-azabicyclo[4.3.0]non-4-ene

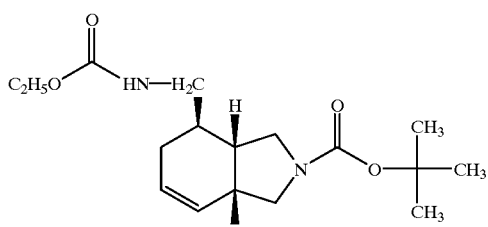
rac.

3.7 g (15 mmol) of (1RS,2RS,6RS)-8-tert-Butoxycarbonyl-2-aminomethyl-8-azabicyclo[4.3.0]non-4-ene are initially introduced in 40 ml of dioxane and 15 ml of water, 2.3 g (16 mmol) of potassium carbonate are added, and then 1.75 g (16 mmol) of ethyl chloroformate are added dropwise at room temperature. After stirring for two hours, the mixture is concentrated in vacuo and the residue is taken up in dichloromethane (70 ml), extracted twice by shaking with 25 ml of water on each occasion, dried (sodium sulphate) and concentrated. The crude product is purified by chromatography (cyclohexane/acetone 2:1).

Yield: 2.8 g (59% of theory). $R_f$=0.53 (cyclohexane/acetone 1:1).

K.9. (1RS,2RS,6RS)-2-(Ethoxycarbonylaminomethyl)-8-azabicyclo[4.3.0]non-4-ene

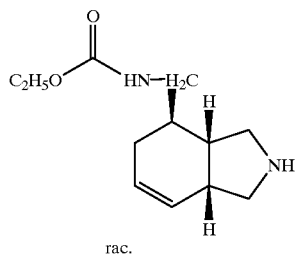
rac.

7.6 g (23 mmol) of the product from Example K.8. are initially introduced in 100 ml of methanol/water (1:1) and 30 ml of half-concentrated hydrochloric acid are allowed to run in at RT. After gas evolution is complete, the mixture is subsequently stirred for 30 minutes and then diluted with ice water (about 100 ml), after which the pH is adjusted to 12 with conc. sodium hydroxide solution. The aqueous phase is extracted four times with 100 ml of dichloromethane on each occasion. The extracts are comnbined, dried over sodium sulphate and concentrated in vacuo.

Yield: 3.9 g (76% of theory). $R_f$=0.45 (dichloromethane/methanol/conc. ammonia 2:4:0.1).

EXAMPLE L

(1RS,2RS,6RS)-2-Aminomethyl-8-azabicyclo[4.3.0]non-4-ene bis-trifluoroacetate

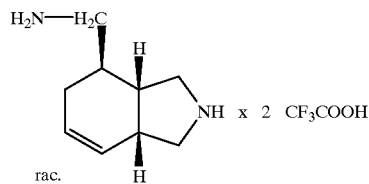
rac.

30 ml of trifluoroacetic acid are added to a solution of 2.0 g (8 mmol) of (1RS,2RS,6RS)-8-tert-butoxycarbonyl-2-aminomethyl-8-azabicyclo[4.3.0]non-4-ene (product from Example K.7.) in 30 ml of dichloromethane, and the mixture is left at room temperature for 30 minutes. The solvent and the acid are distilled off in the presence of toluene and the mixture is subsequently distilled several times with toluene. The product is dried in a vacuum desiccator over potassium hydroxide/phosphorus pentoxide (1:1).

Yield: 1.5 g of brown oil.

$^1$H-NMR (DMSO-d$_6$): 5.78 (m, 1H, C=CH); 5.60 (m, 1H, C=CH); 3.34 (m, 2H); 3.03 (m, 1H); 2.87 (m, 2H); 2.73 (m, 1H); 2.45 (m, 1H); 2.34 (m, 1H); 2.22 (m, 1H); 1.94 ppm (m, 2H) FAB-MS: M+1 =153.

EXAMPLE M

(1RS, 2RS, 6SR) -2-Ethoxycarbonylaminomethyl-8-azabicyclo-[4.3.0]non-4-ene (The product is identical to the title compound from Example F)

M.1. (1RS,2RS,6SR) -2-Hydroxymethyl-8-azabicyclo[4.3.0]non-4-ene

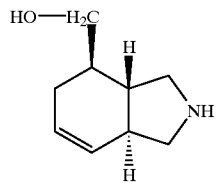
rac.

Ethyl-(1RS,2RS,6SR)-9-oxo-8-azabicyclo[4.3.0]non-4-ene-2-carboxylate (product B from Example K.2.) is reacted in analogy with Example K.3.

Yield: 75% of theory. $R_f$=0.22 (dichloromethane/methanol/conc. ammonia 15:4:0.5).

M.2. (1RS,2RS,6SR)-8-tert-Butoxycarbonyl-2-hydroxymethyl-8-azabicyclo[4.3.0]non-4-ene

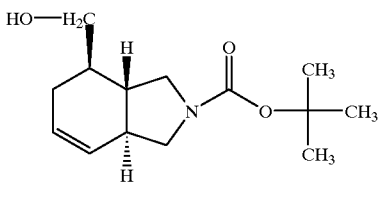
rac.

The product from Example M.1. is reacted in analogy with Example K.4.

Yield: 64% of theory. $R_f$=0.23 (cyclohexane/acetone 2:1).

M3. (1RS,2RS,6SR)-8-tert-Butoxycarbonyl-2-(4-toluene-sulphonyloxymethyl)-8-azabicyclo[4.3.0]non-4-ene

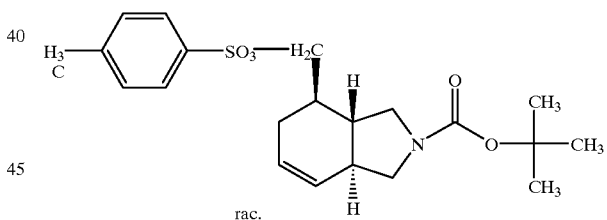
rac.

The title compound is obtained from the product of Example M.2. in analogy with Example F.1.

Yield: 91–98% of theory. $R_f$=0.59 (cyclohexane/acetone 2:1).

M.4. (1RS,2RS,6SR)-8-tert-Butoxycarbonyl-2-azidomethyl-8-azabicyclo[4.3.0]non-4-ene

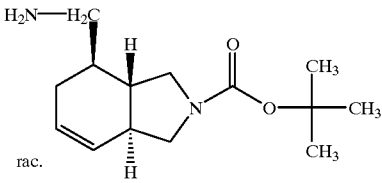
rac.

4.15 g (64 mmol) of sodium azide are added to a solution of 13.0 g (32 mmol) of the product from Example M.3. in 80 ml of N,N-dimethylformamide and the mixture is stirred at 70° C. for 4 h. The same quantity of sodium azide is then added once again and the mixture is stirred at 100° C. for a further 6 h. Working up subsequently takes place as described in Example K.6.

Yield: 7.0 g (79% of theory). $R_f$=0.55 (cyclohexane/acetone 2:1).

M.5. (1RS,2RS,6SR)-8-tert-Butoxycarbonyl-2-aminomethyl-8-azabicyclo[4.3.0]non-4-ene

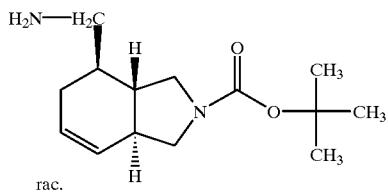

The azido compound from Example M.4. is reacted as described in Example K.7. The chromatography is carried out using methanol/dichloromethane/conc. ammonia 15:2:0.1.

Yield: 75% of theory. $R_f$=0.12 (methanol/dichloromethane/conc. ammonia 15:2:0.1)

M.6. (1RS,2RS,6SR)-8-tert-Butoxycarbonyl-2-(ethoxycarbonylaminomethyl)-8-azabicyclo[4.3.0]non-4-ene

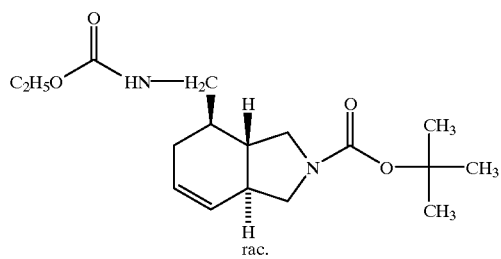

4.3 g (17 mmol) of the amino compound from Example M.5. and 1.9 g (19 mmol) of triethylamine are initially introduced in 50 ml of dichloromethane, 2.2 g (20 mmoi) of ethyl chloroformate, dissolved in 10 ml of dichloromethane, are added dropwise at 0° C., and the mixture is subsequently stirred at room temperature for 24 h. Water (50 ml) is added to the solution and the phases are separated. The aqueous phase is extracted a further three times with 40 ml of dichloromethane on each occasion. The organic phases are combined, dried (sodium sulphate) and concentrated.

Yield: 5.3 g (96% of theory).

$^1$H-NMR (CDCl$_2$—CDCl$_2$, 80° C.): 5.79 (ddd, 1H, C=CH); 5.58 (m, 1H, C=CH); 4.61 (bs, 1H, carbamate-NH); 4.23 (m, 1H); 4.12 (q, 2H, ethyl-CH$_2$); 3.99 (m, 1H); 3.20–3.08 (m, 2H); 2.82 (m, 2H); 2.25 (m, 2H); 2.09 (m, 1H); 1.84 (m, 2H); 1.42 (s, 9H, tert-butyl); 1.37 ppm (t, 3H, ethyl-CH$_3$).

M.7. (1RS,2RS,6SR)-2-(Ethoxycarbonylaminomethyl)-8-azabicyclo[4.3.0]non-4-ene

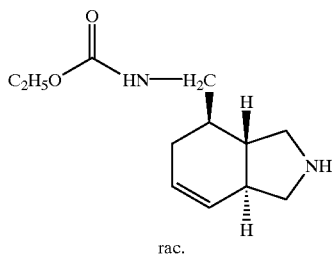

(1RS,2RS,6SR)-8-tert-Butoxycarbonyl-2-(ethoxycarbonylaminomethyl)-8-azabicyclo[4.3.0]non-4-ene is reacted as described in Example K.9.

Yield: quantitative. $R_f$=0.55 (methanol/dichloromethane/conc. ammonia 15:4:0.5).

EXAMPLE N (1SR,2RS,6RS)-2-Methylamino-8-azabicyclo[4.3.0]non-4-ene

N.1. (1RS,2RS,6RS)-9-Oxo-8-azabicyclo[4.3.0]non-4-ene-2-carboxylic acid

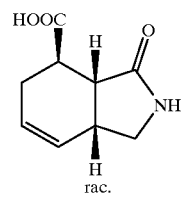

8.36 g (40 nmol) of ethyl (1RS,2RS,6RS)-9-oxo-8-azabicyclo[4.3.0]non-4-ene-2-carboxylate (product A from Example K.2.) are stirred at 60° C. for 40 h with 30 ml of water and 5 g of conc. sulphuric acid. On cooling, the product precipitates. The precipitate is washed with a little cold water and dried in a vacuum drying oven at 50° C.

Yield: 4.80 g (66% of theory).

$^1$H-NMR (DMSO-d$_6$): 12.35 (s, 1H, COOH); 7.60 (s, 1H, lactam-NH); 5.74 (m, 1H, C=CH); 5.59 (m, 1H, C=CH); 3.45 (dd, 1H, 7a-H); 2.95–2.85 (m, 4H, 1-H, 2-H, 6-H, 7b-H); 2.29 (m, 1H, 3a-H); 2.00 ppm (m, 1H, 3b-H).

N.2. (1SR,2RS,6RS)-2-Ethoxycarbonylamino-9-oxo-8-azabicyclo[4.3.0]non-4-ene

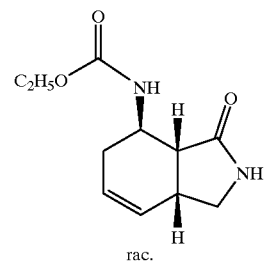

(1RS,2RS,6RS)-9-Oxo-8-azabicyclo[4.3.0]non-4-ene-2-carboxylic acid (title compound from Example N.1.) is reacted in analogy with Example C.2.

Yield: 68% of theory. $R_f$=0.06 (cyclohexane/acetone 1:1).

N.3. (1SR,2RS,6RS)-2-Methylamino-8-azabicyclo[4.3.0]non-4-ene

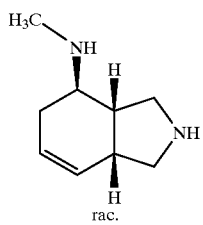

The title compound is obtained by reacting the product from Example N.2. with 10 equivalents of diisobutyl-aluminium hydride in analogy with Example K.3. and then working it up.

Yield: 51% of theory.

$^1$H-NMR (CDCl$_3$): 5.72 (m, 1H, C=CH); 5.68 (m, 1H, C=CH); 3.19–3.10 (m, 2H); 2.88 (dd, 1H); 2.60 (dd, 1H); 2.50 (m, 1H); 2.44 (s, 3H, N—CH$_3$); 2.33–2.28 (m, 2H); 2.19 (m, 1H); 1.89 ppm (m, 1H).

EXAMPLE O (1SR,2SR,6RS)-2-Methylamino-8-azabicyclo[4,3,0]non-4-ene

O.1. (1RS,2SR,6RS)-9-Oxo-8-azabicyclo[4.3.0]non-4-ene-2-carboxylic acid

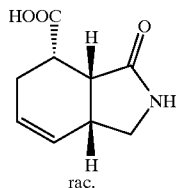

0.2 g of conc. sulphuric acid, 25 ml of water and 25 ml of acetic acid are initially introduced at 60° C. 9.8 g (50 mmol) of the product from Example G.3. are added in small portions. The mixture is subsequently stirred at 60° C. for 5 h. For the working up, a solution of 0.8 g of sodium hydrogen carbonate in 10 ml of water is added and the mixture is concentrated in vacuo. The residue is suspended in 40 ml of water and dissolved by adding conc. sodium hydroxide solution while cooling in ice. After insoluble components have been filtered off with suction, the solution is acidified with half-concentrated hydrochloric acid and cooled once more to 0° C. The product which precipitates is washed with a little cold water and subsequently dried at 50° C. in a vacuum drying oven.

Yield: 4.8 g (53% of theory). Melting point: 192–193° C.

O.2. (1SR,2SR,6RS)-2-Ethoxycarbonylamino-9-oxo-8-azabicyclo[4.3.0]non-4-ene

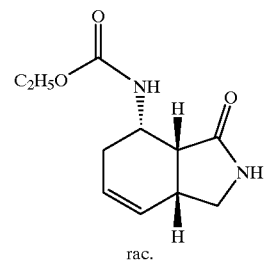

(1RS,2SR,6RS)-9-Oxo-8-azabicyclo[4.3.0]non-4-ene-2-carboxylic acid (title compound from Example O.1.) is reacted as described in Example C.2.

Yield: 68% of theory. Melting point: 160–164° C.

O.3. (1SR,2SR,6SR)-2-Methylamino-8-azabicyclo[4.3.0]non-4-ene

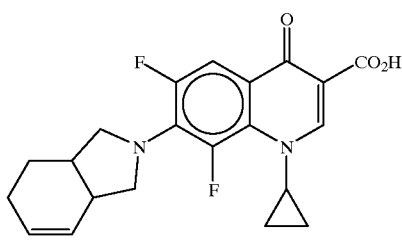

The title compound is obtained by reacting the product from Example O.2. with 10 equivalents of diisobutyl-aluminium hydride in analogy with Example K.3., and working it up.

Yield: 81% of theory.

$^1$H-NMR (CDCl$_3$): 5.72 (m, 1H, C=CH); 5.50 (m, 1H, C=CH); 3.04–2.77 (m, 6H); 2.60 (m, 1H); 2.49 (s, 3H, N—CH$_3$); 2.31 (bs, 2H, 2x NH); 2.25 (m, 1H); 1.89 ppm (m, 1H).

Preparation of the active compounds:

EXAMPLE 1

7-(8-Azabicyclo[4.3.0]non-2-en-8-yl)-1-cyclopropyl-6,8-difluoro-1,4-dihydro-4-oxo-3-quinolinecarboxylic acid Heat 1.4 g (5 mmol) of 1-cyclopropyl-6,7,8-trifluoro-1,4-dihydro-4-oxo-3-quinolinecarboxylic acid, 0.6 g (5 mmol) of DABCO and 0.8 g (6 mmol) of the title compound from Example A to reflux for 3 h in a mixture consisting of 15 ml of acetonitrile and 7.5 ml of DMF. After cooling, add 25 ml of water and 2.5 ml of acetic acid, and filter off the precipitate with suction, wash it with water, and dry it at 50° C.

Yield: 1.8 g (93% of theory) Melting point: 224–226° C. Elementary analysis: ($C_{21}H_{20}F_2N_2O_3$) Calculated C: 65.3 H: 5.2 N: 7.3 F: 9.8 Found C: 65.35 H: 5.15 N: 7.25 F: 9.7

EXAMPLE 2

(1'RS,2'RS 6'SR) -1-Cyclopropyl-7- (2'-ethyloxycarbonyl-8'-azabicyclo[4.3.0]non-4'-en-8'-yl)-6,8-difluoro-1,4-dihydro-4-oxo-3-quinolinecarboxylic acid

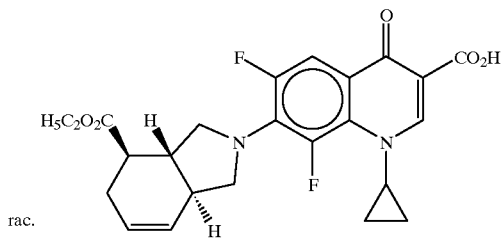

Heat 0.7 g (2.5 mmol) of 1-cyclopropyl-6,7,8-trifluoro-1,4-dihydro-4-oxo-3-quinolinecarboxylic acid, 0.3 g (2.5 mmol) of DABCO and 0.6 g (3 mmol) of the compound A from Example B to reflux for 5 h in a mixture consisting of 10 ml of acetonitrile and 5 ml of DMF. After cooling, add 30 ml of water and 1 ml of acetic acid, and filter off the precipitate with suction, wash it with water, and dry it over KOH in a desiccator.

Yield: 0.95 g (83% of theory) Melting point: 212–214° C. Elementary analysis: ($C_{24}H_{24}F_2N_2O_5$) Calculated C: 62.9 H: 5.2 N: 6.1 F: 8.3 Found C: 62.7 H: 5.3 N: 6.1 F: 8.3

$^1$H-NMR ($d_6$-DMSO): δ=8.62 (s, 1H, H on C-2); 7.72 (d, 1H, H on C-5); 5.91 (d, 1H, H on C-5'); 5.76 (m, 1H, H on C-4'); 4.05–4.19 (m, 3H ethoxy $CH_2$ and cyclopropyl CH); 3.84 (m, 1H, $CH_2N$); 3.76 (m, 2H, $CH_2N$); 3.53 (m, 1H, $CH_2N$); 2.84 (m, 1H, H on C-2'); 2.43–2.58 (m, 2H, $H_a$ on C-3' and H on C-6'); 2.33 (m, 1H, $H_b$ on C-3'); 1.94 (m, 1H, H on C-1'); 1.22 (t, 3H, ethoxy $CH_3$); 1.07–1.26 ppm (m, 4H, cyclopropyl $CH_2$).

EXAMPLE 3

(1'SR, 2'RS,6'SR)-1-Cyclopropyl-7-(2'-ethyloxycarbonyl-amino-8'-azabicyclo[4.3.0]non-4'-en-8'-yl)-6,8-difluoro-1,4-dihydro-4-oxo-3-quinolinecarboxylic acid

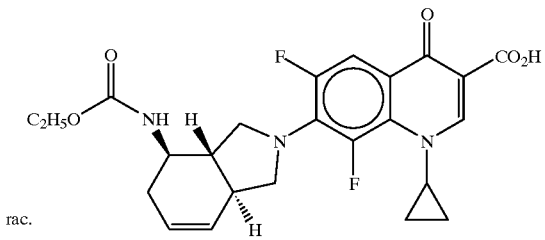

Heat 2.8 g (10 mmol) of 1-cyclopropyl-6,7,8-trifluoro-1,4-dihydro-4-oxo-3-quinolinecarboxylic acid, 1.1 g (10 mmol) of DABCO and 2.6 g (12 mmol) of the title compound from Example C to reflux for 3 h in a mixture consisting of 30 ml of acetonitrile and 15 ml of DMF. After cooling, add 45 ml of water and 5 ml of acetic acid, and filter off the precipitate with suction, wash it with water, and dry it at 50° C.

Yield: 4.8 g (94% of theory) of the title compound as an adduct with ½ mol of DMF. Melting point: 239–245° C. Elementary analysis: ($C_{24}H_{25}F_2N_3O_5$ x ½ $C_3H_7NO$) Calculated C: 60.1 H: 5.6 N: 9.6 F: 7.5 Found C: 60.35 H: 5.85 N: 9.7 F: 7.35

$^1$H-NMR ($CDCl_3$):δ=8.69 (s, 1H, H on C-2); 7.75 (d, 1H, H on C-5); 5.84 (d, 1H, H on C-5'); 5.74 (m, 1H, H on C-4'); 4.15 (m, 2H, ethoxy $CH_2$); 3.87–4.05 (m, 3H), 3.82 (m, 1H), 3.64–3.57 (m, 2H): H on C-7'/9', H on C-2', cyclopropyl CH; 2.73 (m, 1H, $H_a$ on C-3'); 2.63 (m, 1H, H on C-6'); 1.96–2.09 (m, 2H, H on C-1' and $H_b$ on C-3'); 1.08–1.32 ppm (m, 7H, cyclopropyl $CH_2$ and ethoxy $CH_3$).

EXAMPLE 4

(1'SR,2'RS,6'SR)-7-(2'-Amino-8'-azabicyclo[4.3.0]non-4'-en-8'-yl)-1-cyclopropyl-6,8-difluoro-1,4-dihydro-4-oxo-3-quinolinecarboxylic acid

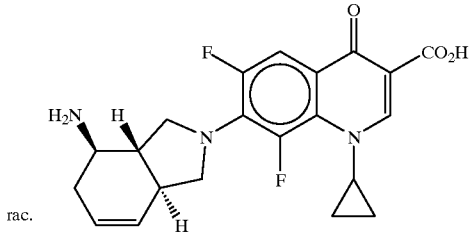

Heat 2.55 g (5 mmol) of the title compound from Example 3 to reflux for 3 h in a mixture consisting of 50 ml of 10% strength potassium hydroxide solution and 25 ml of 1,2-ethanediol. After cooling, add 50 ml of methanol, adjust to a pH of 4–5 with hydrochloric acid (conc. $HCl/H_2O$ 1:3), allow to stand at 0° C. overnight, filter off with suction, suspend the precipitate in 70 ml of a mixture consisting of methanol/water 1:1, adjust to pH 2–3 with hydrochloric acid, stir thoroughly, filter off the sediment with suction again, and wash it with a little water and dry it at 50° C.

Yield: 1.95 g (88% of theory) of the title compound as an adduct with 1 mol of HCl and ½ mol of $H_2O$ Melting point: >300° C. Elementary analysis: ($C_{21}H_{21}F_2N_3O_3$ x HCl x ½ $H_2O$) Calculated C: 56.4 H: 5.2 N: 9.4 Cl: 8.0 F: 8.5 Found C: 56.1 H: 5.35 N: 9.4 Cl: 7.45 F: 8.25

$^1$H-NMR ($CF_3CO_2D$): δ=9.24 (s, 1H, H on C-2); 8.06 (d, 1H, H on C-5); 6.03 (d, 1H, H on C-5'); 5.88 (m, 1H, H on C-4'); 4.47 (m, 1H), 4.37 (m, 1H), 4.22 (m, 2H), 4.04 (m, 1H), 3.96 (m, 1H): H on C-7'/9', H on C-2', cyclopropyl CH; 2.99 (m, 1H, $H_a$ on C-3'); 2.84 (m, 1H, H on C-6'); 2.58 (m, 1H, $H_b$ on C-3'); 2.48 (m, 1H, H on C-1'); 1.57 (m, 2H, cyclopropyl $CH_2$); 1.42 ppm (m, 2H, cyclopropyl $CH_2$)

EXAMPLE 5

(1'SR,2'RS,6'SR)-1-Cyclopropyl-7-(2'-ethyloxycarbonyl-amino-8'-azabicyclo[4.3.0]non-4'-en-8'-yl)-6-fluoro-1.4-dihydro-4-oxo-3-guinolinecarboxylic acid

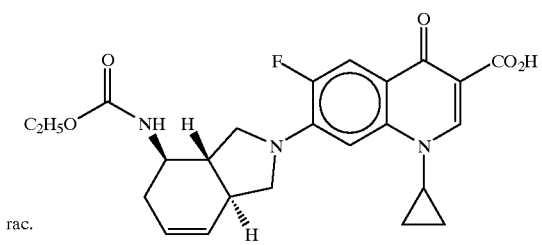

Heat 1.35 g (5 mmol) of 1-cyclopropyl-6,7-difluoro-1,4-dihydro-4-oxo-3-quinolinecarboxylic acid, 0.6 g (5 mmol) of DABCO and 1.3 g (6 mmol) of the title compound from Example C to reflux for 3 h in a mixture consisting of 30 ml of acetonitrile and 15 ml of DMF. After cooling, add 30 ml of water and adjust to pH 4 by adding acetic acid, filter off the precipitate with suction, suspend it in water and stir thoroughly, filter off the sediment with suction again, and dry it at 50° C.

Yield: 2.2 g (97% of theory) Melting point; 197–199° C.

$^1$H-NMR ($d_6$-DMSO): δ=8.57 (s, 1H); 7.78 (d, 1H); 7.34 (br d, 1H); 7.04 (d, 1H); 5.88 (d, 1H); 5.70 (m, 1H); 4.02 (q, 2H); 3.68–3.93 (m, 5H); 3.49 (m, 1H); 2.48–2.72 (m, 2H); 1.93–2.08 (m, 2H); 1.08–1.33 ppm (m, 7H).

EXAMPLE 6

(1'SR,2'RS,6'SR)-7-(2'-Amino-8'-azabicyclo[4.3.0]non-4'-en-8'-yl)-1-cyclopropyl-6-fluoro-1,4-dihydro-4-oxo-3-qinolinecarboxylic acid

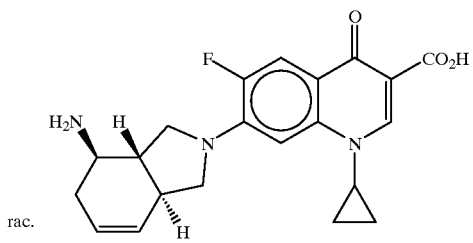

Heat 1.15 g (2.5 mmol) of the title compound from Example 5 to reflux for 3 h in a mixture consisting of 25 ml of 10% strength potassium hydroxide solution and 12.5 ml of 1,2-ethanediol. After cooling, add 50 ml of methanol and 35 ml of water, adjust to a pH of 4–5 with 10% strength hydrochloric acid, and filter off the precipitate with suction, wash it with water, and dry it at 50° C.

Yield: 0.9 g (82% of theory) of the title compound as an adduct with 1 mol of HCl and 1 mol of $H_2O$ Melting point; >300° C. Elementary analysis: ($C_{21}H_{22}FN_3O_3$ x HCl x $H_2O$) Calculated C: 57.6 H: 5.7 N: 9.6 F: 4.3 Found C: 57.5 H: 5.5 N: 9.5 F: 4.1

$^1$H-NMR ($CF_3CO_2D$): δ=9.18 (s, 1H); 8.14 (d, 1H); 7.39 (d, 1H) ; 6.06 (d, 1H); 5.89 (m, 1H); 4.38 (m, 1H); 4.22 (m, 1H); 4.06 (m, 1H); 3.97 (m, 2H); 3.64 (m, 1H); 2.88–3.05 (m, 2H); 2.57 (m, 2H); 1.68 (m, 2H); 1.39 ppm (m, 2H).

EXAMPLE 7

(1'SR,2'RS,6'SR)-1-tert-Butyl-7-(2'-ethyloxycarbonyl-amino-8'-azabicyclo[4.3.0]non-4'-en-8'-yl)-6-fluoro-1,4-dihydro-4-oxo-3-quinolinecarboxylic acid

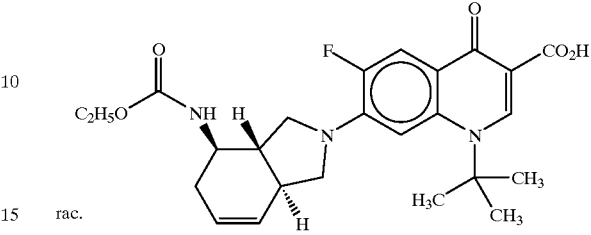

The title compound is obtained from 1.4 g (5 mmol) of 1-tert-butyl-6,7-difluoro-1,4-dihydro-4-oxo-3-quinoline-carboxylic acid and the title compound from Example C in analogy with Example 5.

Yield: 2.3 g (98% of theory) of the title compound as an adduct with ½ mol of DMF. Melting point: 256–257° C. Elemental analysis: ($C_{25}H_{30}FN_3O_5$ x ½ $C_3H_7NO$) Calculated C: 62.7 H: 6.6 N: 9.7 F: 3.7 Found C: 62.45 H: 6.65 N: 9.6 F: 3.6

$^1$H-NMR ($CDCl_3$): δ=8.94 (s, 1H); 7.87 (d, 1H); 6.91 (d, 1H); 5.87 (d, 1H); 5.75 (m, 1H); 5.03 (br., 1H); 4.16 (m, 2H); 4.01 (m, 1H); 3.82 (m, 1H); 3.70 (m, 1 H); 3.60 (m, 1H); 3.33 (m, 1H); 2.65–2.77 (m, 2H); 2.03–2.13 (m, 2H); 1.92 (s, 9H); 1.28 ppm (m, 3H).

EXAMPLE 8

(1'SR,2'RS,6'SR)-7-(2'-Amino-8'-azabicyclo[4.3.0]non-4'-en-8'-yl)-1-tert-butyl-6-fluoro-1,4-dihydro-4-oxo-3-quinolinecarboxylic acid

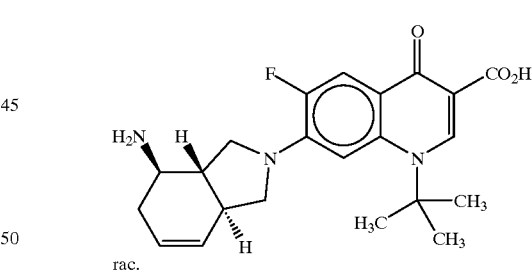

Heat 1.2 g (2.3 mmol) of the title compound from Example 7 to reflux for 3 h in a mixture consisting of 25 ml of 10% strength potassium hydroxide solution and 12.5 ml of 1,2-ethanediol. After cooling, add 25 ml of water, adjust to a pH of 6–7 with 10% strength hydrochloric acid, and filter off the precipitate with suction, wash it with water, and dry it at 50° C.

Yield: 0.95 g (96% of theory) Melting point: >300° C.

$^1$H-NMR ($CF_3CO_2D$): δ=9.44 (s, 1H); 8.19 (d, 1H); 7.47 (d, 1H); 6.04 (d, 1H); 5.88 (m, 1H); 4.38 (m, 1H); 4.37 (m, 1H); 4.16 (m, 1H); 4.05 (m, 1H); 3.97 (m, 1H); 3.63 (m, 1H); 2.87–3.04 (m, 2H); 2.50–2.64 (m, 2H); 2.11 ppm (s, 9H).

EXAMPLE 9

(1'SR,2'RS,6'SR)-1-Ethyl-7-(2'-ethyloxycarbonylamino-8'-azabicyclo[4.3.0]non-4'-en-8'-yl)-6-fluoro-1,4-dihydro-4-oxo-3-quinolinecarboxylic acid

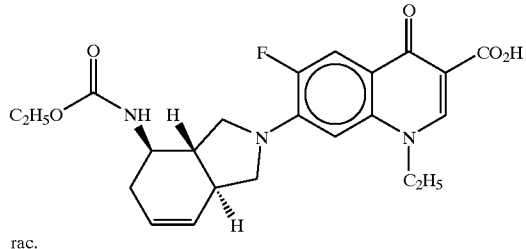

rac.

Heat 1.3 g (5 mmol) of 1-ethyl-6,7-difluoro-1,4-dihydro-4-oxo-3-quinolinecarboxylic acid, 0.6 g (5 mmol) of DABCO and 1.3 g (6 mmol) of the title compound from Example C to reflux for 3 h in a mixture consisting of 15 ml of acetonitrile and 7.5 ml of DMF. After cooling, add 10 ml of acetonitrile, 20 ml of water and 2.5 ml of acetic acid, and filter off the precipitate with suction, wash it with acetonitrile/water 1:1, and dry it at 50° C.

Yield: 2.1 g (95% of theory) Melting point: 293–295° C. Elementary analysis: ($C_{23}H_{26}$,$FN_3O_5$) Calculated C: 62.3 H: 5.9 N: 9.5 F: 4.3 Found C: 61.35 H: 6.05 N: 9.35 F: 4.1

$^1$H-NMR ($d_6$-DMSO): δ=8.82 (s, 1H); 7.77 (d, 1H); 7.35 (d, 1H); 6.62 (d, 1H); 5.88 (d, 1H); 5.70 (m, 1H); 4.49 (q, 2H); 4.03 (q, 2H); 3.70–3.86 (m, 3H); 3.48 (m, 1H); 3.28 (m, 1H); 2.48–2.69 (m, 2H); 1.94–2.07 (m, 2H); 1.41 (t, 3H); 1.20 ppm (t, 3H).

EXAMPLE 10

(1'SR,2'RS,6'SR)-7-(2'-Amino-8'-azabicyclo[4.3.0]non-4'-en-8'-yl)-1-ethyl-6-fluoro-1,4-dihydro-4-oxo-3-guinoline-carboxylic acid

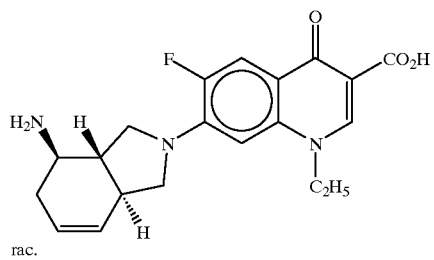

rac.

Heat 1.35 g (3 mmol) of the title compound from Example 9 to reflux for 4 h in a mixture consisting of 30 ml of 10% strength potassium hydroxide solution and 15 ml of 1,2-ethanediol. After cooling, add 30 ml of acetonitrile, adjust to a pH of 2 with 10% strength hydrochloric acid, and filter off the precipitate with suction, wash it with acetonitrile/water (1:1), and dry it at 50° C.

Yield: 1.20 g (98% of theory) of the title compound as hydrochloride Melting point: >300° C.

$^1$H-NMR ($CF_3CO_2D$): δ=9.14 (s, 1H); 8.17 (d, 1H); 6.92 (d, 1H); 6.05 (d, 1H); 5.89 (m, 1H); 4.75 (q, 2H); 4.36 (m, 1H); 4.21 (m, 1H); 4.04 (m, 1H); 3.92 (m, 1H); 3.64 (m, 1H); 3.00 (m, 1H); 2.92 (m, 1H); 2.50–2.63 (m, 2H); 1.78 ppm (t, 3H).

EXAMPLE 11

(1'SR,2'RS,6'SR)-8-Chloro-1-cyclopropyl-7-(2'-ethyloxy-carbonylamino-8'-azabicyclo[4.3.0]non-4'-en-8'-yl)-6-fluoro-1,4-dihydro-4-oxo-3-quinolinecarboxylic acid

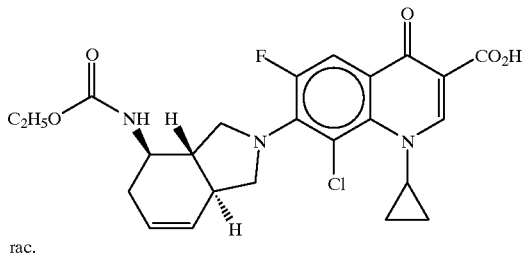

rac.

Heat 1.5 g (5 mmol) of 8-chloro-1-cyclopropyl-6,7-difluoro-1,4-dihydro-4-oxo-3-quinolinecarboxylic acid, 0.6 g (5 mmol) of DABCO and 1.3 g (6 mmol) of the title compound from Example C to reflux for 3 h in a mixture consisting of 15 ml of acetonitrile and 7.5 ml of DMF. After cooling, add 35 ml of water, adjust to pH 4 by adding acetic acid, and filter off the precipitate with suction, wash it with a little water, and dry it at 50° C.

Yield: 2.3 g (94% of theory) Melting point: 225–227° C. Elementary analysis: ($C_{24}H25$,$ClFN_3O_5$) Calculated C: 58.8 H: 5.1 N: 8.6 Cl: 7.2 F: 3.9 Found C: 58.55 H: 5.4 N: 8.65 Cl: 7.05 F: 4.05

$^1$H-NMR ($CDCl_3$): δ=8.86 (s, 1H); 7.92 (d, 1H); 5.85 (d, 1H); 5.74 (m, 1H); 4.65 (br., 1H); 4.30 (m, 1H); 4.07–4.19 (m, 3H); 4.04 (m, 1H); 3.86 (m, 1H); 3.57 (dd, 1H); 3.48 (dd, 1H); 2.64–2.78 (m, 2H); 1.98–2.12 (m, 2H); 1.39 (m,, 1H); 1.27 (m, 3H); 1.17 (m, 1H); 1.05 (m, 1H); 0.81 ppm (m, 1H)

EXAMPLE 12

(140 SR,2'RS,6'SR)-7-(2'-Amino-8'-azabicyclo[4.3.0]non-4'-en-8'-yl-8-chloro-1-cyclopropyl-6-fluoro-1,4-dihydro-4-oxo-3-quinolinecarboxylic acid

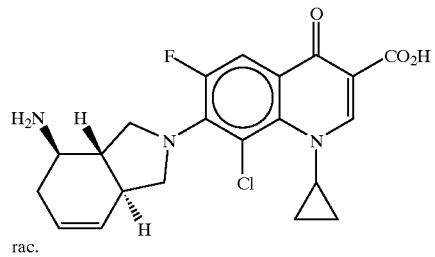

rac.

Heat 1.0 g (2 mmol) of the title compound from Example 11 to reflux for 3 h in a mixture consisting of 20 ml of 10% strength potassium hydroxide solution and 10 ml of 1,2-ethanediol. After cooling, adjust to a pH of 6 with 10% strength hydrochloric acid, and filter off the precipitate with suction, wash it with water, and dry it at 50° C.

Yield: 0.8 g (96% of theory) Melting point: >300° C.

$^1$H-NMR ($CF_3CO_2D$): δ=9.43 (s, 1H); 8.14 (d, 1H); 6.04 (d, 1H); 5.89 (m, 1H); 4.81 (m; 1H); 4.48 (m, 1H); 4.23 (m, 1H); 4.07 (m, 2H); 3.94 (m, 1H); 2.98 (m, 1H); 2.89 (m, 1H); 2.45–2.61 (m, 2H); 1.76 (m, 1H); 1.45 (m, 1H); 1.32 (m, 1H); 1.08 ppm (m, 1H).

EXAMPLE 13

(1'SR,2'RS,6'SR)-10-(2'-Ethyloxycarbonylamino-8'-azabicyclo[4.3.0]non-4'-en-8'-yl)-9-fluoro-2,3-dihydro-3-methyl-7-oxo-7H-pyrido[1,2,3-de][1,4]benzoxazine-6-carboxylic acid

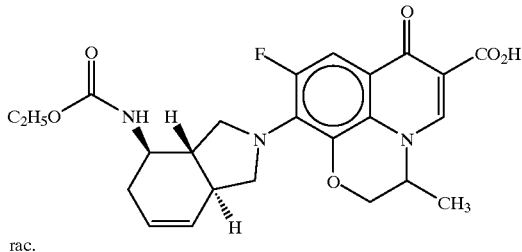

Heat 1.4 g (5 mmol) of 9,10-difluoro-2,3-dihydro-3-methyl-7-oxo-7H-pyrido[1,2,3-de][1,4]benzoxazine-6-carboxylic acid, 0.6 g (5 mmol) of DABCO and 1.3 g (6 mmol) of the title compound from Example C to reflux for 7 h in a mixture consisting of 15 ml of acetonitrile and 7.5 ml of DMF. After cooling, add 20 ml of acetonitrile, 20 ml of water and 2.5 ml of acetic acid, filter off the precipitate with suction, suspend it again in 40 ml of acetonitrile/water, stir vigorously, filter off the sediment with suction again, and wash it with a little water and dry it at 50° C.

Yield: 1.6 g (67% of theory) Melting point: 275–286° C.

$^1$H-NMR (d6-DMSO): δ=8.88 (s, 1H, H on C-5); 7.52 (d, 1H, H on C-8); 7.30 (d, 1H, NH); 5.84 (d, 1H, H on C-5'); 5.68 (m, 1H, H on C-4'); 4.88 (q, 1H, H on C-3); 4.53 (d, 1H, $H_a$ on C-2); 4.24 (d, 1H, $H_b$ on C-2); 4.00 (q, 2H, ethoxy CH$_2$); 3.71–3.83 (m, 3H), 3.66 (m, 1H), 3.58 (m, 1H): H on C-7'/9' and H on C-2'; 2.47–2.57 (m, 2H, $H_a$ on C-3' and H on C-6'); 2.00 (m, 1H, $H_b$ on C-3'); 1.89 (m, 1H, H on C-1'); 1.46 (d, 3H, CH$_3$ on C-3); 1.18 ppm (t, 3H, ethoxy CH$_3$).

EXAMPLE 14

(1'SR,2'RS,6'SR)-10-(2'-Amino-8'-azabicyclo[4.3.0]non-4'-en-8'-yl)-9-fluoro-2 3-dihydro-3-methyl-7-oxo-7H-pyrido[1,2,3-de][1,4]benzoxazine-6-carboxylic acid

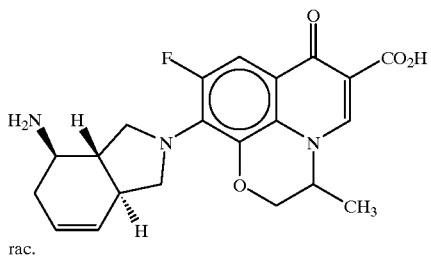

Heat 1.2 g (2.5 mmol) of the title compound—from Example 13 to reflux for 10 h in 25 ml of 10% strength potassium hydroxide solution. After cooling, add 10 ml of acetonitrile, adjust to a pH of 6–7 with 10% strength hydrochloric acid, and filter off the precipitate with suction, wash it with a little water, and dry it at 50° C.

Yield: 0.95 g (95% of theory) Melting point: >300° C.

$^1$H-NMR (CF$_3$CO$_2$D): δ=9.44 (2s, 1H); 8.18 (2d, 1H); 5.97 (m, 2H); 5.76 (m, 1H); 4.82–4.98 (m, 2H); 4.70 (m, 1H); 4.40–4.54 (m, 2H); 4.17 (m, 1H); 4.07 (t, 1H); 3.39 (m, 1H); 2.98–3.12 (m, 2H); 2.64 (m, 1H); 1.86 ppm (d, 3H).

EXAMPLE 15

(1'SR,2'RS,6'SR)-1-Cyclopropyl-7-(2'-ethyloxycarbonylamino-8'-azabicyclo[4.3.0]non-4'-en-8'-yl)-8-fluoro-1,4-dihydro-4-oxo-3-quinolinecarboxylic acid

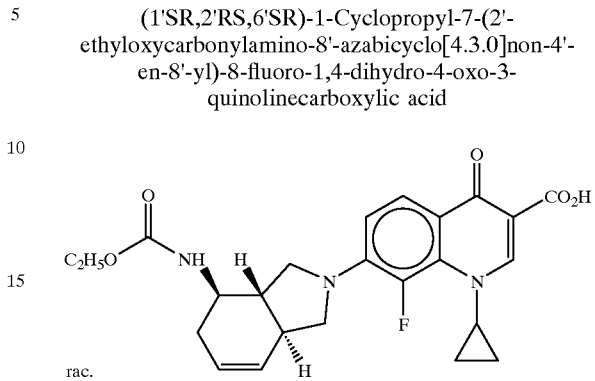

Heat 2.0 g (7.5 mmol) of 1-cyclopropyl-7,8-difluoro-4-oxo-3-quinolinecarboxylic acid, 1.7 g (15 mmol) of DABCO and 1.9 g (9 mmol) of the title compound from Example C at 100° C. for one hour in 75 ml of DMSO. Distil off the solvent under high vacuum, stir the residue with acetonitrile, filter off with suction, and dry at 100° C.

Yield: 3.1 g (90% of theory) Melting point: 278–280° C.

$^1$H-NMR (CF$_3$CO$_2$D): δ=9.20 (s, 1H, H on C-2); 8.32 (d, 1H, H on C-5); 7.39 (dd, 1H, H on C-6); 5.95 (d, 1H, H on C-5'); 5.88 (dd, 1H, H on C-4'); 4.40 (m, 3H, H on C-2', $H_a$ on C-7'and $H_a$ on C-9'); 4.15 (m, 3H, cyclopropyl CH and ethoxy CH$_2$); 3.85 (t, 1H, $H_b$ on C-7'); 3.64 (t, 1H, $H_b$ on C-9'); 2.85 (m, 2H, $H_a$ on C-3' and H on C-6'); 2.23 (m, 2H, H on C-1'and $H_b$ on C-3'); 1.55 (m, 2H, cyclopropyl CH$_2$); 1.42 ppm (m, 5H, cyclopropyl CH$_2$ and ethoxy CH$_3$).

EXAMPLE 16

(1'SR,2'RS,6'SR)-7-(2'-Amino-8'-azabicyclo[4.3.0]non-4'-en-8'-yl)-1-cyclopropyl-8-fluoro-1,4-dihydro-4-oxo-3-quinolinecarboxylic acid

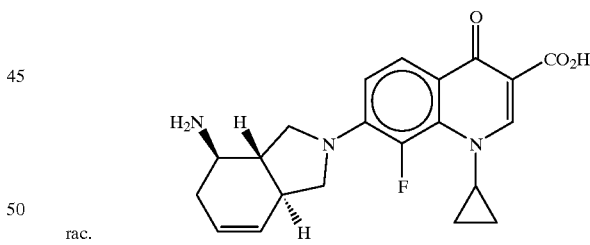

Heat 2.3 g (5 mmol) of the title compound from Example 15 to reflux for 6 h in a mixture consisting of 50 ml of 10% strength potassium hydroxide solution and 25 ml of 1,2-ethanediol. Add 50 ml of methanol and adjust to a pH of 4–5 with half-concentrated hydrochloric acid. Filter off the precipitate with suction, suspend it in 35 ml of methanol, adjust to pH 2–3 with hydrochloric acid, and, after the addition of 35 ml of water, stir thoroughly, filter off the sediment with suction again, and wash it with a little water and dry it at 100° C.

Yield: 1.6 g (84% of theory) of the title compound as a hydrochloride Melting point: >300° C.

$^1$H-NMR (CF$_3$CO$_2$D): δ=9.22 (s, 1H, H on C-2); 8.37 (d, 1H, H on C-5); 7.39 (dd, 1H, H on C-6); 6.05 (d, 1H, H on

C-5'); 5.89 (dd, 1H, H on C-4'); 4.47 (m, 1H), 4.38 (m, 1H), 4.18 (m, 1H), 4.05 (m, 1H): H on C-2', $H_a$ on C-7', $H_a$ on C-9' and cyclopropyl CH; 3.99 (t, 1H, $H_b$ on C-9'); 3.67 (t, 1H, $H_b$ on C-7'); 3.00 (m, 1H, $H_a$ on C-3'); 2.92 (m, 1H, H on C-6'); 2.55 (m, 2H, H on C-1'and $H_b$ on C-3'); 1.55 (m, 2H, cyclopropyl $CH_2$); 1.42 ppm (m, 2H, cyclopropyl $CH_2$).

EXAMPLE 17

(1'SR,2'RS,6'SR)-1-Cyclopropyl-7-(2'-ethyloxycarbonyl-amino-8'-azabicyclo[4.3.0]non-4'-en-8'-yl)-5,6,8-trifluoro-1,4-dihydro-4-oxo-3-quinolinecarboxylic acid

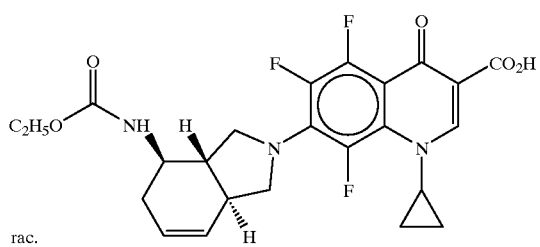

rac.

Heat 1.8 g (6 mmol) of 1-cyclopropyl-5,6,7,8-tetrafluoro-1,4-dihydro-4-oxo-3-quinolinecarboxylic acid, 0.7 g (6 mmol) of DABCO and 1.5 g (7.2 mmol) of the title compound from Example C to reflux for 3 h in a mixture consisting of 15 ml of acetonitrile and 7.5 ml of DMF. After cooling, add 20 ml of acetonitrile, 20 ml of water and 2.5 ml of acetic acid, filter off the precipitate with suction, suspend it in 40 ml of acetonitrile/water (1:1), filter off the sediment with suction again, and wash it with water, and dry it at 50° C.

Yield: 2.55 g (87% of theory) Melting point: 242–244° C. Elementary analysis: ($C_{24}H_{24}F_3N_3O_5$) Calculated C: 58.7 H: 4.9 N: 8.6 F: 11.6 Found C: 58.65 H: 5.2 N: 8.7 F: 11.35

$^1$H-NMR (CDCl$_3$): δ=8.66 (s, 1H); 5.84 (d, 1H); 5.75 (m, 1H); 4.15 (m, 1H); 3.82–4.05 (m, 4H); 3.77 (m, 1H); 3.56 (m, 1H); 2.72 (m, 1H); 2.62 (m, 1H); 1.96–2.10 (m, 2H); 1.28 (m, 3H); 1.06–1.24 ppm (m, 4H).

EXAMPLE 18

(1'SR,2'RS,6'SR)-5-Amino-1-cyclopropyl-7-(2'-ethyloxy-carbonylamino-8'-azabicyclo[4.3.0]non-4'-en-8'-yl)-6,8-fluoro-1,4-dihydro-4-oxo-3-quinolinecarboxylic acid

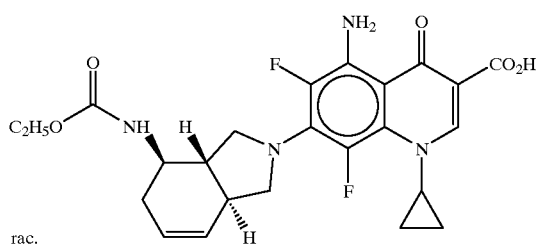

rac.

Initially introduce 2.5 g (2.5 mmol) of the title compound from Example 17 in 50 ml of DMSO, pass in ammonia gas for 8 h, and heat to 140° C. After cooling, add to 100 ml of water, adjust to pH 2–3 with 10% strength hydrochloric acid, and filter off the precipitate with suction, wash it with water, and dry it at 50° C.

Yield: 1.9 g (78% of theory) Melting point: 225–229° C.

$^1$H-NMR (d6-DMSO): δ=8.44 (s, 1H); 7.31 (d, 1H); 7.12 (br., 2H); 5.83 (d, 1H); 5.68 (m, 1H); 3.93–4.04 (m, 3H); 3.46–3.81 (m, 5H); 2.46–2.61 (m, 2H); 2.03 (m, 1H); 1.90 (m, 1H); 0.97–1.21 ppm (m, 7H).

EXAMPLE 19

(1'SR,2'RS,6'SR)-5-Amino-7-(2'-amino-8'-azabicyclo[4.3.0]non-4'-en-8'-yl)-1-cyclopropyl-6,8-difluoro-1,4-dihydro-4-oxo-3-quinolinecarboxylic acid

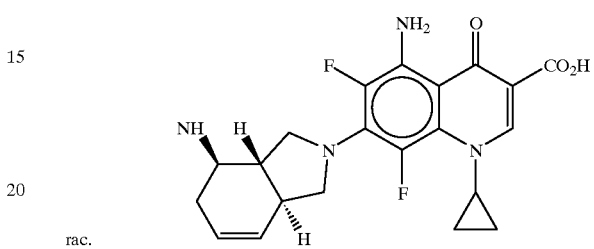

rac.

Heat 1.2 g (2.6 mmol) of the title compound from Example 18 to reflux for 15 h in a mixture consisting of 20 ml of 10% strength potassium hydroxide solution and 10 ml of 1,2-ethanediol. After cooling, add 10 ml of acetonitrile, adjust to a pH of 3–4 with 10% strength hydrochloric acid, allow to stand at 0° C. for 4 h, and filter off the precipitate with suction, wash it with a little water, and dry it at 50° C.

Yield: 1.1 g (95% of theory) of the title compound as hydrochloride Melting point: >300° C.

$^1$H-NMR (d$_6$-DMSO): δ=8.46 (s, 1H); 8.39 (br, 2H); 7.16 (br, 2H); 5.90 (d, 1H); 5.70 (m, 1H); 3.97 (m, 1H); 3.69–3.82 (m, 3H); 3.53 (m, 2H); 2.56–2.68 (m, 2H); 2.23 (m, 1H); 2.07 (m, 1H); 1.00–1.21 ppm (m, 7H).

EXAMPLE 20

Ethyl (1'SR,2'RS,6'SR)-1-cyclopropyl-7-(2'-ethyloxy-carbonylamino-8'-azabicyclo[4.3.0]non-4'-en-8'-yl)-6-fluoro-1,4-dihydro-4-oxo-1,8-naphthyridine-3-carboxylate

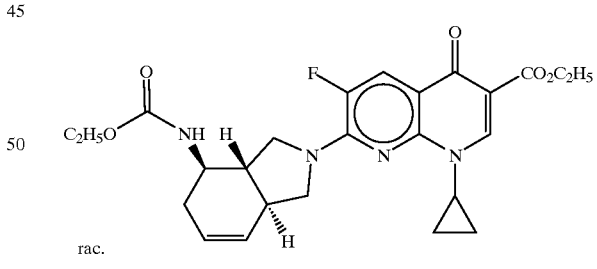

rac.

Stir 1.24 g (4 mmol) of ethyl 7-chloro-1-cyclopropyl-6-fluoro-1,4-dihydro-4-oxo-1,8-naphthyridine-3-carboxylate, 0.48 g (4 mmol) of DABCO and 0.84 g (6 mmol) of the title compound from Example C dissolved in 20 ml of acetonitrile at room temperature for 3 h. Add the mixture to water, extract with methylene chloride, dry the combined extracts with sodium sulphate, and concentrate. Purify the crude product by column chromatography on 100 g of silica gel (63–200 μm) using cyclohexane/acetone (1:1).

Yield: 0.5 g (26% of theory) $R_f$=0.18 Cyclohexane/acetone (1:1)

¹H-NMR (CDCl₃): δ=8.45 (s, 1H); 8.00 (d, 1H, J=13 Hz); 5.86 (d, 1H); 5.72 (m, 1H); 4.94 (br d, 1H); 4.38 (q, 2H); 3.86–4.25 (m, 5H); 3.33–3.70 (m, 3H); 2.50–2.84 (m, 2H); 1.90–2.15 (m, 2H); 0.80–1.34 ppm (m, 10H).

EXAMPLE 21

(1'SR,2'RS,6'SR)-7-(2'-Amino-8'-azabicyclo[4.3.0] non-4'-en-8'-yl)-1-cyclopropyl-6-fluoro-1,4-dihydro-4-oxo-1,8-naphthyridine-3-carboxylic acid

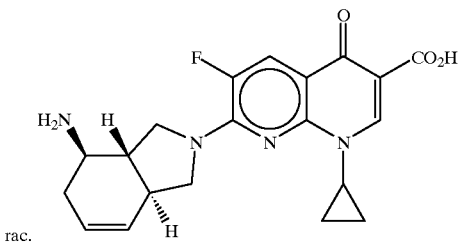

The title compound is obtained from 0.1 g (0.2 mmol) of the title compound from Example 20 in analogy with Example 10.

Yield: 0.08 g (95% of theory) of the title compound as hydrochloride Melting point: >300° C.

¹H-NMR (CF₃CO₂D): δ=9.17 (s, 1H); 8.14 (d, 1H); 6.05 (dd 1H); 5.89 (d, 1H); 4.46–4.78 (m, 3H); 3.55–4.15 (m, 3H); 2.82–3.04 (m, 2H); 2.42–2.64 (m, 2H); 1.58 (m, 2H); 1.30 ppm (m, 2H).

EXAMPLE 22

(1'SR,2'RS,6'SR)-1-Cyclopropyl-6,8-difluoro-1,4-dihydro-7-(2'-methylamino-8'-azabicyclo[4.3.0]non-4'-en-8'-yl)-4-oxo-3-quinolinecarboxylic acid

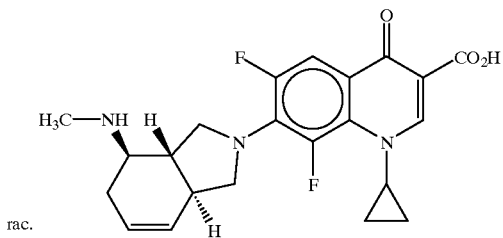

Heat 0.84 g (3 mmol) of 1-cyclopropyl-6,7,8-trifluoro-1,4-dihydro-4-oxo-3-quinolinecarboxylic acid, 0.68 g (6 mmol) of DABCO and 0.65 g (4.6 mmol) of the title compound from Example D to reflux for 21 h in a mixture consisting of 10 ml of acetonitrile and 5 ml of DMF. After cooling, add 20 ml of acetonitrile and 10 ml of water, adjust to a pH of 3–4 by adding 10% strength hydrochloric acid, filter off the precipitate with suction, suspend it in 30 ml of acetonitrile/water, and filter off the sediment with suction again, wash it with a little water, and dry it at 50° C.

Yield: 1.15 g (85% of theory) of the title compound as hydrochloride Melting point: >300° C.

¹H-NMR (CF₃CO₂D): δ=9.24 (s, 1H); 8.06 (d, 1H); 6.04 (d, 1H); 5.90 (m, 1H); 4.47 (m, 1H); 4.37 (m, 1H); 4.21 (m, 2H); 3.94 (m, 1H); 3.87 (m, 1H); 3.06 (s, 3H); 2.98 (m, 1H); 2.84 (m, 1H); 2.57 (m, 1H); 2.46 (m, 1H); 1.58 (m, 2H); 1.41 ppm (m, 2H).

EXAMPLE 23

(1'SR,2'RS,6'SR)-8-Chloro-1-cyclopropyl-6-fluoro-1,4-dihydro-7-(2'-methylamino-8'-azabicyclo[4.3.0] non-4'-en-8'-yl)-4-oxo-3-quinolinecarboxylic acid

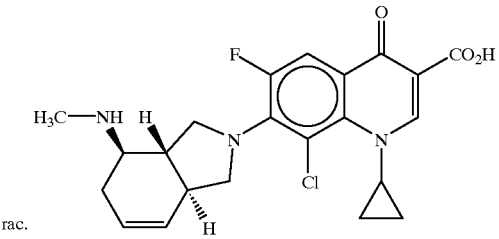

The title compound is obtained from 0.9 g (3 mmol) of 8-chloro-1-cyclopropyl-6,7-difluoro-1,4-dihydro-4-oxo-3-quinolinecarboxylic acid, 0.34 g (3 mmol) of DABCO and 0.61 g (3.6 mmol) of the title compound from Example D in analogy with Example 22.

Yield: 1.3 g (92% of theory) of the title compound as a hydrochloride Melting point: >300° C.

¹H-NMR (CF₃CO₂D): δ=9.43 (s, 1H); 8.15 (d, 1H); 6.06 (d, 1H); 5.92 (m, 1H); 4.81 (m, 1H); 4.51 (m, 1H); 4.24 (m, 1H); 4.14 (m, 1H); 3.87–3.98 (m, 2H); 3.05 (s, 3H); 2.88–3.03 (m, 2H); 2.48–2.63 (m, 2H); 1.74 (m, 1H); 1.47 (m, 1H); 1.33 (m, 1H); 1.12 ppm (m, 1H).

EXAMPLE 24

(1'SR,2'RS,6'SR)-1-(2,4-Difluorophenyl)-6-fluoro-1,4-dihydro-7-(2'-methylamino-8'-azabicyclo[4.3.0] non-4'-en-8'-yl)-4-oxo-3-quinolinecarboxylic acid

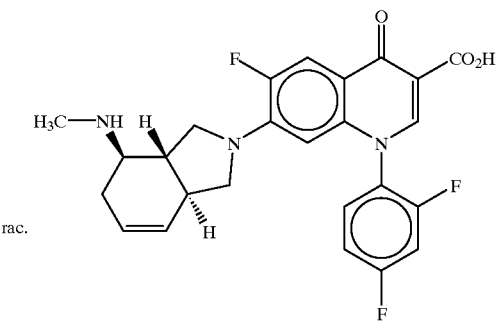

The title compound is obtained from 0.85 g (2.5 mmol) of 1-(2,4-difluorophenyl)-6-fluoro-1,4-dihydro-4-oxo-3-quinolinecarboxylic acid, 0.50 g (4.5 mmol) of DABCO and 0.76 g (5 mmol) of the title compound from Example D in analogy with Example 22.

Yield: 0.6 g (47% of theory) of the title compound as hydrochloride Melting point: >300° C.

¹H-NMR (CF₃CO₂D): δ=9.01 (s, 1H); 8.20 (d, 1H); 7.70 (m, 1H); 7.34 (m, 2H); 5.95 (d, 1H); 5.86 (m, 1H); 4.28 (m, 1H); 3.7–3.9 (m, 3H); 3.01 (s, 3H); 2.94 (m, 1H); 2.82 (m, 1H); 2.50 (m, 1H); 2.41 ppm (m, 1H).

EXAMPLE 25

(1'RS,2'RS,6'SR-1-Cyclopropyl-6,8-difluoro-1,4-dihydro-7-(2'-hydroxymethyl-8'-azabicyclo[4.3.0]non-4'-en-8'-yl)-4-oxo-3-quinolinecarboxylic acid

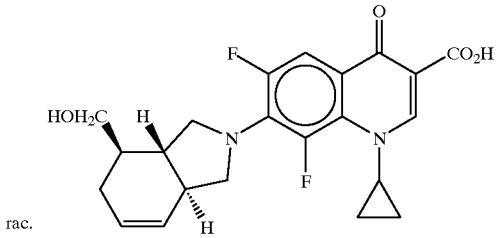

rac.

Heat 0.9 g (3 mmol) of 1-cyclopropyl-6,7,8-trifluoro-1,4-dihydro-4-oxo-3-quinolinecarboxylic acid, 0.35 g (3 mmol) of DABCO and 0.7 g (4.5 mmol) of the title compound from Example E to reflux for 4 h in a mixture consisting of 10 ml of acetonitrile and 5 ml of DMF. After cooling, add 10 ml of water and 1.5 ml of acetic acid, filter off the precipitate with suction, suspend it in 40 ml of acetonitrile/water (1:1), filter off the sediment with suction again, and dry it at 50° C.

Yield: 0.95 g (76% of theory) Melting point: 244–247° C.

$^1$H-NMR (d$_6$-DMSO): δ=8.58 (s, 1H); 7.67 (d, 1H); 5.87 (d, 1H); 5.75 (m, 1H); 4.07 (m, 1H); 3.78 (m, 2H); 3.68 (s, 1H); 3.27–3.52 (m, 3H); 2.40 (m, 1H); 2.23 (m, 1H); 1.82–1.95 (m, 2H); 1.62 (m, 1H); 1.08–1.23 ppm (m, 4H).

EXAMPLE 26

(1'RS,2'RS,6'SR)-1-Cyclopropyl-7-(2'-ethyloxycarbonyl-amminomethyl-8'-azabicyclo[4.3.0]non-4'-en-8'-yl)-6,8-difluoro-1,4-dihydro-4-oxo,3-quinolinecarboxylic acid

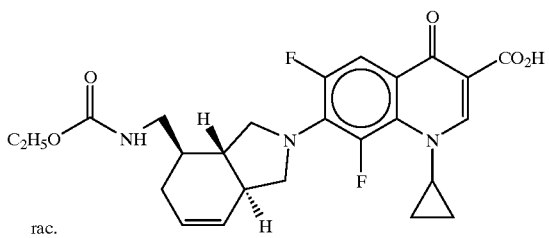

rac.

Heat 0.6 g (2.1 mmol) of 1-cyclopropyl-6,7,8-trifluoro-1,4-dihydro-4-oxo-3-quinolinecarboxylic acid, 0.25 g (2.1 mmol) of DABCO and 0.7 g (3.1 mmol) of the title compound from Example F to reflux for 3 h in a mixture consisting of 8 ml of acetonitrile and 4 ml of DMF. After cooling, add 10 ml of acetonitrile, 10 ml of water and 1 ml of acetic acid, filter off the precipitate with suction, suspend it in 20 ml of acetonitrile/water (1:1), filter off the sediment with suction again, and dry it at 50° C.

Yield: 0.8 g (79% of theory) Melting point: 220–222° C.

$^1$H-NMR (CDCl$_3$): δ=8.70 (s, 1H, H on C-2); 7.77 (d, 1H, H on C-5); 5.86 (d, 1H, H on C-5'); 5.77 (m, 1H, H on C-4'); 4.81 (br., 1H, NH); 4.13 (m, 2H, ethoxy CH$_2$); 3.96 (m, 1H, cyclopropyl CH); 3.77 (H on CH$_2$–NH and H$_a$ on C-9'); 3.60 (m, 1H, H$_a$ on C-7'); 3.36 (m, 1H, H$_b$ on C-9'); 3.14 (m, 1H, H$_b$ on C-7'); 2.37–2.51 (m, 2H, H$_a$ on C-3' and H on C-6'); 2.04 (m, 1H, H on C-2'); 1.94 (m, 1H, H$_b$ on C-3'); 1.73 (m, 1H, H on C-1'); 1.08–1.22 ppm (m, 7H, cyclopropyl CH$_2$ and ethoxy CH$_3$).

EXAMPLE 27

(1'RS,2'RS,6'SR)-7-(2'-Aminomethyl-8'-azabicyclo[4.3.0]non-4'-en-8'-yl)-1-cyclopropyl-6,8-difluoro-1,4-dihydro-4-oxo-3-guinolinecarboxylic acid

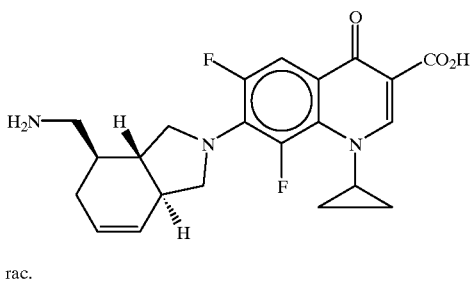

rac.

Heat 0.75 g (1.5 mmol) of the title compound from Example 26 to reflux for 3 h in a mixture consisting of 15 ml of 10% strength potassium hydroxide solution and 4 ml of 1,2-ethanediol. After cooling, add 15 ml of acetonitrile, adjust to a pH of 2–3 with 10% strength hydrochloric acid, and filter off the precipitate with suction, wash it with acetonitrile/water (1:1), and dry it at 50° C.

Yield: 0.6 g (90% of theory) of the title compound as hydrochloride Melting point: 236–240° C.

$^1$H-NMR (CF$_3$CO$_2$D): δ=9.24 (s, 1H); 8.06 (d, 1H); 6.01 (d, 1H); 5.90 (m, 1H); 4.47 (m, 1H); 4.18 (m, 2H); 4.06 (m, 1H); 3.88 (m, 1H); 3.58 (d, 1H); 3.28 (t, 1H); 2.73 (m, 2H); 2.50 (m, 1H); 2.18 (m, 1H); 2.00 (m, 1H); 1.56 (m, 2H); 1.42 ppm (m, 2H).

EXAMPLE 28

(1'RS,2'SR,6'RS)-1-Cyclopropyl-6,8-difluoro-1,4-dihydro-7-(2'-hydroxymethyl-8'-azabicyclo[4.3.0]non-4'-en-8'-yl)-4-oxo-3-quinolinecarboxylic acid

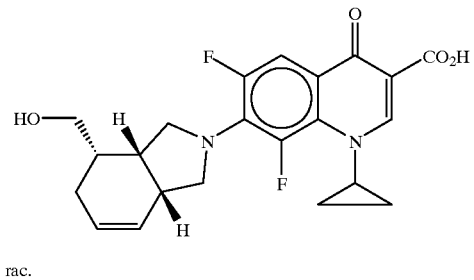

rac.

The title compound is obtained from 0.59 g (3 mmol) of 1-cyclopropyl-6,7,8-trifluoro-1,4-dihydro-4-oxo-3-quinolinecarboxylic acid and 0.69 g (4.5 mmol) of the title compound from Example G in analogy with Example 9.

Yield: 1.1 g (88% of theory) Melting point: 270–272° C. Elementary analysis: (C$_{22}$H$_{22}$F$_2$N$_2$O$_4$) Calculated C: 63.5 H: 5.3 N: 6.7 F: 9.1 Found C: 63.85 H: 5.5 N: 6.7 F: 8.8

$^1$H-NMR (d$_6$-DMSO): δ=8.58 (s, 1H); 7.66 (d, 1H); 5.77 (m, 1H); 5.55 (d, 1H); 4.06 (m, 2H); 3.68 (m, 1H); 3.47 (m, 2H); 3.28–3.42 (m, 3H); 2.88 (m, 1H); 2.66 (m, 1H); 2.06 (m, 2H); 1.83 (m, 1H); 1.08–1.24 ppm (m, 4H).

EXAMPLE 29

(1'RS,2'SR,6'RS)-1-Cyclopropyl-7-(2'-ethyloxycarbonyl-aminomethyl-8'-azabicyclo[4.3.0]]non-4'-en-8'-yl)-6,8-difluoro-1,4-dihydro-4-oxo-3-quinolinecarboxylic acid

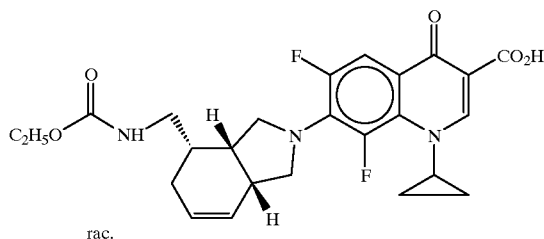

rac.

The title compound is obtained from 0.63 g (2.23 mmol) of 1-cyclopropyl-6,7,8-trifluoro-1,4-dihydro-4-oxo-3-quinolinecarboxylic acid and 0.60 g (2.68 mmol) of the title compound from Example H in analogy with Example 9.

Yield: 0.7 g (65% of theory) Melting point: 226–229° C.

$^1$H-NMR (CDCl$_3$): δ=8.71 (s, 1H); 7.76 (d, 1H); 5.79 (m, 1H); 5.54 (d, 1H); 4.91 (br, 1H); 4.12 (m, 3H); 3.96 (m, 1H); 3.79 (m, 1H); 3.56 (m, 1H); 3.47 (m, 1H); 3.18 (m, 2H); 2.91 (m, 1H); 2.65 (m, 1H); 2.20 (m, 2H); 1.91 (m, 1H); 1.08–1.33 ppm (m, 7H).

EXAMPLE 30

(1'RS,2'SR,6'RS)-7-(2'-Aminomethyl-8'-azabicyclo[4.3.0]non-4'-en-8'-yl)-1-cyclopropyl-6,8-difluoro-1,4-dihydro-4-oxo-3-quinolinecarboxylic acid

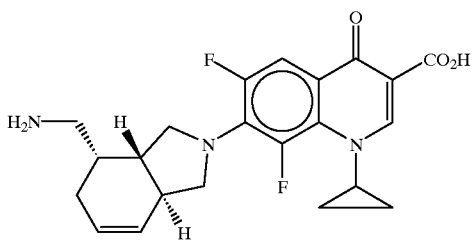

rac.

The title compound is obtained from 0.48 g (1.0 mmol) of the title compound from Example 29 in analogy with Example 10.

Yield: 0.39 g (86% of theory) of the title compound as hydrochloride Melting point: 304° C.

$^1$H-NMR (CF$_3$CO$_2$D): δ=9.20 (s, 1H); 8.02 (d, 1H); 5.91 (m, 1H); 5.68 (d, 1H); 4.43 (m, 2H); 4.12 (m, 1H); 3.94 (m, 1H); 3.87 (m, 1H); 3.28–3.42 (m, 2H); 3.14 (m, 1H); 2.87 (m, 1H); 2.67 (m, 1H); 2.46 (m, 1H); 2.12 (m, 1H); 1.56 (m, 2H); 1.38 ppm (m, 2H).

EXAMPLE 31

(1'SR,2'RS,3'RS,6'SR)-1-Cyclopropyl-7-(2'-ethyloxy-carbonylamino-3'-methyl-8'-azabicyclo[4.3.0]non-4'-en-8'-yl) -6,8-difluoro-1,4-dihydro-4-oxo-3-quinolinecarboxylic acid

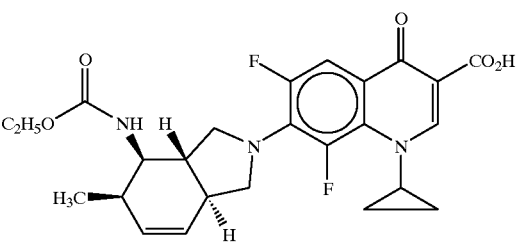

rac.

The title compound is obtained from 0.59 g (2.1 mmol) of 1-cyclopropyl-6,7,8-trifluoro-1,4-dihydro-4-oxo-3-quinolinecarboxylic acid and 0.6 g (2.6 mmol) of the title compound from Example I in analogy with Example 9.

Yield: 0.8 g (78% of theory) Melting point: 258–259° C.

EXAMPLE 32

(1'SR,2'RS,3'RS,6'SR)-7-(2'-Amino-3'-methyl-8'-azabicyclo[4.3.0]non-4'-en-8'-yl)-1-cyclopropyl-6,8-difluoro-1,4-dihydro-4-oxo-3-quinolinecarboxylic acid

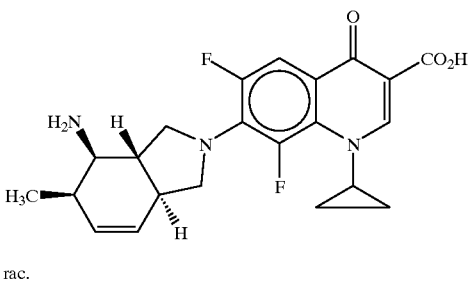

rac.

The title compound is obtained from 0.6 g (1.23 mmol) of the title compound from Example 31 in analogy with Example 10.

Yield: 0.55 g (99% of theory) of the title compound as hydrochloride Melting point: >300° C.

$^1$H-NMR (CF$_3$CO$_2$D): δ=9.24 (s, 1H); 8.06 (d, 1H); 5.98 (d, 1H); 5.86 (m, 1H); 4.47 (m, 1H); 4.07–4.32 (m, 3H); 3.95 (m, 1H); 3.10 (m, 1H); 2.82 (m, 1H); 2.50 (m, 1H); 1.57 (m, 2H); 1.40 (m, 2H); 1.32 ppm (d, 3H).

EXAMPLE 33

(1'SR,2'RS,6'SR)-1-Ethyl-7-(2'-ethyloxycarbonylamino-8'-azabicyclo[4.3.0]non-4'-en-8'-yl)-68-difluoro-1,4-dihydro-4-oxo-3-quinolinecarboxylic acid

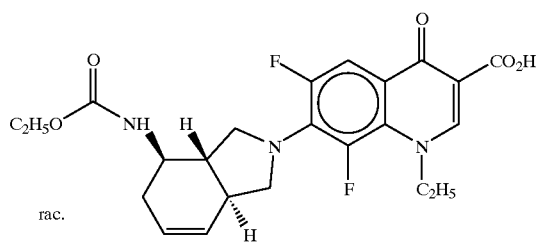

The title compound is obtained from 1.12 g (4.16 mmol) of 1-ethyl-6,7,8-trifluoro-1,4-dihydro-4-oxo-3-quinolinecarboxylic acid and 1.05 g (5.0 mmol) of the title compound from Example C in analogy with Example 9.

Yield: 1.9 g (99% of theory) Melting point: 285–287° C.

EXAMPLE 34

(1'SR,2'RS,6'SR)-7-(2'-Amino-8'-azabicyclo[4.3.0]non-4'-en-8'-yl)-1-ethyl-6,8-difluoro-1,4-dihydro-4-oxo-3-quinolinecarboxylic acid

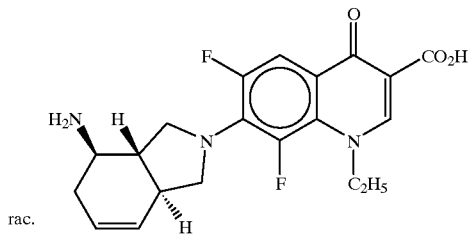

The title compound is obtained from 0.6 g (1.23 mmol) of the title compound from Example 33 in analogy with Example 10.

Yield: 1.44 g (97% of theory) of the title compound as hydrochloride Melting point; >300° C.

$^1$H-NMR (CF$_3$CO$_2$D): δ=9.12 (s, 1H); 8.10 (d, 1H); 6.02 (d, 1H); 5.88 (m, 1H); 4.94 (m, 2H); 4.37 (m, 1H); 4.21 (m, 2H); 4.03 (m, 1H); 3.95 (m, 1H); 2.99 (m, 1H); 2.83 (m, 1H); 2.58 (m, 1H); 2.49 (m, 1H); 1.78 ppm (t, 3H).

EXAMPLE 35

(1'SR, 2'RS, 6'SR)-8-Chloro-1-cyclopropyl-7-(2'-ethyloxy-carbonylamino-8'-azabicyclo[4.3.0]non-4'-en-8'-yl) -1,4-dihydro-4-oxo-3-quinolinecarboxylic acid

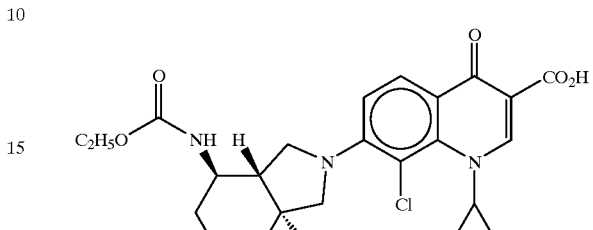

Heat 1.06 g (3.75 mmol) of 8-chloro-1-cyclopropyl-7-fluoro-4-oxo-3-quinolinecarboxylic acid, 0.84 g (7.5 mmol) of DABCO and 0.95 g (4.5 mmol) of the title compound from Example C at 100° C. for 4 h in 35 ml of DMSO. Distil off the solvent under high vacuum, stir the residue with acetonitrile, filter off with suction and dry at 100° C.

Yield: 1.5 g (85% of theory) Melting point: 260–261° C.

EXAMPLE 36

(1'SR,2'RS,6'SR)-7-(2'-Amino-8'-azabicyclo[4.3.0]non-4'-en-8'-yl)-8-chloro-1-cyclopropyl-1,4-dihydro-4-oxo-3-quinolinecarboxylic acid

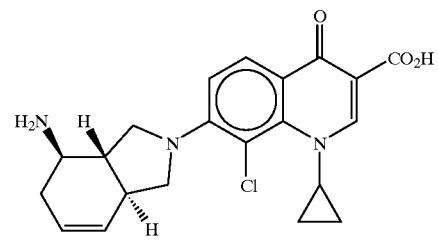

The title compound is obtained from 1.5 g (3.2 mmol) of the title compound from Example 35 in analogy with Example 16.

Yield: 0.72 g (52% of theory) of the title compound as hydrochloride Melting point: >300° C.

EXAMPLE 37

6,8-Difluoro-1-[(1RS,2SR)-2-fluorocyclopropyl]-1,4-dihydro-7-[(1'SR,2'RS,6'SR)-2'-methylamino-8'-azabicyclo[4.3.0]non-4'-en-8'-yl]-4-oxo-3-quinolinecarboxylic acid and 6,8-difluoro-1-[-(1SR,2RS)-2-fluorocyclopropyl]-1,4-dihydro-7-[(1'SR,2'RS,6'SR)-2'-methylamino-8'-azabicyclo[4.3.0]non-4'-en-8'-yl]-4-oxo-3-quinolinecarboxylic acid

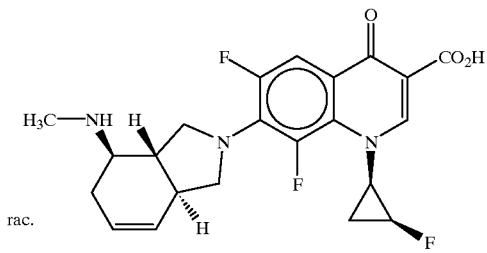

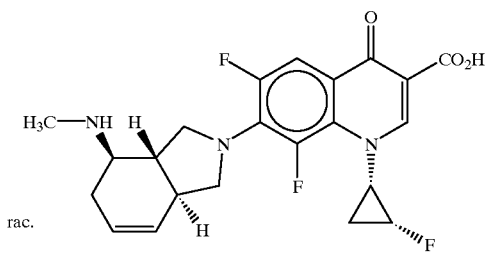

Heat 151 mg (0.5 mmol) of 6,7,8-trifluoro-1-[(1RS,2SR)-2-fluorocyclopropyl]-1,4-dihydro-4-oxo-3-quinolinecarboxylic acid, 63 mg (0.55 mmol) of DABCO and 84 mg (0.55 mmol) of the title compound from Example D to reflux for 1 h in a mixture consisting of 2 ml of acetonitrile and 1 ml of DMF. After cooling, filter off the suspension with suction, suspend the precipitate in 30 ml of water, filter off the sediment with suction again, and dry it at 70° C.

Yield: 93 mg (43% of theory) Melting point: >300° C.

$^1$H-NMR (CF$_3$CO$_2$D): δ=9.20 and 9.24 (2s, 1H); 8.08 (d, 1H); 6.04 (d, 1H); 5.90 (m, 1H); 5.14 (dm, 1H); 4.38 (m, 1H); 4.32 (m, 1H); 4.20 (m, 2H); 3.82–3.98 (m, 2H); 3.05 (s, 3H); 2.98 (m, 1H); 2.84 (m, 1H); 2.56 (m, 1H); 2.43 (m, 1H); 1.78–2.04 ppm (m, 2H).

EXAMPLE 38

8-chloro-6-fluoro-1-[(1RS,2SR)-2-fluorocyclopropyl]-1,4-dihydro-7-[(1'SR,2'RS,6'SR)-2'-methylamino-8'-azabicyclo[4.3.0]non-4'-en-8'-yl]-4-oxo-3-quinolinecarboxylic acid and 8-Chloro-6-fluoro-1-[(1SR,2RS)-2-fluorocyclopropyl]-1,4-dihydro-7-[(1'SR,2'RS,6'SR)-2'-methylamino-8'-azabicyclo[4.3.0]non-4'-en-8'-yl]-4-oxo-3-quinolinecarboxylic acid

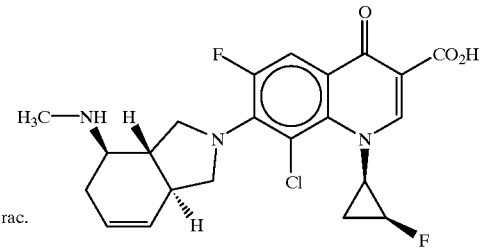

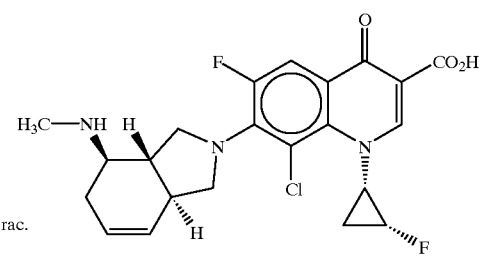

The title compound is obtained from 159 mg (0.5 mmol) of 8-chloro-6.7-difluoro-1-[(1RS,2SR)-2-fluorocyclopropyl]-1,4-dihydro-4-oxo-3-quinolinecarboxylic acid and 84 mg (0.55 mmol) of the title compound from Example D in analogy with Example 37.

Yield: 130 mg (58% of theory) Melting point: 247–249° C.

$^1$H-NMR (CF$_3$CO$_2$D): δ=9.22 and 9.43 (d and s, 1H); 8.16 (d, 1H); 6.05 (d, 1H); 5.92 (m, 1H); 5.07 and 5.20 (2dm, 1H); 4.64 and 4.80 (2m, 1H); 4.41–4.54 (m, 1H); 4.18 and 4.26 (2m, 1H); 4.07 (m, 1H); 3.86–3.97 (m, 2H); 3.06 (s, 3H); 2.98 (m, 1H); 2.90 (m, 1H); 2.55 (m, 1H); 2.47 (m, 1H); 1.88 and 2.07 (2m, 1H); 1.43 and 1.72 ppm (2m, 1H).

EXAMPLE 39

6,8-Difluoro-1[(1RS,2SR)-2-fluorocyclopropyl]-1,4-dihydro-7-[(1'SR,2'RS,6'SR)-2'-ethyloxycarbonylamino-8'-azabicyclo[4.3.0]non-4'-en-8'-yl]-4-oxo-3-quinolinecarboxylic acid and 6,8-difluoro-1[(1SR,2RS)-2-fluorocyclopropyl]-1,4-dihydro-7-[(1'SR,2'RS,6'SR)-2'-ethyloxycarbonylamino-8'-azabicyclo[4.3.0]non-4'-en-8'-yl]-4-oxo-3-quinolinecarboxylic acid

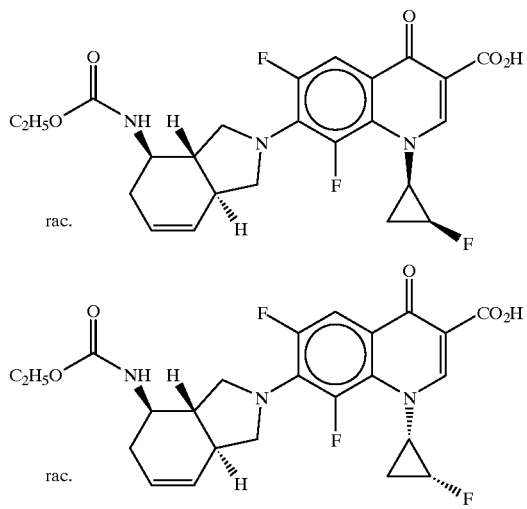

The title compound is obtained from 301 mg (1 mmol) of 6,7,8-trifluoro-1-[(1RS,2SR)-2-fluorocyclopropyl]-1,4-dihydro-4-oxo-3-quinolinecarboxylic acid and 231 mg (1.1 mmol) of the title compound from Example C in analogy with Example 37.

Yield: 428 mg (89% of theory) Melting point: 282–283° C.

$^1$H-NMR (CF$_3$CO$_2$D): δ=9.16 and 9.22 (2s, 1H); 8.04 (d, 1H); 5.91 (d, 1H); 5.85 (m, 1H); 5.13 (dm, 1H); 4.37 (m, 3H); 4.16 (m, 4H); 3.91 (m, 1H); 2.72–2.87 (m, 2H); 2.20 (m, 2H); 1.66–2.04 (m, 2H) 1.42 ppm (t, 3H).

EXAMPLE 40

(1'RS,2'RS, 6'SR)-8-Chloro-1-cyclopropyl-7-(2'-ethoxy carbonylaminomethyl-8'-azabicyclo[4.3.0]non-4'-en-8'-yl)-6-fluoro-1,4-dihydro-4-oxo-3-quinolinecarboxylic acid

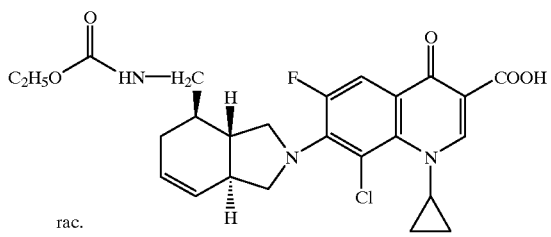

The title compound is obtained by reacting 8-chloro-1-cyclopropyl-6,7-difluoro-1,4-dihydro-4-oxo-3-quinolinecarboxylic acid with the title compound from Example F, as described in Example 26.

Yield: quantitative $^1$H-NMR (DMSO-d$_6$): 8.81 (s, 1H, 2-H); 7.89 (d, 1H, 5-H); 7.19 (t, 1H, carbamate-NH); 5.71; 5.58 (2m, 2x 1H, HC=CH); 4.38 (m, 1H, cyclopropyl-H); 3.99 (q, 2H, ethyl-CH$_2$); 3.45–3.40 (m, 3H); 3.12 (m, 1H); 3.00 (m, 2H); 2.30 (m, 2H); 2.12 (m, 1H); 1.96–1.87 (m, 2H); 1.20–1.11 (m, 5H, 2x cyclopropyl-H, ethyl-CH$_3$); 1.00–0.90 ppm (m, 2H, 2x cyclopropyl-H).

EXAMPLE 41

(1'RS,2'RS,6'SR)-7-(2'-Aminomethyl-8'-azabicyclo[4.3.0]non-4'-en-8'-yl)-8-chloro-1-cyclopropyl-6-fluoro-1,4-dihydro-4-oxo-3-quinolinecarboxylic acid

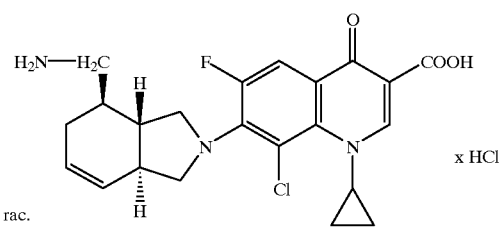

The product from Example 40 is reacted as described in Example 27.

Yield: 82% of theory, hydrochloride.

$^1$H-NMR (DMSO-d$_6$): 8.82 (s, 1H, 2-H); 7.91 (d, 1H, 5-H); 5.88; 5.60 (2 m, 2x 1H, HC=HC); 4.39 (m, 1H, cyclopropyl-H); 3.45–3.35 (m, 3H); 3.18 (m, 1H); 2.80 (m, 2H); 2.46 (m, 1H); 2.31 (m, 1H); 2.19 (m, 1H); 2.06 (m, 2H) 1.19; 0.95 ppm (2m, 2x 2H, 4x cyclopropyl-H).

EXAMPLE 42

(1'RS,2'RS,6'SR)-1-Cyclopropyl-7-(2'-ethoxycarbonylaminomethyl-8'-azabicyclo[4.3.0]-non-4'-en-8'-yl)-6-fluoro-1,4-dihydro-4-oxo-3-quinolinecarboxylic acid

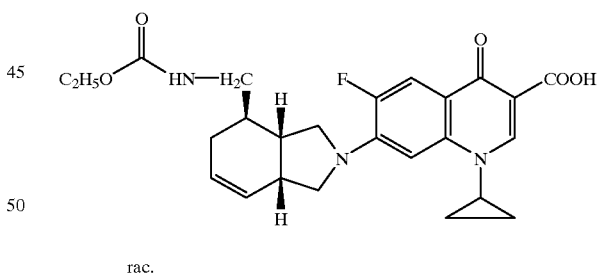

The title compound is obtained by reacting 1-cyclopropyl-6,7-difluoro-1,4-dihydro-4-oxo-3-quinolinecarboxylic acid with the title compound from Example F, as described in Example 26.

Yield: 95% of theory.

$^1$H-NMR (DMSO-d$_6$): 8.61 (s, 1H, 2-H); 7.81 (d, 1H, 5-H), 7.49 (d, 1H, 8-H); 7.21 (t, 1H, carbamate-NH); 5.80; 5.63 (2m, 2x 1H, HC=CH); 4.00 (q, 2H, ethyl-CH$_2$); 3.82–3.78 (m, 2H), 3.63 (m, 1H); 3.18–3.00 (m, 4H); 2.38 (m, 2H); 2.00 (m, 2H); 1.89 (m, 1H); 1.30 (m, 2H, 2x cyclo-propyl-H); 1.17 ppm (m, 5H, 2x cyclopropyl-H, ethyl-CH$_3$).

EXAMPLE 43

(1'RS,2'RS,6'SR)-7-(2'-Aminomethyl-8'-azabicyclo[4.3.0]-non-4'-en-8'-yl)-1-cyclopropyl-6-fluoro-1,4-dihydro-4-oxo-quinolinecarboxylic acid

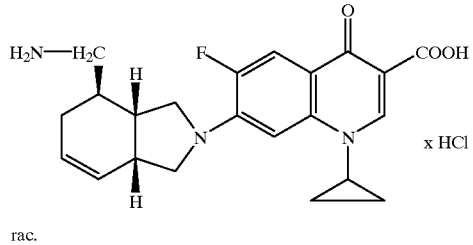

rac.

The product from Example 42 is reacted as described in Example 27.

Yield: 72% of theory, hydrochloride.

$^1$H-NMR (DMSO-$d_6$): 8.64 (s, 1H, 2-H); 7.87 (d, 1H, 5-H), 7.51 (d, 1H, 8-H); 5.84; 5.68 (2m, 2x 1H, HC=CH); 3.84–3.78 (m, 2H); 3.68 (m, 1H); 3.17 (m, 1H); 3.09 (m, 1H); 2.81 (m, 2H); 2.53 (m, 2H); 2.36 (m, 1H); 2.19 (m, 1H); 2.05 (m, 1H); 1.31; 1.19 ppm (2m, 2x 2H, 4x cyclopropyl-H).

EXAMPLE 44

(1'RS,2'RS,6'RS)-1-Cyclopropyl-7-(2'-ethoxycarbonyl-aminomethyl-8'-azabicyclo[4.3.0]-non-4'-en-8'-yl)-6,8-difluoro-1,4-dihydro-4-oxo-3-quinolinecarboxylic acid

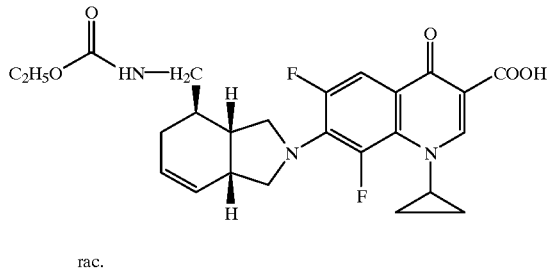

rac.

The title compound is obtained by reacting 1-cyclopropyl-6,7,8-trifluoro-1,4-dihydro-4-oxo-3-quinolinecarboxylic acid with the title compound from Example K, as described in Example 26.

Yield: 91% of theory.

$^1$H-NMR (CDCl$_3$): 8.71 (S, 1H, 2-H); 7.80 (d, 2H, 5-H); 5.80; 5.67 (2m, 2x 1H, HC=CH); 4.80 (t, 1H, carbamate-NH); 4.12 (q, 2H, ethyl-CH$_2$); 3.97 (m, 2H); 3.86 (m, 1H); 3.81 (m, 1H); 3.54 (m, 1H); 3.37 (m, 1H); 3.18 (m, 1H); 2.86 (m, 1H); 2.38–2.25 (m, 2H); 2.00–1.90 (m, 2H); 1.30–1.20 (m, 5H, 2x cyclopropyl-H, ethyl-CH$_3$); 1.14 ppm (m, 2H, 2x cyclopropyl-H).

EXAMPLE 45

(1'RS,2'RS,6'RS)-7-(2'-Aminomethyl-8'-azabicyclo[4.3.0-non-4'-en-8'-yl)-1-cyclopropyl-6,8-difluoro-1,4-dihydro-4-oxo-3-quinolinecarboxylic acid

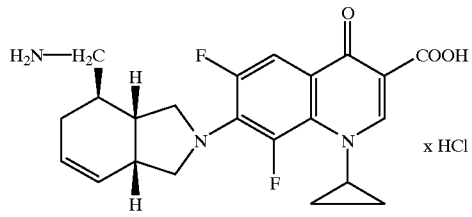

rac.

The product from Example 44 is reacted as described in Example 27.

Yield: 84% of theory, hydrochloride.

$^1$H-NMR (CF$_3$COOD): 9.21 (s, 1H, 2-H); 8.04 (d, 1H, 5-H); 5.91; 5.80 (2m, 2x 1 H, HC=CH); 4.45 (m, 1H); 4.35 (m, 1H); 4.18 (m, 2H); 3.92 (m, 1H); 3.55 (m, 1H); 3.35 (m, 1H); 3.08 (m, 1H); 2.69–2.58 (m, 2H); 2.47 (m, 1H); 2.19 (m, 1H); 1.57; 1.40 ppm (2m, 2x 2H, 4x cyclopropyl-H).

EXAMPLE 46

(1'RS,2'RS,6'RS)-8-Chloro-1-cyclopropyl-7-(2'-ethoxy-carbonylaminomethy-8'-azabicyclo[4.3.0]non-4'-en-8'-yl)-6-fluoro-1,4-dihydro-4-oxo-quinolinecarboxylic acid

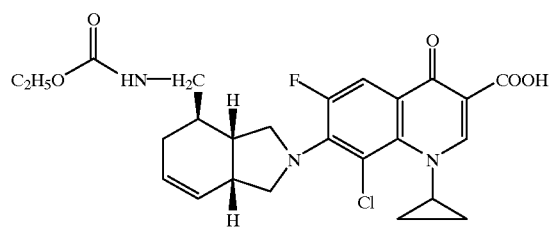

rac.

The title compound is obtained by reacting 8-chloro-1-cyclopropyl-6,7-difluoro-1,4-dihydro-4-oxo-3-quinolinecarboxylic acid with the title compound from Example K, as described in Example 26.

Yield: quantitative. Melting point: >300° C.

EXAMPLE 47

(1'RS,2'RS,6'RS)-7-(2'-Aminomethyl-8'-azabicyclo[4.3.0]non-4'-en-8'-yl)-8-chloro-1-cyclopropyl-6-fluoro-1,4-dihydro-4-oxo-3-quinolinecarboxylic acid

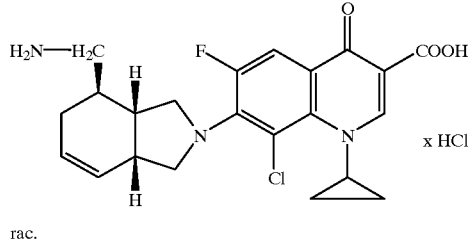

The product from Example 46 is reacted as described in Example 27.

Yield: 58% of theory, hydrochloride. Melting point: >300° C.

EXAMPLE 48

(1'RS,2'RS,6'RS)-7-(2'-Aminomethyl-8'-azabicyclo[4.3.0]non-4'-en-8'-yl)-1-cyclopropyl-6-fluoro-1,4-dihydro-4-oxo-quinolinecarboxylic acid

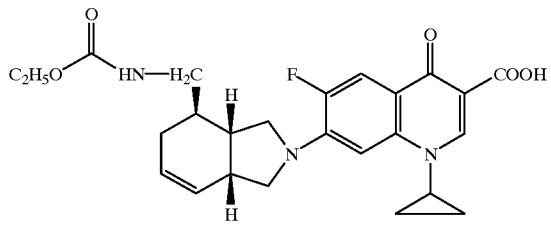

The title compound is obtained by reacting 1-cyclopropyl-6,7-difluoro-1,4-dihydro-4-oxo-3-quinolinecarboxylic acid with the title compound from Example K, as described in Example 26.

Yield: 75% of theory. Melting point: >300° C.

EXAMPLE 49

(1'RS,2'RS,6'RS)-7-(2'-Aminomethyl-8'azabicyclo[4.3.0]non-4'-en-8'-yl)-1-cyclopropyl-6-fluoro-1,4-dihydro-4-oxo-3-quinolinecarboxylic acid

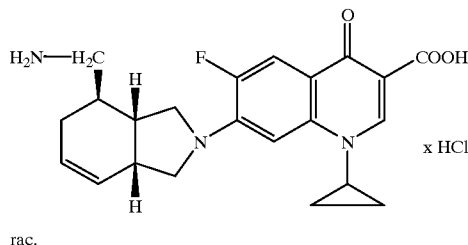

The product from Example 48 is reacted as described in Example 27.

Yield: 77% of theory, hydrochloride. Melting point: >300° C.

EXAMPLE 50

(1'RS,2'RS,6'RS)-10-(2-Ethoxycarbonylaminomethyl-8'-azabicyclo[4.3.0]non-4'-en-8'-yl)-9-fluoro-2,3-dihydro-3-methyl-7-oxo-7H-pyrido[1,2,3-de][1,4]benzoxazine-6-carboxylic acid

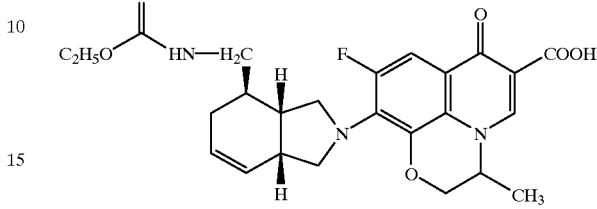

The title compound is obtained by reacting 9,10-difluoro-2,3-dihydro-3-methyl-7-oxo-7H-pyrido[1,2,3-de)][1,4]benzoxazine-6-carboxylic acid with the title compound from Example K, as described in Example 13.

Yield: 80% of theory. pelting point: 190° C.

EXAMPLE 51

(1'RS,2'RS,6'RS)-10-(2'-Aminomethyl-8'-azabicyclo[4.3.0]non-4'-en-8'-yl)-9-fluoro-2,3-dihydro-3-methyl-7-oxo-7H-pyrido[1,2,3-de][1,4]benzoxazine-6-carboxylic acid

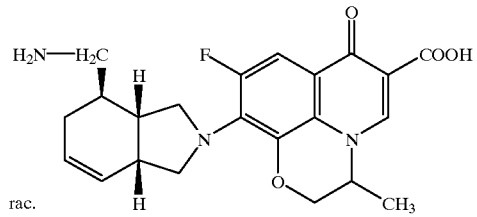

The product from Example 50 is reacted as described in Example 14.

Yield: 95% of theory, hydrochloride. Melting point: >300° C.

EXAMPLE 52

Ethyl (1'RS,2'RS,6'RS)-1-cyclopropyl-7-(2'-ethyloxy-carbonylaminomethyl-8'-azabicyclo[4.3.0]non-4'-en-8'-yl)-6-fluoro-1,4-dihydro-4-oxo-1,8-naphthyridine-3-carboxylate

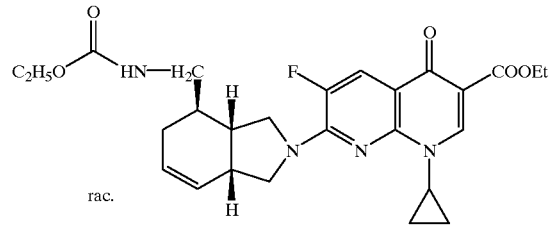

A mixture consisting of 828 mg (2.6 mmol) of ethyl 7-chloro-1-cyclopropyl-6-fluoro-1,4-dihydro-4-oxo-1,8- naphthyridine-3-carboxylate, 900 mg (4 mmol) of the product from Example K and 20 ml of acetonitrile is stirred at room temperature for three days. Subsequently, insoluble components are filtered off with suction and the solution is concentrated in vacuo. The crude product is purified by chromatography (eluent: dichloromethane/methanol/conc. ammonia 15:4:0.5).

Yield: 700 mg (56% of theory).

$^1$H-NMR (DMSO-d$_3$): 8.36 (s, 1H, 2-H); 7.81 (d, 1H, 5-H); 7.21 (t, 1H, carbamate-NH); 5.73; 5.67 (2m, 2x 1H, HC=CH); 4.20; 3.99 (2q, 2x 2H, 2x ethyl-CH$_2$); 3.86 (m, 1H); 3.78 (m, 1H); 3.56 (m, 2H); 3.13–3.01 (m, 2H); 2.89 (m, 1H); 2.35 (m, 1H); 2.18 (m, 2H); 1.88 (m, 2H); 1.26; 1.19 (2t, 2x 3H, 2x ethyl-CH$_3$); 1.02; 0.88 ppm (2x 2H, 4x cyclopropyl-H).

EXAMPLE 53

(1'RS,2'RS,6'RS)-7-(2'-Aminomethyl-8'-azabicyclo [4.3.0]-non-4'-en-8'-yl)-1-cyclopropyl-6-fluoro-1,4-dihydro-4-oxo-1,8-naphthyridine-3-carboxylic acid

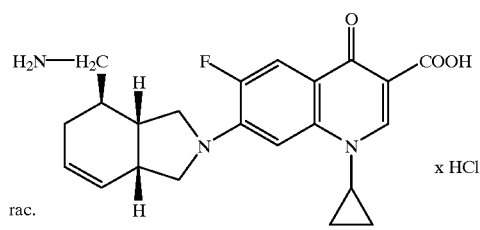

0.70 g of the product from Example 52 is stirred in 7 ml of 1,2-ethanediol and 10 ml of 10% strength potassium hydroxide solution at 130° C. for 4 h. After cooling, the mixture is diluted with acetonitrile and adjusted to pH 2 with dilute hydrochloric acid. Subsequently, it is concentrated to a volume of about 10 ml in vacuo and the product is precipitated by the addition of acetone. The crystals are dried at 50° C. in a vacuum drying oven.

Yield: 0.30 g (47% of theory), hydrochloride. Melting point: >300° C.

EXAMPLE 54

7-[(1'RS,2'RS,6'RS)-2'-Aminomethyl-8'-azabicyclo [4,3,0]non-4'-en-8'-yl]-6,8-difluoro-1-[(1RS,2SR)-2-fluorocyclopropyl]-1,4-dihydro-4-oxo-3-quinolinecarboxylic acid hydrochloride.

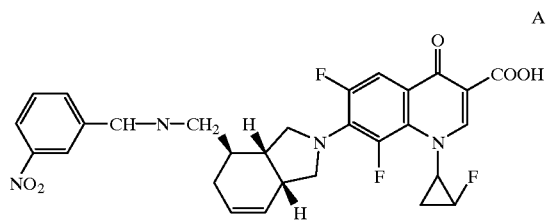

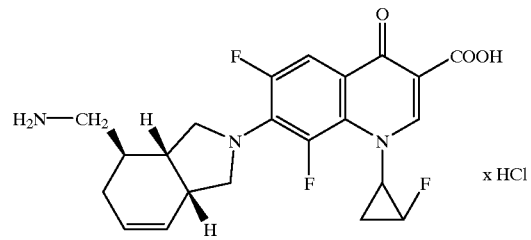

A. 112 mg (1 mmol) of 1,4-diazabicyclo[2,2,2]octane (Dabco) and a solution of 155 mg of 3-nitrobenzaldehyde in 1 ml of acetonitrile are added to 380 mg (1 mmol) of (1RS,2RS,6RS)-2-aminomethyl-8-azabicyclo[4.3.0]non-4-ene bis-trifluoroacetate (product from Example L) in 1 ml of acetonitrile. The mixture is stirred at room temperature for 1 hour and then diluted with 1 ml of dimethylformamide; 224 mg (2 mmol) of Dabco and 270 mg (0.9 mmol) of 6,7,8-trifluoro-1-[(1RS,2SR)-2-fluorocyclopropyl]-1,4-dihydro-4-oxo-3-quinolinecarboxylic acid are then added and the mixture is heated under reflux for 1 hour. It is then concentrated and stirred with water, and then filtering takes place with suction followed by drying at 80° C. under high vacuum.

Yield: 480 mg of 6,8-difluoro-1-[(1RS,2SR)-2-fluorocyclopropyl]-1,4-dihydro-7-[(1'RS,2'RS,6'RS)-2'-(3-nitrobenzylideneaminomethyl)-8'-azabicyclo[4.3.0]non-4'-en-8'-yl]-4-oxo-3-quinolinecarboxylic acid, R$_f$ value (silica gel; dichloromethane/methanol/17% ammonia=30:8:1): 0.5.

B. 450 mg of the product from step A are dissolved in about 30 ml of dichloromethane and 3 ml of 3N hydrochloric acid are then added. The mixture is stirred at room temperature for 30 minutes and then about 30 ml of water are added. The aqueous phase is separated off, washed. with dichloromethane, and lyophilized.

Yield; 170 mg of 7-[(1'RS,2'RS,6'RS)-2'-aminomethyl-8'-azabicyclo[4.3.0]non-4'-en-8'-yl]-6,8-difluoro-1-[(1RS,2SR)-2-fluorocyclopropyl)-1,4-dihydro-4-oxo-3-quinolinecarboxylic acid hydrochloride, R$_f$ value (silica gel; dichloromethane/methanol/17% ammonia=30:8:1): 0.06.

$^1$H-NMR (CF$_3$COOD): δ=5.07 m and 5.2 ppm (m, 1H, CH-F).

EXAMPLE 55

(1'SR,2'RS,6'RS)-1-Cyclopropyl-6,8-difluoro-1,4-dihydro-7-(2'-methylamino-8'-azabicyclo[4.3.0]non-4'-en-8'-yl)-4-oxo-3-quinolinecarboxylic acid

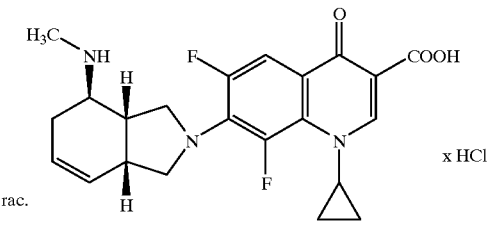

The title compound is obtained by reacting 1-cyclopropyl-6,7,8-trifluoro-1,4-dihydro-4-oxo-3-quinolinecarboxylic acid with the title compound from Example N, as described in Example 22.

Yield: 61% of theory, hydrochloride. Melting point; >300° C.

EXAMPLE 56

(1'SR,2'RS,6'RS)-1-Cyclopropyl-6-fluoro-1,4-dihydro-7-(2'-methylamino-8'-azabicyclo[4.3.0]non-4'-en-8'-yl)-4-oxo-3-quinolinecarboxylic acid

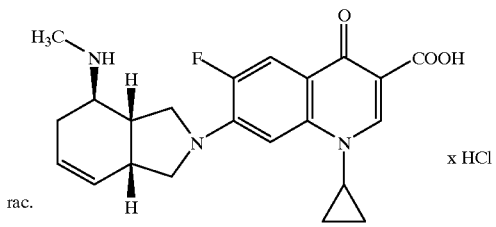

The title compound is obtained by reacting 1-cyclopropyl-6,7-difluoro-1,4-dihydro-4-oxo-3-quinolinecarboxylic acid with the title compound from Example N, as described in Example 22.

Yield: 60% of theory, hydrochloride. Melting point: >300° C.

EXAMPLE 57

(1'SR,2'RS,6'RS)-8-Chloro-1-cyclopropyl-6-fluoro-1,4-dihydro-7-(2'-methylamino-8'-azabicyclo[4.3.0non-4'-en-8'-yl)-4-oxo-3-quinolinecarboxylic acid

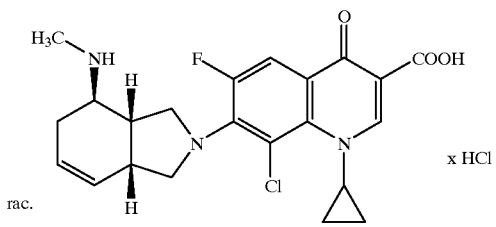

The title compound is obtained by reacting 8-chloro-1-cyclopropyl-6,7-difluoro-1,4-dihydro-4-oxo-3-quinolinecarboxylic acid with the title compound from Example N, as described in Example 22.

Yield: 70% of theory, hydrochloride. Melting point: >300° C.

EXAMPLE 58

(1'SR,2'SR,6'RS)-1-Cyclopropyl-6,8-difluoro-1,4-dihydro-7-(2'-methylamino-8'-azabicyclo[4.3.0]non-4'-en-8'-yl)-4-oxo-3-quinolinecarboxylic acid

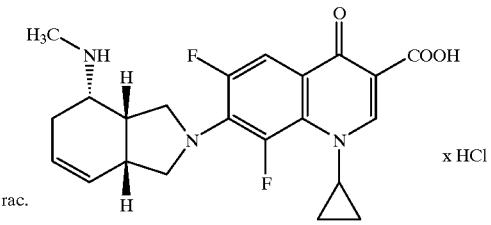

The title compound is obtained by reacting 1-cyclopropyl-6,7,8-trifluoro-1,4-dihydro-4-oxo-3-quinolinecarboxylic acid with the title compound from Example O, as described in Example 22.

Yield: 35% of theory, hydrochloride. Melting point: >300° C.

EXAMPLE 59

(1'SR,2'SR,6'RS)-8-Chloro-1-cyclopropyl-6-fluoro-1,4-dihydro-7-(2'-methylamino-8'-azabicyclo[4.3.0] non-4'-en-8'-yl)-4-oxo-3-quinolinecarboxylic acid

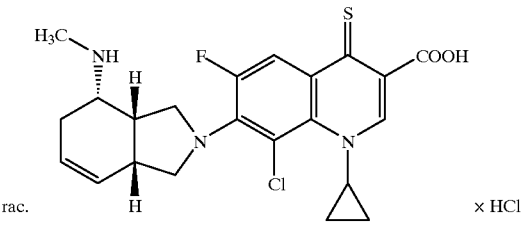

The title compound is obtained by reacting 8-chloro-1-cyclopropyl-6,7-difluoro-1,4-dihydro-4-oxo-3-quinolinecarboxylic acid with the title compound from Example O, as described in Example 22.

Yield: 78% of theory, hydrochloride. Melting point: >300° C.

EXAMPLE 60

(1'SR,2'SR,6'RS)-1-Cyclopropyl-6-fluoro-1,4-dihydro-7-(2'-methylamino-8'-azabicyclo[4.3.0]non-4'-en-8'-yl)-4-oxo-3-quinolinecarboxylic acid

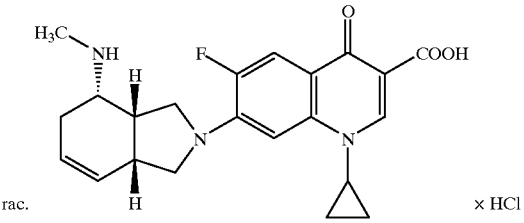

The title compound is obtained by reacting 1-cyclopropyl-6,7-difluoro-1,4-dihydro-4-oxo-3-quinolinecarboxylic acid with the title compound from Example O, as described in Example 22.

Yield: 66% of theory, hydrochloride. Melting point; >300° C.

EXAMPLE 61

Ethyl (1'SR,2'SR,6'RS)-1-cyclopropyl-6-fluoro-1,4-dihydro-7-(2'-methylamino-8'-azabicyclo[4.3.0]non-4'-en-8'-yl)-4-oxo-1,8-naphthyridine-3-carboxylate

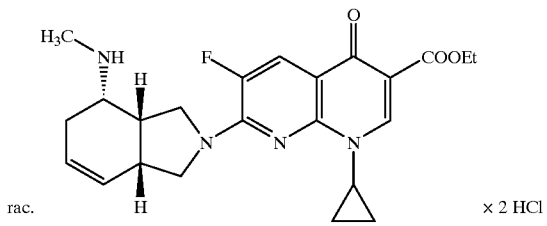

The title compound is obtained by reacting ethyl 7-chloro-1-cyclopropyl-6-fluoro-1,4-dihydro-4-oxo-1,8-naphthyridine-3-carboxylate with the title compound from Example O, as described in Example 52. The hydrochloride is obtained by treating the product with a little dilute hydrochloric acid.

Yield: 91% of theory. $R_f$=0.64 (methanol/dichloromethane/conc. ammonia 15:4:0.5).

EXAMPLE 62

(1'SR,2'SR,6'RS)-1-Cyclopropyl-6-fluoro-1,4-dihydro-7-(2'-methylamino-8'-azabicyclo[4.3.0]non-4'-en-8'-yl) -4-oxo-1,8-naphthyridine-3-carboxylic acid

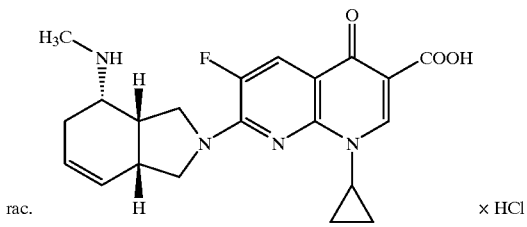

The product from Example 61 is reacted as described in Example 27.

Yield: 89% of theory, hydrochloride. Melting point: >300° C. $R_f$=0.32 (methanol/dichloromethane/conc. ammonia 15:5:0.5).

| Abbreviations employed: | |
|---|---|
| h | hour(s) |
| min | minute(s) |
| conc. | concentrated |
| DMF | dimethylformamide |
| THF | tetrahydrofuran |
| MTBE | tert-butyl methyl ether |
| DIBAH | diisobutylaluminium hydride |
| DABCO | 1,4-diazabicyclo[2.2.2]octane |
| DMSO | dimethyl sulphoxide |

We claim:
1. An Isoindole of the formula (III)

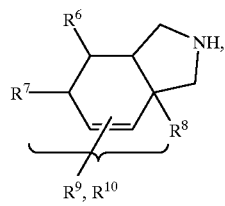

in which
$R^6$ represents hydrogen, alkyloxycarbonyl having 1 to 4 carbon atoms, hydroxymethyl,

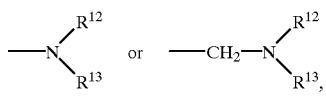

where
$R^{12}$ denotes hydrogen, alkyl having 1 to 3 carbon atoms, which is optionally substituted by hydroxyl, alkyloxycarbonyl having 1 to 4 carbon atoms in the alkyl moiety, or acyl having 1 to 3 carbon atoms, and
$R^3$ denotes hydrogen or methyl,
$R^7$, $R^8$, $R^9$ and $R^{10}$ ( each represent hydrogen or methyl or $R^9$ and $R^{10}$ each represent hydrogen or methyl and $R^7$, together with $R^8$, can form a bridge of the structure —O—, —CH$_2$— or —CH$_2$—CH$_2$— with the exception of 8-Azabicyclo[4.3.0]non-2-ene and 10-Oxa-3-aza-tricyclo[5.2.1.0$^{1,5}$]dec-8-ene.
2. An isoindole selected from the group consisting of
Ethyl 8-azabicyclo[4.3.0]non-4-ene-2-carboxylate
2-Hydroxymethyl-8-azabicyclo[4.3.0]non-4-ene
2-Amino-8-azabicyclo[4.3.0]non-4-ene
2-Ethyloxycarbonylamino-8-azabicyclo[4.3.0]non-4-ene
2-tert-Butyloxycarbonylamino-8-azabicyclo[4.3.0]non-4-ene
2-Benzyloxycarbonylamino-8-azabicyclo[4.3.0]non-4-ene
2-Allyloxycarbonylaminomethyl-8-azabicyclo[4.3.0]-non-4-ene
2-Aminomethyl-8-azabicyclo(4.3.0)non-4-ene
2-Ethyloxycarbonylaminomethyl-8-azabicyclo[4.3.0]-non-4-ene
2-tert-Butyloxycarbonylaminomethyl-8-azabicyclo-[4.3.0]non-4-ene
2-Methylamino-8-azabicyclo[4.3.0]non-4-ene
2-Ethylamino-8-azabicyclo[4.3.0]non-4-ene
2-Dimethylamino-8-azabicyclo[4.3.0]non-4-ene
2-[(2-Hydroxyethyl) -amino]-8-azabicyclo[4.3.0]non-4-ene
2-Amino-3-methyl-8-azabicyclo[4.3.0]non-4-ene
2-Ethyloxycarbonylamino-3-methyl-8-azabicylo-[4.3.0]non-4-ene
2-tert-Butyloxycarbonylamino-3-methyl-8-azabicyclo-[4.3.0]non-4-ene
2-Benzyloxycarbonylamino-3-methyl-8-azabicyclo-[4.3.0]non-4-ene
2-Allyloxycarbonylamiomethyl-3-methyl-8-azabicyclo-[4.3.0]non-4-ene
2-Amino-4-methyl-8-azabicyclo[4.3.0]non-4-ene
2-Amino-5-methyl-8-azabicyclo[4.3.0]non-4-ene
2-Amino-6-methyl-8-azabicyclo[4.3.0]non-4-ene
6-Amino-10-oxa-3-azatricyclo[5.2.1.0$^{1,5}$]dec-8-ene 6-Ethyloxycarbonylamino-10-oxa-3-azatricyclo-[5.2.1.0$^{1,5}$]dec-8-ene 6-tert-Butyloxycarbonylamino-10-oxa-3-azatricyclo-[5.2.1.0$^{1,5}$]dec-8-ene 6-Aminomethyl-10-oxa-3-azatricyclo[5.2.1.0$^{1,5}$]dec-8-ene 6-Ethyloxycarbonylaminomethyl-10-oxa-3-azatricyclo-[5.2.1.0$^{1,5}$]dec-8-ene 6-tert-Butyloxycarbonylaminomethyl-10-oxa-3-azatricyclo[5.2.1.0$^{1,5}$]dec-8-ene 6-Amino-3-azatricyclo[5.2.1.0$^{1,5}$]dec-8-ene 6-Amino-3-azatricyclo[5.2.2.0$^{1,5}$]undec-8-ene as well as their racemates and also their enantiomerically or diastereomerically pure compounds.

3. Process comprising reacting a compound of the formula (II)

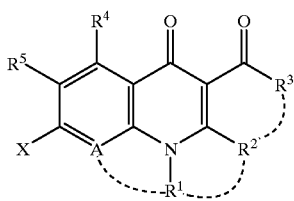

(II)

in which

R$^1$ represents alkyl having 1 to 4 carbon atoms, which is optionally substituted by 1–3 fluorine atoms, alkenyl having 2 to 4 carbon atoms, cycloalkyl having 3 to 6 carbon atoms, which is optionally substituted by 1 to 2 fluorine atoms, 2-hydroxyethyl, methoxy, amino, methylamino, ethylamino, dimethylamino, phenyl, which is optionally substituted by 1 or 2 fluorine atoms, 3-oxetanyl, bicyclo (1.1.1) pentyl, R$^2$ represents hydrogen or else, together with R$^1$, can form a bridge, so that a 4- or 5-membered ring results, R$^3$ represents hydroxyl or O-R$^{11}$, wherein R$^{11}$ represents alkyl having 1–4 C atoms or R$^3$, together with R$^2$, can form a bridge, so that a 5- or 6-membered ring results, R$^4$ represents hydrogen, amino, alkylamino having 1 to 4 carbon atoms, dialkylamino having 1 to 3 carbon atoms in each alkyl group, hydroxyl, alkoxy having 1 to 4 carbon atoms, mercapto, alkylthio having 1 to 4 carbon atoms, halogen, methyl, ethyl or vinyl, R$^5$ represents hydrogen, halogen or methyl, A represents N or C-R$^{14}$, wherein R$^{14}$ represents hydrogen, halogen, methyl, which is optionally substituted by 1 to 3 fluorine atoms, ethinyl, vinyl, hydroxyl or methoxy, or, together with R$^1$, form a bridge, so that a 5- or 6-membered ring results, or, together with R$^1$ and R$^2$, form a bridge, so that two 5- or 6-membered rings result, X represents halogen, with a compound of the formula (III) according to claim 1 optionally in the presence of acid binders, and eliminating protective groups which are present by alkaline or acid hydrolysis, and optionally converting the resulting compounds into their alkali metal, alkaline earth metal silver or guanidinium salts.

* * * * *